US011459562B2

(12) United States Patent
Zamore et al.

(10) Patent No.: US 11,459,562 B2
(45) Date of Patent: Oct. 4, 2022

(54) METHODS AND COMPOSITIONS FOR CONTROLLING EFFICACY OF RNA SILENCING

(71) Applicant: UNIVERSITY OF MASSACHUSETTS, Boston, MA (US)

(72) Inventors: Phillip D. Zamore, Northboro, MA (US); Guiliang Tang, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 370 days.

(21) Appl. No.: 16/440,722

(22) Filed: Jun. 13, 2019

(65) Prior Publication Data

US 2020/0032261 A1   Jan. 30, 2020

Related U.S. Application Data

(60) Continuation of application No. 13/917,480, filed on Jun. 13, 2013, now Pat. No. 10,364,429, which is a continuation of application No. 12/802,534, filed on Jun. 7, 2010, now abandoned, which is a continuation of application No. 12/139,072, filed on Jun. 13, 2008, now Pat. No. 7,732,593, which is a continuation of application No. 10/859,337, filed on Jun. 2, 2004, now Pat. No. 7,459,547, said application No. 13/917,480 is a continuation of application No. 12/802,836, filed on Jun. 7, 2010, now Pat. No. 8,522,707, which is a division of application No. 12/172,938, filed on Jul. 14, 2008, now Pat. No. 7,772,203, which is a division of application No. 10/859,337, filed on Jun. 2, 2004, now Pat. No. 7,459,547.

(60) Provisional application No. 60/475,386, filed on Jun. 2, 2003.

(51) Int. Cl.
C12N 15/113 (2010.01)
C12N 15/11 (2006.01)
C12N 15/82 (2006.01)

(52) U.S. Cl.
CPC .......... *C12N 15/113* (2013.01); *C12N 15/111* (2013.01); *C12N 15/8218* (2013.01); *C12N 15/8261* (2013.01); *C12N 2310/14* (2013.01); *C12N 2310/335* (2013.01); *C12N 2320/50* (2013.01); *Y02A 40/146* (2018.01)

(58) Field of Classification Search
CPC .............. C12N 15/113; C12N 15/8218; C12N 2310/14
See application file for complete search history.

(56) References Cited

U.S. PATENT DOCUMENTS

| | | |
|---|---|---|
| 6,506,559 B1 | 1/2003 | Fire et al. |
| 7,459,547 B2 | 12/2008 | Zamore et al. |
| 7,595,387 B2 | 9/2009 | Leake et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 8,090,542 B2 | 1/2012 | Khvorova et al. |
| 2002/0086356 A1 | 7/2002 | Tuschl et al. |
| 2002/0173478 A1 | 11/2002 | Gewirtz |
| 2003/0108923 A1 | 6/2003 | Tuschl et al. |
| 2004/0002153 A1 | 1/2004 | Monia et al. |
| 2004/0053411 A1 | 3/2004 | Cullen et al. |
| 2004/0096843 A1 | 5/2004 | Rossi et al. |
| 2004/0137471 A1 | 7/2004 | Vickers et al. |
| 2004/0175703 A1 | 9/2004 | Kreutzer et al. |
| 2004/0180351 A1 | 9/2004 | Giese et al. |
| 2004/0192629 A1 | 9/2004 | Xu et al. |
| 2004/0203145 A1 | 10/2004 | Zamore et al. |
| 2004/0214198 A1 | 10/2004 | Rana |
| 2004/0224328 A1 | 11/2004 | Prydz et al. |
| 2004/0229266 A1 | 11/2004 | Tuschl et al. |
| 2004/0248299 A1 | 12/2004 | Jayasena et al. |
| 2004/0259247 A1 | 12/2004 | Tuschl et al. |
| 2004/0259248 A1 | 12/2004 | Tuschl et al. |
| 2005/0020521 A1 | 1/2005 | Rana |
| 2005/0026278 A1 | 2/2005 | Tuschl et al. |
| 2005/0037988 A1 | 2/2005 | Zamore et al. |
| 2005/0059005 A1 | 3/2005 | Tuschl et al. |
| 2005/0181382 A1 | 8/2005 | Zamore et al. |
| 2005/0182005 A1 | 8/2005 | Tuschl et al. |
| 2005/0186586 A1 | 8/2005 | Zamore et al. |
| 2005/0227256 A1 | 10/2005 | Hutvagner et al. |
| 2005/0227940 A1 | 10/2005 | Rossi et al. |
| 2005/0234007 A1 | 10/2005 | Tuschl et al. |

(Continued)

FOREIGN PATENT DOCUMENTS

| | | |
|---|---|---|
| CA | 2432341 A1 | 7/2002 |
| CA | 2432350 A1 | 7/2002 |
| DE | 10160151 A1 | 6/2003 |

(Continued)

OTHER PUBLICATIONS

Xiao et al (Int. J. Oncol. 46:161-174, 2015) (Year: 2015).

(Continued)

*Primary Examiner* — Richard A Schnizer
(74) *Attorney, Agent, or Firm* — Lathrop GPM LLP; James H. Velema, Esq.; Michael Spellberg, Esq.

(57) ABSTRACT

Based at least in part on an understanding of the mechanisms by which small RNAs (e.g., naturally-occurring miRNAs) mediate RNA silencing in plants, rules have been established for determining, for example, the degree of complementarity required between an RNAi-mediating agent and its target, i.e., whether mismatches are tolerated, the number of mismatches tolerated, the effect of the position of the mismatches, etc. Such rules are useful, in particular, in the design of improved RNAi-mediating agents which allow for more exact control of the efficacy of RNA silencing.

24 Claims, 12 Drawing Sheets

Specification includes a Sequence Listing.

(56) References Cited

U.S. PATENT DOCUMENTS

| | | |
|---|---|---|
| 2005/0244858 A1 | 11/2005 | Rossi et al. |
| 2005/0246794 A1 | 11/2005 | Khvorova et al. |
| 2005/0256072 A1 | 11/2005 | Aronin et al. |
| 2005/0273868 A1 | 12/2005 | Rana |
| 2005/0277610 A1 | 12/2005 | Rossi et al. |
| 2006/0009402 A1 | 1/2006 | Zamore et al. |
| 2006/0069050 A1 | 3/2006 | Rana |
| 2006/0128650 A1 | 6/2006 | Xu |
| 2006/0134787 A1 | 6/2006 | Zamore et al. |
| 2006/0166910 A1 | 7/2006 | Tuschl et al. |
| 2006/0178334 A1 | 8/2006 | Rossi et al. |
| 2006/0212950 A1 | 9/2006 | Tuschl et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0031844 A1 | 2/2007 | Khvorova et al. |
| 2007/0039072 A1 | 2/2007 | Khvorova et al. |
| 2007/0093445 A1 | 4/2007 | Tuschl et al. |
| 2007/0104688 A1 | 5/2007 | Rossi et al. |
| 2007/0111228 A1 | 5/2007 | Jayasena et al. |
| 2007/0207974 A1 | 9/2007 | Khvorova et al. |
| 2007/0265220 A1 | 11/2007 | Rossi et al. |
| 2010/0184826 A1 | 7/2010 | Zamore et al. |
| 2010/0184827 A1 | 7/2010 | Zamore et al. |
| 2010/0184828 A1 | 7/2010 | Zamore et al. |

FOREIGN PATENT DOCUMENTS

| | | |
|---|---|---|
| EP | 1389637 A1 | 2/2004 |
| EP | 1527176 B1 | 5/2005 |
| EP | 1857547 A2 | 11/2007 |
| WO | WO 01/75164 A2 | 10/2001 |
| WO | WO 02/44321 A2 | 6/2002 |
| WO | WO 02/055692 A2 | 7/2002 |
| WO | WO 02/055693 A2 | 7/2002 |
| WO | WO 03/020931 A2 | 3/2003 |
| WO | WO 03/035869 A1 | 5/2003 |
| WO | WO 03/064621 A2 | 8/2003 |
| WO | WO 03/068797 A1 | 8/2003 |
| WO | WO03/093441 A2 | 11/2003 |
| WO | WO 04/015107 A2 | 2/2004 |
| WO | WO 04/027030 A2 | 4/2004 |
| WO | WO 04/029212 A2 | 4/2004 |
| WO | WO 04/045543 A2 | 6/2004 |
| WO | WO 04/046324 A2 | 6/2004 |
| WO | WO 04/061083 A2 | 7/2004 |
| WO | WO 04/063375 A1 | 7/2004 |
| WO | WO 04/064737 A2 | 8/2004 |
| WO | WO 04/080406 A2 | 9/2004 |
| WO | WO 05/001043 A2 | 1/2005 |
| WO | WO 05/062937 A2 | 7/2005 |
| WO | WO 05/069987 A2 | 8/2005 |
| WO | WO 05/079532 A2 | 9/2005 |
| WO | WO 05/079533 A2 | 9/2005 |
| WO | WO 05/089287 A2 | 9/2005 |
| WO | WO 06/015389 A2 | 2/2006 |

OTHER PUBLICATIONS

GenBank Accession NM 000138 (2018) (Year: 2018).
Pandey et al (Exp. Clin. Immunogen. 18(3):123-129, 2001) (Year: 2001).
Gen Bank Accession NM 001290043 (Year: 2018).
Koch et al (J. Biol. Chem. 279(11): 10142-10147, 2004) (Year: 2004).
GenBank accession XM 011532399.2 (2016) (Year: 2016).
Hasegawa et al (Oncology Letters 10: 2986-2990, 2015) (Year: 2015).
Home et al (J. Biol. Chem. 271(11): 6050-6061, 1996) (Year: 1996).
Bernaudo et al (Oncogene (2016) 35,4816-4827) (Year: 2016).
GenBank accession XM 017002022 (2016) (Year: 2016).
http://www.uniprot.org/uniprot/O9H4A4, downloaded from the web on Jan. 16, 2018 (Year: 2018).
GenBank accession XR 001745593.1 (2016) (Year: 2016).
Ma et al (Nature Scientific Reports Oct. 12, 2015;5:15121) (Year: 2015).
GenBank XM 015087918, 2015.
GenBank AK127164, 2008.
Leger, et al., "Analysis of Expressed Sequence Tag in Pedunculate and Sessile Oaks." Genbank. 2010, FN703363.
Suzuki, et al., "Sequence Comparison of Human and Mouse Genes Revevals a Homologous Block Structure in the Promoter Regions." Genome Research. 14(9): 1711-1718 Genbank: BP268282.1.
GenBank Accession BP268282 (2011).
GenBank FN703363 (2010).
Lagos-Quintana, Mariana et al. "Identification of Novel Genes Coding for Small Expressed RNAs," Science, vol. 294:853-858 (2001).
Lagos-Quintana, Mariana et al. "Identification of Tissue-Specific MicroRNAs from Mouse," Current Biology, vol. 12:735-739 (2002).
Lagos-Quintana, Mariana et al. "New microRNAs from mouse and human," RNA, vol. 9:175-179 (2003).
Lai, E.C., "Micro RNAs are complementary to 3' UTR sequence motifs that mediate negative post-transcriptional regulation," Nat. Genet., vol. 30(4):363-364 (2002).
Lau, Nelson C. et al., "An Abundant Class of Tiny RNAs with Probable Regulatory Roles in Caenorhabditis elegans," Science, vol. 294:858-862 (2001).
Lee, Rosalind C. et al., "An Extensive Class of Small RNAs in Caenorhabditis elegans," Science, vol. 294:862-864 (2001).
Lee, Rosalind C. et al., "The C. elegans Heterochronic Gene lin-4 Encodes Small RNAs with Antisense Complementarity to lin-14," Cell, vol. 75:843-854 (1993).
Lewin, Benjamin, Genes VII, Oxford University Press, Oxford, p. 9 (2000).
Lewis, David L. et al., "Efficient delivery of siRNA for inhibition of gene expression in postnatal mice," Nature Genetics, vol. 32:107-108 (2002).
Lewis, Benjamin P. et al., "Prediction of Mammalian MicroRNA Targets," Cell, vol. 115:787-798 (2003).
Li, Bao-jian et al., "Using siRNA in Pophylactic and Therapeutic Regimens Against SARS Coronavirus in Rhesus Macaque," Nature Medicine, vol. 11 (9):944-951 (2005).
Li, Wan Xiang et al., "Viral suppressors of RNA silencing," Current Opinion in Biotechnology. vol. 12:150-154, (2001).
Liang, Xue-hai et al., "Small nuclear RNA interference induced by antisense or double-stranded RNA in trypanosomatids," PNAS, vol. 100(13):7521-7526 (2003).
Lieberman, Judy et al., "Interfering with disease: opportunities and roadblocks to harnessing RNA interference," Trends in Molecular Medicine, vol. 9(9):397-403 (2003).
Lim, Lee P. et al, "Microarray analysis shows that some microRNAs downregulate large numbers of target mRNAs," Nature, vol. 433:769-773 (2005).
Lim, Lee P. et al., "The microRNAs of Caenorhabditis elegans," Genes & Development, vol. 17:991-1008 (2003).
Lim, Lee P. et al., "Vertebrate MicroRNA Genes," Science, vol. 299:1540 (2003).
Liu, Jidong et al., "Argonaute2 Is the Catalytic Engine of Mammalian RNAi," Science, vol. 305:1437-1441 (2004).
Liu, Qinghua et al., "R2D2, a Bridge Between the Initiation and Effector Steps of the *Drosophila* RNAi Pathway," Science, vol. 301:1921-1925 (2003).
Llave, Cesar et al., "Cleavage of Scarecrow-like mRNA Targets Directed by a Class of *Arabidopsis* miRNA," Science . vol. 297:2053-2056, (2002).
Lodish, Harvey et al., Molecular Cell Biology, Fourth Edition, Sara Tenney (Ed.), W.H. Freeman and Company, New York, p. 103 (2001).
Long, Dang et al., "Potent effect of target structure on microRNA function," Nature Structural & Molecular Biology, vol. 14(4):287-294 (2007).

(56) References Cited

OTHER PUBLICATIONS

Luo, Kathy Q. et al., "The gene-silencing efficiency of siRNA is strongly dependent on the local structure of mRNA at the targeted region," Biochemical and Biophysical Research Communications, vol. 318:303-310 (2004).
Mallory, Allison C. et al, "MicroRNA control of PHABULOSA in leaf development: importance of pairing to the microRNA 5' region," The EMBO Journal, vol. 23:3356-3364 (2004).
Martens, Henrik et al., "RNAi in Dictyostelium : The Role of RNA-directed RNA Polymerases and Double-stranded RNase," Molecular Biology of the Cell . vol. 13:445-453, (2002).
Martinez, Luis Alfonso et al, "Synthetic small inhibiting RNAs: Efficient tolls to inactivate oncogenic mutations and restore p53 pathways," PNAS, vol. 99(23):14849-14854 (2002).
Martinez, Javier et al., "RISC is a 5' phosphomonoester-producing RNA endonuclease," Genes & Development, vol. 18:975-980 (2004).
Martinez, J. et al., "Single-stranded antisense siRNAs guide target RNA cleavage in RNAi," Cell, vol. 110 (5):563-574 (2002).
Matranga, Christian et al., "Passenger-Strand Cleavage Facilitates Assembly of siRNA into Agog-Containing RNAi Enzyme Complexes," Cell, vol. 123:607-620 (2005).
Mccaffrey, Anton P. et al., "RNA interference in adult mice," Nature, vol. 418:38-39 (2002).
Mcconnell, Jane R. et al., "Role of PHABULOSA and PHAVOLUTA in determining radial patterning in shoots," Nature . vol. 411:709-713, (2001).
Mcmanus, Michael T. et al., "Gene Silencing in Mammals By Small Interfering RNAs," Nature Reviews Genetics, vol. 3:737-747 (2002).
Mcmanus, Michael T. et al., "Gene silencing using micro-RNA designed hairpins," RNA, vol. 8:842-850 (2002).
Meister, Gunter et al., "Human Argonaute2 Mediates RNA Cleavage Targeted by miRNAs and siRNAs," Molecular Cell, vol. 15:185-197 (2004).
Meister, Gunter et al, "Sequence-specific inhibition of microRNA- and siRNA-induced RNA silencing," RNA, vol. 10:544-550 (2004).
Merriam-Webster Online Dictionary, "Pharmaceutical," http://www.merriam-webstercom/dictionary/ pharmaceutical (2008).
Merriam-Webster online, "engineer," retrieved online at http://www.merriam-webster.com/dictonary (2008).
Molecular Biology of the Cell, Fourth Edition, "DNA Replication Mechanisms," retrieved online at http://www.ncbi.nlm. nih.gov/books/bv.fcgi?highlight=DNA&rid=mboc4.section.754 (2008).
Molecular Biology of the Cell, Fourth Edition, "Figure 4-4," retrieved online at http://www.ncbi.nlm.nih.gov/books/bv. fcgi?rid=mboc4.figgrp (2008).
Molecular Biology of the Cell, Fourth Edition, "The Chemical Composition of a Cell," retrieved online at http://www.ncbi.nlm.nih.gov/books/bv.fcgi?highlight=hydrogen,dna,bond&rid=mboc4.section165 (2008).
Molecular Biology of the Cell, Fourth Edition, "Wobble base-pairing between codons and anticodons," retrieved online at http://www.ncbi.nlm.nih.gov/books/bv.fcgi?highlight=inosine&rid=mbocA.figgrp.1058 (2008).
Moss, Eric G. et al., "The Cold Shock Domain Protein LIN-28 Controls Developmental Timing in C. elegans and Is Regulated by the lin-4 RNA," Cell, vol. 88:637-646 (1997).
Mourelatos, Zissimos et al., "miRNPs: a novel class of ribonucleoproteins containing numerous microRNAs," Genes & Development, vol. 16:720-728 (2002).
Mourrain, Philippe et al., "Arabidopsis SGS2 and SGS3 Genes Are Required for Posttranscriptional Gene Silencing and Natural Virus Resistance," Cell, vol. 101:533-542 (2000).
Murchison, E.P. et al., "miRNAs on the move: miRNA biogenesis and the RNAi machinery," Curr. Opin. Cell. Biol., vol. 16(3):223-229 (2004).
Notice of opposition to a European patent, Alcon Research Ltd., Application No. EP 04 753 972.1, dated Jul. 20, 2011.
Notice of opposition to a European patent, Alnylam Pharmaceuticals, Inc., Application No. EP 04 753 972.1, dated Oct. 29, 2010.

Notice of opposition to a European patent, Novartis AG, Application No. EP 04 753 972.1, dated Jul. 20, 2011.
Nykanen, A. et al., "ATP requirements and small interfering RNA structure in the RNA interference pathway," Cell, vol. 107(3):309-321 (2001).
Ohnishi, Yusuke et al, "Influence of assembly of siRNA elements into RNA-induced silencing complex by fork-siRNA duplex carrying nucleotide mismatches at the 3'- or 5'-end of the sense-stranded siRNA element," Biochemical and Biophysical Research Communications, vol. 329:516-521 (2005).
Song, E. et al., "Intrahepatic Gene Silencing by RNA Interference," Gastroenterology, vol. 126(1):356-358 (2004).
Song, Erwei et al., "RNA interference targeting Fas protects mice from fulminant hepatitis," Nature Medicine, vol. 9 (3):347-351 (2003).
Sontheimer, Erik J. et al., "Argonaute Journeys into the Heart of RISC," Science, vol. 305:1409-1410 (2004).
Soutschek, Jurgen et al, "Therapeutic Silencing of an Endogenous Gene by Systemic Administration of Modified si RNAs," Nature Publishing Group, vol. 432, 173-178 (2004).
Stark, Alexander et al. "Identification of *Drosophila* MicroRNA Targets," PLOS Biology, vol. 1(3):397-409 (2003).
Sundaralingam, Muttaiya et al., "Hydrogen and hydration of DNA and RNA oligonucleotides," Biophysical Chemistry, vol. 95:273-282 (2002).
Tabara, Hiroaki et al., "The dsRNA Binding Protein RDE-4 Interacts with RDE-1, DCR-1, and a DExH-Box Helicase to Direct RNAi in C. elegans," Cell, vol. 109:861-871 (2002).
Tabara, Hiroaki et al., "The rde-1 Gene, RNA Interference and Transposon Silencing in C. elegans," Cell, vol. 99:123-132 (1999).
Tan, P.H. et al., "Gene Knockdown with Intrathecal siRNA of NMDA Receptor NR2B Subunit Reduces Formalin-induced Nociception in the Rat," Gene Therapy, vol. 12, 59-66 (2005).
Tang, Guiliang et al., "A biochemical framework for RNA silencing in plants," Genes & Development, vol. 17:49-63 (2003).
Tang, G. et al., "Biochemical dissection of RNA silencing in plants," Methods Mol. Biol., vol. 257:223-244 (2004).
Thakker, Deepak R. et al, "Neurochemical and Behavioral Consequences of Widespread Gene Knockdown in the Adult Mouse Brain by Using Nonrival Interference," PNAS, vol. 101:49, 17270-17275 (2004).
Tijsterman, Marcel et al., "PPW-1, a PAZ/PIWI Protein Required for Efficient Germline RNAi, Is Defective in a Natural Isolate of C. elegans," Current Biology, vol. 12:1535-1540 (2002).
Tijsterman, Marcel et al., "RNA Helicase MUT-14-Dependent Gene Silencing Triggered in C. elegans by Short Antisense RNAs," Science, Vo. 295:694-697 (2002).
Tomari, Yukihide et al., "Perspective: machines for RNAi," Genes & Development, vol. 19:517-529 (2005).
Tomari, Y. et al., "RISC assembly defects in the *Drosophila* RNAi mutant armitage," Cell, vol. 116(6):831-841 (2004).
Tuschl, Thomas et al., "siRNAs and miRNAs," Keystone Symposia, Abstract Book (2004).
Tuschl, Thomas et al., "Targeted mRNA degradation by double-stranded RNA in vitro," Genes & Development, vol. 13:3191-3197 (1999).
Valencia-Sanchez, Marco Antonio et al., "Control of translation and mRNA degradation by miRNAs and siRNAs," Genes & Development, vol. 20:515-524 (2006).
Vargason, Jeffrey M. et al., "Size selective recognition of siRNA by an RNA silencing suppressor," Cell, vol. 115:799-811 (2003).
Vaucheret, Herve et al., "Post-transcriptional gene silencing in plants," Journal of Cell Science, vol. 114:3083-3091, (2001).
Vella, Monica C. et al., "The C. elegans microRNA let-7 binds to imperfect let-7 complementary sites from the lin-41 3'UTR," Genes & Development, vol. 18:132-137 (2004).
Wang, J. et al., "Fas siRNA Reduces Apoptotic Cell Death of Allogeneic-Transplanted Hepatocytes in Mouse Spleen," Transplantation Proceedings, Vo. 35:1594-1595 (2003).
Waterhouse, Peter M. et al., "Gene silencing as an adaptive defense against viruses," Nature, vol. 411:834-842, (2001).

(56) References Cited

OTHER PUBLICATIONS

Wightman, Bruce et al., "Posttranscriptional Regulation of the Heterochronic Gene lin-14 by lin-4 Mediates Temporal Pattern Formation in C. elegans," Cell, vol. 75:855-862 (1993).
Wu-Sharf, Dancia et al., "Transgene and Transposon Silencing in Chlamydomonas reinhardtii by a DEAH-Box RNA Helicase," Science, vol. 290:1159-1162 (2000).
Xia, Haibin et al., "siRNA-mediated gene silencing in vitro and in vivo," Nature Biotechnology, vol. 20:1006-1010 (2002).
Xie, Zhixin et al., "Negative Feedback Regulation of Dicer-Like1 in *Arabidopsis* by microRNA-Guided mRNA Degradation," Current Biology, vol. 13:784-789 (2003).
Xu, Li et al., "Factors Affecting Long-Term Stability of Moloney Murine Leukemia Virus-Based Vectors," Virology, vol. 171:331-341 (1989).
Xu, Peizhang et al., "The *Drosophila* MicroRNA Mir-14 Suppresses Cell Death and Is Required for Normal Fat Metabolism," Current Biology, vol. 13:790-795 (2003).
Yi, Rui et al., "Exportin-5 mediates the nuclear export of pre-microRNAs and short hairpin RNAs," Genes & Development, vol. 17:3011-3016 (2003).
Yuan, Yu-Ren et al., "Crystal Structure of A. aeolicus Argonaute, a Site-Specific DNA-Guided Endoribonuclease, Provides Insights into RISC-Mediated mRNA Cleavage," Molecular Cell, vol. 19:405-419 (2005).
Zamore, Phillip D. et al., "RNAi: Double-Stranded RNA Directs the ATP-Dependent Cleavage of mRNA at 21 to 23 Nucleotide Intervals," Cell, vol. 101:25-33 (2000).
Zeng, Yan et al., "Both Natural and Designed Micro RNAs Can Inhibit the Expression of Cognate mRNAs When Expressed in Human Cells," Molecular Cell, vol. 9:1327-1333 (2002).
Zeng, Yan et al., "MicroRNAs and small interfering RNAs can inhibit mRNA expression by similar mechanisms," PNAS, vol. 100(17):9779-9784 (2003).
Zeng, Yan et al., "Sequence requirements for micro RNA processing and function in human cells," RNA, vol. 9:112-123 (2003).
Zhang, Yingjie et al, "Engineering Mucosal RNA Interference in Vivo," Molecular Therapy, vol. 14:3, 336-342 (2006).
Zhang, Haidi et al., "Human Dicer preferentially cleaves dsRNAs at their termini without a requirement for ATP," The EMBO Journal, vol. 21(21):5875-5885 (2002).
Zimmermann, Tracy S. et al., "RNAi-mediated Gene Silencing in Non-human Primates," Nature, vol. 441, 111-114 (2006).
International Preliminary Reporton Patentability for Application No. PCT/US2004/017130, dated Dec. 8, 2005.
Invitation to Pay Additional Fees for Application No. PCT/USO4/17130, dated Apr. 1, 2005.
Supplementary European Search Report for Application No. EP04753864, dated Mar. 5, 2007.
Written Opinion for Application No. PCT/US2005/029011, dated Apr. 13, 2006.
Invitation to Pay Additional Fees for Application No. PCT/US2005/029011, 5 pages, dated Feb. 20, 2006.
European Search Report for Application No. 04753972.1-2402, dated Oct. 31, 2006.
Canadian Office Action for Application No. 2,528,012, dated Feb. 23, 2011.
Olsen, Philip H. et al., "The lin-4 Regulatory RNA Controls Developmental Timing in Caenorhabditis elegans by Blocking LIN-14 Protein Synthesis after the Initiation of Translation," Developmental Biology, vol. 216:671-680 (1999).
Opalinska, Joanna B. et al., "Nucleic-Acid Therapeutics: Basic Principles and Recent Applications," Nature Reviews Drug Discovery, vol. 1:503-514 (2002).
Opalinska, Joanna B. et al., "Nucleic Acid Therapeutics for Hematologic Malignancies—Theoretical Considerations," Ann. N.Y. Acad. Sci., vol. 1082:124-136 (2006).
Paddison, Patrick J. et al., "Short hairpin RNAs (shRNAs) induce sequence-specific silencing in mammalian cells," Genes & Development, vol. 16:948-958 (2002).

Pal-Bhadra, Manika et al., "RNAi Related Mechanisms Affect both Transcriptional and Posttranscriptional Transgene Silencing in *Drosophila*," Molecular Cell. vol. 9:315-327, (2002).
Park, Wonkeun et al., "Carpel Factory, a Dicer Homolog, and HEN1, a Novel Protein, Act in microRna Metabolism in *Arabidopsis thaliana*," Current Biology, vol. 12:1484-1495, (2002).
Parker, James S. et al., "Structural insights into mRNA recognition from a PIWI domain-siRNA guide complex," Nature, vol. 434:663-666 (2005).
Parrish, Susan et al., "Functional Anatomy of a dsRNA Trigger: Differential Requirement for the Two Trigger Strands in RNA Interference," Molecular Cell, vol. 6:1077-1087 (2000).
Patzel, Volker et al, "Design of siRNAs producing unstructured guide-RNAs results in improved RNA interference efficiency," Nature Biotechnology, vol. 23(11):1440-1444 (2005).
Persengiev, Stephan P. et al., "Nonspecific, concentration-dependent stimulation and repression of mammalian gene expression by small interfering RNAs (siRNAs)," RNA, vol. 10:12-18 (2004).
Pham, John W. et al., "A Dicer-2-Dependent 80S Complex Cleaves Targeted mRNAs during RNAi in *Drosophila*," Cell, vol. 117:83-94 (2004).
Pillai, Ramesh S. et al., "Tethering of human Ago proteins to mRNA mimics the miRNA-mediated repression of protein synthesis," RNA, vol. 10:1518-1525 (2004).
Poy, Matthew N. et al., "A pancreatic islet-specific microRNA regulates insulin secretion," Nature, vol. 432:226-230 (2004).
Pusch, 0. et al., "Nucleotide sequence homology requirements of HIV-1-specific short hairpin RNA," Nucleic Acids Res., vol. 31(22):6444-6449 (2003).
Rand, Tim A. et al., "Argonaute2 Cleaves the Anti-Guide Strand of siRNA during RISC Activation," Cell, vol. 123:621-629 (2005).
Rasmussen, M.H. et al., "Tumor model-specific proviral insertional mutagenesis of the Fos/Jdp2/Batf locus," Virology, vol. 337:353-364 (2005).
Reich, Samuel J. et al, "Small Interfering RNA (siRNA) targeting VEGF Effectively Inhibits Ocular Neovascularization in a Mouse Model," Molecular Vision, vol. 9, 210-216 (2003).
Reinhart, Brenda J. et al., "MicroRNAs in plants," Genes & Development, vol. 16:1616-1626 (2002).
Reinhart, Brenda J. et al., "The 21-nucleotide let-7 RNA regulates developmental timing in Caenorhabditis elegans," Nature, vol. 403:901-906 (2000).
Request for Ex Parte Reexamination Transmittal Form for U.S. Pat. No. 7,732,593, pp. 1-344, dated Aug. 2, 2010.
Request for Ex Parte Reexamination Transmittal Form for U.S. Pat. No. 7,459,547, pp. 1-337, dated Jul. 30, 2010.
Request for Ex Parte Reexamination Transmittal Form for U.S. Pat. No. 7,750,144, pp. 1-220, dated Jul. 30, 2010.
Request for Ex Parte Reexamination Transmittal Form for U.S. Pat. No. 7,772,203, pp. 1-206, dated Aug. 16, 2010.
Reynolds, A. et al., "Rational siRNA design for RNA interference," Nat. Biotechnol., vol. 22(3):326-330 (2004).
Rhoades, Matthew W. et al. "Prediction of Plant MicroRNA Targets," Cell, vol. 110:513-520 (2002).
Rivas, Fabiola V. et al., "Purified Argonaute2 and an siRNA form recombinant human RISC," Nature Structural & Molecular Biology, vol. 12(4):340-349 (2005).
Rose, Scott D. et al., "Functional polarity is introduced by Dicer processing of short substrate RNAs," Nucleic Acids Research, vol. 33(13):4140-4156 (2005).
Ruvkun, Gary, "Glimpses of a Tiny RNA World," Science, vol. 294:797-799, (2001).
Sahasrabudhe, Parag V. et al., "Solution Structures of 5-Fluorouracil-Substituted RNA Duplexes Containing G-U Wobble Base Pairs," Biochemistry, vol. 36:5981-5991 (1997).
Sasaki, Takashi et al., "Identification of eight members of the Argonaute family in the human genomes," Genomics, vol. 82:323-330 (2003).
Saxena, Sandeep et al., "Small RNAs with Imperfect Match to Endogenous mRNA Repress Translation," The Journal of Biological Chemistry, vol. 278(45):44312-44319 (2003).
Scadden, A.D.J. et al., "RANi is antagonized by Ael hyper-editing," EMBO reports, vol. 2(12):1109-1111 (2001).

(56) References Cited

OTHER PUBLICATIONS

Scherer, Lisa J. et al., "Approaches for the sequence-specific knockdown of mRNA," Nature Biotechnology, vol. 21 (12):1457-1465 (2003).
Scherer, Lisa J. et al., "Rapid Assessment of Anti-HIV siRNA Efficacy Using PCR-Derived Pol III shRNA Cassettes," Molecular Therapy, vol. 10(3):597-603 (2004).
Scherer, Lisa J. et al., "Recent Applications of RNAi in Mammalian Systems," Current Pharmaceutical Biotechnology, vol. 5:355-360 (2004).
Scherer, Lisa et al., "Therapeutic Applications of RNA Interference: Recent Advances in siRNA Design," Advances in Genetics, vol. 52:1-21 (2004).
Scherr, Michaela et al., "Specific inhibition of bcr-abl gene expression by small interfering RNA," Blood, vol. 101 (4):1566-1569 (2003).
Schubert, Steffen et al., "Local RNA Target Structure Influences siRNA Efficacy: Systematic Analysis of Intentionally Designed Binding Regions," J. Mol. Biol., vol. 348:883-893 (2005).
Schwarz, Dianne S. et al., "Designing siRNA That Distinguish between Genes That Differ by a Single Nucleotide," PLoS Genetics, vol. 2(9):1-12 (2006).
Schwarz, D.S. et al., "Asymmetry in the assembly of the RNAi enzyme complex," Cell, vol. 115(2):199-208 (2003).
Schwarz, Dianne S. et al., "Evidence that siRNAs Function as Guides, Not Primers, in the Drosophila and Human RNAi Pathways," Molecular Cell, vol. 10:537-548 (2002).
Schwarz, D.S. et al., "The RNA-induced silencing complex is a Mg2+-dependent endonuclease," Curr. Biol., vol. 14 (9):787-791 (2004).
Schwarz, D.S. et al., "Why do miRNAs live in the miRNP?" Genes Dev., vol. 16(9):1025-1031 (2002).
Seggerson, Kathy et al., "Two Genetic Circuits Repress the Caenorhabditis elegans Heterochronic Gene lin-28 after Translation Initiation," Developmental Biology, vol. 243:215-225 (2002).
Semizarov, D. et al., "Specificity of short interfering RNA determined through gene expression signatures," PNAS, vol. 100(11):6347-6352 (2003).
Slack, Frank J. et al., "The lin-41 RBCC Gene Acts in the C. elegans Heterochronic Pathway between the let-7 Regulatory RNA and the LIN-29 Transcription Factor," Molecular Cell, vol. 5:659-669 (2000).
Sledz, Carol A. et al., "Activation of the interferon system by short-interfering RNAs," Nature Cell Biology, vol. 5 (9):834-838 (2003).
Smart, Nicola et al., "A rapid and sensitive assay for quantification of siRNA efficiency and specificity," Biol. Proced., vol. 7(1):1-7 (2005).
Snove, Ola Jr. et al., "Chemical Modifications Rescue Off-Target Effects of RNAi," ACS Chemical Biology, vol. 1 (5):274-276 (2006).
Song, Ji-Joon et al., "Crystal Structure of Argonaute and Its Implications for RISC Slicer Activity," Science, vol. 305:1434-1410 (2004).
Elbashir, Sayda M. et al., "RNA interference is mediated by 21- and 22-nucleotide RNAs," Genes & Development, vol. 15:188-200 (2001).
Enright, Anton J. et al., "MicroRNA targets in Drosophila," Genome Biology, vol. 5: R1.1-R1.14 (2003).
Fagard, Mathilde et al., "AG01, QDE-2, and RDE-1 are related proteins required for post-transcriptional gene silencing in plants, quelling ni fungi, and RNA interference in animals," PNAS, vol. 97(21):11650-11654 (2000).
Filipowicz, Witold, "RNAi: The Nuts and Bolts of the RISC Machine," Cell, vol. 122:17-20 (2005).
Fire, Andrew et al., "Potent and specific genetic interference by double-stranded RNA in Caenorhabditis elegans," Nature, vol. 391:806-811 (1998).
Forstemann, Klaus et al., "Drosophila microRNAs Are Sorted into Functionally Distinct Argonaute Complexes after Production by Dicer-1," Cell, vol. 130:287-297 (2007).

Further Facts and Evidence in support of Notice of Opposition to a European patent, Alnylam Pharmaceuticals, Inc., Application No. EP 04 753 972.1, dated Jul. 20, 2011.
GenBank Accession No. AAA37498, Hasel, K.W., "An endoplasmic reticulum-specific cyclophilin," Mol. Cell. Biol., vol. 11(7):3484-3491 (1991), 1 page, Apr. 27, 1993.
GenBank Accession No. AAA52150, Price, E.R. et al., "Human cyclophilin B: a second cyclophilin gene encodes a peptidyl-prolyl isomerase with a signal sequence," Proc. Natl. Acad. Sci. USA, vol. 88(5):1903-1907 (1991), 1 page, Nov. 2, 1994.
GenBank Accession No. AB451383, Goshima, N. et al., "Human Protein Factory: an infrastructure to convert the human transcriptome into the in vitro-expressed human proteome of versatile utility," 2 pages, (2008).
GenBank Accession No. NM-017748, Fabrizio, P. et al., "The evolutionary conserved core design of the catalytic activation step of the yeast spliceosome," Mol. Cell, vol. 36(4):593-608 (2009), 3 pages (2011).
GenBankAccession No. NM-021033, Yaman, E. et al., "RasGEF1A and RasGEF1B are guinine nucleotide exchange factors that discriminate between Rap GTP-binding proteins and mediate Rapt-specific nucleotide exchange," FEBS J., vol. 276(16):4607-4616 (2009), 4 pages (2011).
GenBank Accession No. XM_002272515, Predicted: Vitis vinifera phosphatidylinositide phosphatase SAC1-like (LOC100248745), mRNA, 3 pages, Dec. 7, 2011.
Gewirtz, Alan M., "On future's doorstep: RNA interference and the pharmacopeia of tomorrow," The Journal of Clinical Investigation, vol. 117(12):3612-3614 (2007).
Gong, Delquin et al, "Picking a winner: new mechanistic insights into the design of effective siRNAs," Trends in Biotechnology, vol. 22(9):451-454 (2004).
Grimm, D. et al., "Therapeutic application of RNAi: is mRNA targeting finally ready for prime time?" The Journal of Clinical Investigation, vol. 117(12):3633-3641 (2007).
Grishok, Alla et al., "Genes and Mechanisms Related to RNA Interference Regulate Expression of the Small Temporal RNAs that Control C. elegans Developmental Timing," Cell, vol. 106:23-34 (2001).
Grishok, Alla et al., "Genetic Requirements for Inheritance of RNAi in C. elegans," Science, vol. 287:2494-2497 (2000).
Grishok, Alla et al., "RNAi (Nematodes Caenorhabditis elegans)," Advances in Genetics, vol. 46:339-360 (2002).
Grosjean, Henri J. et al., "On the physical basis for ambiguity in genetic coding interactions," Proc. Natl. Acad. Sci. USA, vol. 75(2):610-614 (1978).
Grzelinski, Marius et al, "RNA Interference-Mediated Gene Silencing of Pleiotrophin Through Polyethylenimine-Complexed Small Interfering RNAs In Vivo Exerts Antitumoral Effects in Glioblastoma Xenografts," Human Gene Therapy, 17:751-766 (2006).
Ha, Iiho et al., "A bulged lin-4/lin-14 RNA duplex is sufficient for Caenorhabditis elegans lin-14 temporal gradient formation," Genes & Development, vol. 10:3041-3050 (1996).
Haley, Benjamin et al., "In vitro analysis of RNA interference in Drosophila melanogaster," Methods, vol. 30:330-336 (2003).
Haley, B. et al., "Kinetic analysis of the RNAi enzyme complex," Nat Struct Mol Biol., vol. 11(7):599-606 (2004).
Hamada, Makiko et al., "Effects on RNA Interference in Gene Expression (RNAi) in Cultured Mammalian Cells of Mismatches and the Introduction of Chemical Modifications at the 3'-Ends of siRNAs," Antisense and Nucleic Acid Drug Development, vol. 12:301-309 (2002).
Hammond, Scott M. et al., "Argonaute2, a Link Between Genetic and Biochemical Analyses of RNAi," Science, vol. 293:1146-1150 (2001).
Hammond, Scott M. et al., "Post-Transcriptional Gene Silencing by Double-Stranded RNA," Nature, vol. 2:110-119 (2001).
Hannon, Gregory J. et al. "Unlocking the potential of the human genome with RNA interference," Nature, vol. 431:371-378 (2004).
Harborth, Jens et al., "Sequence, Chemical, and Structural Variation of Small Interfering RNAs and Short Hairpin RNAs and the Effect on Mammalian Gene Silencing," Antisense and Nucleic Acid Drug Development, vol. 13:83-105 (2003).

(56) References Cited

OTHER PUBLICATIONS

Heale, Bret S.E. et al., "siRNA target site secondary structure predictions using local stable substructures," Nucleic Acids Research, vol. 33(3):1-10 (2005).

Hohjoh, Hirohiko, "Enhancement of RNAi activity by improved siRNA duplexes," FEBS Letters, vol. 557:193-198 (2004).

Hohjoh, Hirohiko et al., "RNA interference (RNAi) induction with various types of synthetic oligonucleotide duplexes in cultured human cells," FEBS Letters, vol. 521:195-199 (2002).

Holen, Torgeir et al., "Positional effects of short interfering RNAs targeting the human coagulation trigger Tissue Factor," Nucleic Acids Research, vol. 30(8):1757-1766 (2002).

Holen, T. et al., "Similar behaviour of single-strand and double-strand siRNAs suggests they act through a common RNAi pathway," Nucleic Acids Res., vol. 31(9):2401-2407 (2003).

Holen, Torgeir et al., "Tolerated wobble mutations in siRNAs decrease specificity, but can enhance activity in vivo," Nucleic Acids Research, vol. 33(15):4704-4710 (2005).

Hu-Lieskovan, Siwen et al, "Sequence-Specific Knockdown of EWS-FLI1 by Targeted, Nonrival Delivery of Small Interfering RNA Inhibits Tumor Growth in a Murine Model of Metastatic Ewing's Sarcoma," Cancer Research, 65:(19) 8984-8992 (2005).

Hutvágner, György et al., "A Cellular Function for the RNA-Interference Enzyme Dicer in the Maturation of the let-7 Small Temporal RNA," Science, vol. 293:834-838 (2001).

Hutvágner, György et al., "A microRNA in a Multiple-Turnover RNAi Enzyme Complex," Science, vol. 297:2056-2060 (2002).

Irie, Naoki et al., "Subtype- and species-specific knockdown of PKC using short interfering RNA," Biochemical and Biophysical Communications, vol. 298:738-743 (2002).

Jackson, A.L. et al., "Expression profiling reveals off-target gene regulation by RNAi," Nat. Biotechnol., vol. 21 (6):635-7 (2003).

Ketting, Rene F. et a., "A genetic link between co-suppression and RNA interference ni C. elegans," Nature, vol. 404:296-298 (2000).

KETTING et al., "Dicer functions in RNA interference and in synthesis of small RNA involved in developmental timing in C. elegans," Genes Dev., vol. 15(20):2654-2659 (2001).

Ketting, Rene F. et al., "mut-7 of C. elegans, Required for Transposon Silencing and RNA Interference, Is a Homolog of Werner Syndrome Helicase and RNaseD," Cell, vol. 99:133-141 (1999).

Khvorova, A. et al., "Functional siRNAs and miRNAs exhibit strand bias," Cell, vol. 115(2):209-216 (2003).

Kierzek, Ryszard et al., "Thermodynamics of Single Mismatches in RNA Duplexes," Biochemistry, vol. 38:14214-14223 (1999).

Kim, Daniel H. et al., "Strategies for silencing human disease using RNA interference," Nature Reviews Genetics, vol. 8:173-184 (2007).

Kim, Dong-Ho et al., "Synthetic dsRNA Dicer substrates enhances RNAi potency and efficacy," Nature Biotechnology, vol. 23(2):222-226 (2005).

Kini, Hemant K. et al., "Effect of siRNA terminal mismatches on TRBP and Dicer binding and silencing efficiacy," FEBS Journal, vol. 276:6576-6585 (2009).

Knight, Scott W. et al., "A Role for the RNase III Enzyme DCR-1 in RNA Interference and Germ Line Development in Caenorhabditis elegans," Science, vol. 293:2269-2271 (2001).

Krol, J. et al., "Structural Features of MicroRNA (miRNA) Precursors and Their Relevance to miRNA Biogenesis and Small Interfering RNA/Short Hairpin RNA Design," J. Biol. Chem., vol. 279(40):42230-42239 (2004).

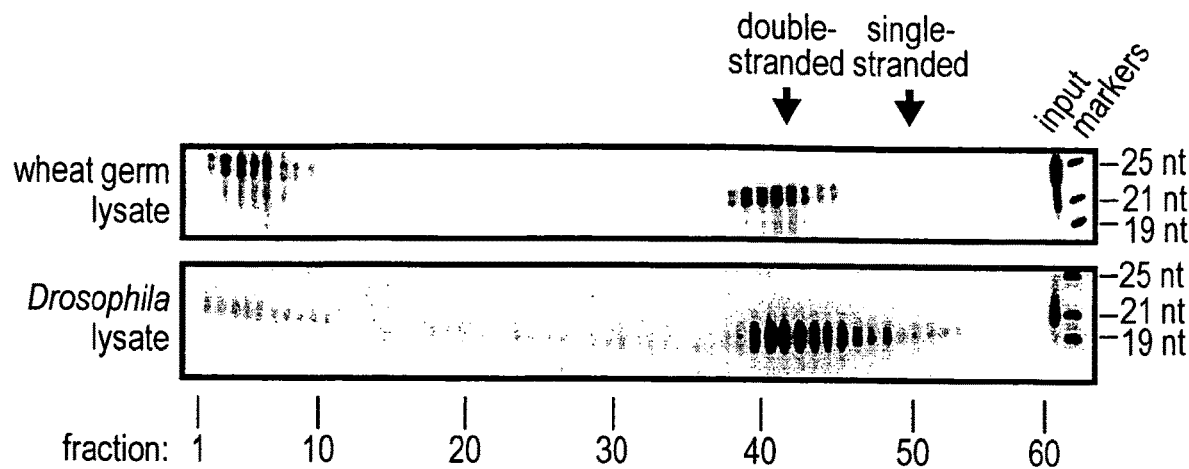
Fig. 2E
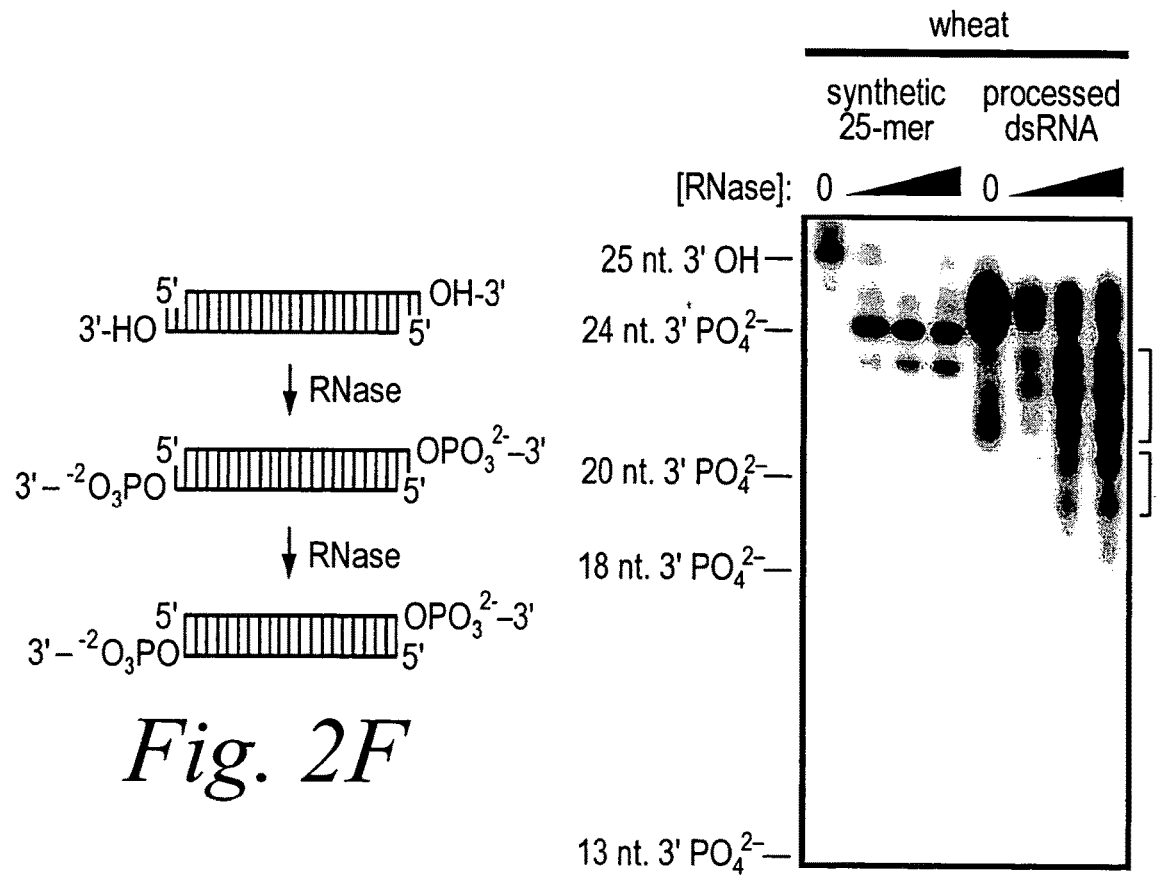
Fig. 2F
Fig. 2G

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: synthetic construct

<400> SEQUENCE: 1
uugggaugaa gccugguccg g                    21

```
<210> SEQ ID NO 2
<211> LENGTH: 21
<212> TYPE: DNA
<213> ORGANISM: Artificial Sequence
<220> FEATURE:
<223> OTHER INFORMATION: synthetic construct

<400> SEQUENCE: 2
ccggaccagg cuucauccca a                                                 21

<210> SEQ ID NO 3
<211> LENGTH: 21
<212> TYPE: DNA
<213> ORGANISM: Artificial Sequence
<220> FEATURE:
<223> OTHER INFORMATION: synthetic construct

<400> SEQUENCE: 3
ccggaucagg cuucauccca a                                                 21

<210> SEQ ID NO 4
<211> LENGTH: 21
<212> TYPE: DNA
<213> ORGANISM: Artificial Sequence
<220> FEATURE:
<223> OTHER INFORMATION: synthetic construct

<400> SEQUENCE: 4
uugggaugaa gccugauccg g                                                 21

<210> SEQ ID NO 5
<211> LENGTH: 19
<212> TYPE: DNA
<213> ORGANISM: Artificial Sequence
<220> FEATURE:
<223> OTHER INFORMATION: synthetic construct

<400> SEQUENCE: 5
cguacgcgga auacuucga                                                    19

<210> SEQ ID NO 6
<211> LENGTH: 21
<212> TYPE: DNA
<213> ORGANISM: Artificial Sequence
<220> FEATURE:
<223> OTHER INFORMATION: synthetic construct

<400> SEQUENCE: 6
ucgaaguauu ccgcguacgu g                                                 21

<210> SEQ ID NO 7
<211> LENGTH: 23
<212> TYPE: DNA
<213> ORGANISM: Artificial Sequence
<220> FEATURE:
<223> OTHER INFORMATION: synthetic construct

<400> SEQUENCE: 7
aucacguacg cggaauacuu cga                                               23

<210> SEQ ID NO 8
<211> LENGTH: 25
<212> TYPE: DNA
<213> ORGANISM: Artificial Sequence
<220> FEATURE:
<223> OTHER INFORMATION: synthetic construct
```

<400> SEQUENCE: 8
ucgaaguauu ccgcguacgu gauug                                    25

<210> SEQ ID NO 9
<211> LENGTH: 40
<212> TYPE: DNA
<213> ORGANISM: Artificial Sequence
<220> FEATURE:
<223> OTHER INFORMATION: synthetic construct

<400> SEQUENCE: 9
gcgtaatacg actcactata ggcgccggaa caagttgaag                    40

<210> SEQ ID NO 10
<211> LENGTH: 21
<212> TYPE: DNA
<213> ORGANISM: Artificial Sequence
<220> FEATURE:
<223> OTHER INFORMATION: synthetic construct

<400> SEQUENCE: 10
gacagtcacg gaaccaagat g                                        21

<210> SEQ ID NO 11
<211> LENGTH: 42
<212> TYPE: DNA
<213> ORGANISM: Artificial Sequence
<220> FEATURE:
<223> OTHER INFORMATION: synthetic construct

<400> SEQUENCE: 11
gcgtaatacg actcactata ggtgagtctg tggtcgtgag tg                 42

<210> SEQ ID NO 12
<211> LENGTH: 21
<212> TYPE: DNA
<213> ORGANISM: Artificial Sequence
<220> FEATURE:
<223> OTHER INFORMATION: synthetic construct

<400> SEQUENCE: 12
gctgctgcta aagtcgtagg a                                        21

<210> SEQ ID NO 13
<211> LENGTH: 59
<212> TYPE: DNA
<213> ORGANISM: Artificial Sequence
<220> FEATURE:
<223> OTHER INFORMATION: synthetic construct

<400> SEQUENCE: 13
ccactgcagt tgcgtgaaac agctacgata ccaatagaat ccggatcagg cttcatccc    59

<210> SEQ ID NO 14
<211> LENGTH: 115
<212> TYPE: DNA
<213> ORGANISM: Artificial Sequence
<220> FEATURE:
<223> OTHER INFORMATION: synthetic construct

<400> SEQUENCE: 14
gacagtcacg gaaccaagat ggacgatctt tgaggatttc agcgaccttc atgggttcta    60
aactcacgag gccacaggca cgtgctgcta ttccactgca gttgcgtgaa acagc        115

```
<210> SEQ ID NO 15
<211> LENGTH: 21
<212> TYPE: DNA
<213> ORGANISM: Artificial Sequence
<220> FEATURE:
<223> OTHER INFORMATION: synthetic construct

<400> SEQUENCE: 15
ucggaccagg cuucauccccc c                                             21

<210> SEQ ID NO 16
<211> LENGTH: 21
<212> TYPE: DNA
<213> ORGANISM: Artificial Sequence
<220> FEATURE:
<223> OTHER INFORMATION: synthetic construct

<400> SEQUENCE: 16
gggaugaagc cugguccgag g                                              21

<210> SEQ ID NO 17
<211> LENGTH: 21
<212> TYPE: DNA
<213> ORGANISM: Artificial Sequence
<220> FEATURE:
<223> OTHER INFORMATION: synthetic construct

<400> SEQUENCE: 17
ucggaccagg cuucauuccc c                                              21

<210> SEQ ID NO 18
<211> LENGTH: 21
<212> TYPE: DNA
<213> ORGANISM: Artificial Sequence
<220> FEATURE:
<223> OTHER INFORMATION: synthetic construct

<400> SEQUENCE: 18
ggaaugaagc cugguccgag a                                              21

<210> SEQ ID NO 19
<211> LENGTH: 21
<212> TYPE: DNA
<213> ORGANISM: Artificial Sequence
<220> FEATURE:
<223> OTHER INFORMATION: synthetic construct

<400> SEQUENCE: 19
ccggaccagg cuucaucccca a                                             21

<210> SEQ ID NO 20
<211> LENGTH: 21
<212> TYPE: DNA
<213> ORGANISM: Artificial Sequence
<220> FEATURE:
<223> OTHER INFORMATION: synthetic construct

<400> SEQUENCE: 20
gggaugaagc cugguccgga u                                              21

<210> SEQ ID NO 21
<211> LENGTH: 21
<212> TYPE: DNA
<213> ORGANISM: Artificial Sequence
<220> FEATURE:
<223> OTHER INFORMATION: synthetic construct
```

```
<400> SEQUENCE: 21
ccggaucagg cuucauccca a                                              21

<210> SEQ ID NO 22
<211> LENGTH: 21
<212> TYPE: DNA
<213> ORGANISM: Artificial Sequence
<220> FEATURE:
<223> OTHER INFORMATION: synthetic construct

<400> SEQUENCE: 22
gggaugaagc cugauccgga u                                              21

<210> SEQ ID NO 23
<211> LENGTH: 21
<212> TYPE: DNA
<213> ORGANISM: Artificial Sequence
<220> FEATURE:
<221> NAME/KEY: n
<222> LOCATION: 20
<223> OTHER INFORMATION: synthetic construct, n=5-iodo-u

<400> SEQUENCE: 23
cguacgcgga auacuucgan u                                              21

<210> SEQ ID NO 24
<211> LENGTH: 25
<212> TYPE: DNA
<213> ORGANISM: Artificial Sequence
<220> FEATURE:
<221> NAME/KEY: n
<222> LOCATION: 24
<223> OTHER INFORMATION: synthetic construct, n=5-iodo-u

<400> SEQUENCE: 24
aucacguacg cggaauacuu cganu                                          25
```

METHODS AND COMPOSITIONS FOR CONTROLLING EFFICACY OF RNA SILENCING

SEQUENCE LISTING

The instant application contains a Sequence Listing which has been submitted electronically in ASCII format and is hereby incorporated by reference in its entirety. Said ASCII copy, created on Apr. 4, 2022, is named 613631 UMY-050CON4_SQL.txt and is 4.9 KB in size.

RELATED APPLICATIONS

This application is a continuation of U.S. patent application Ser. No. 13/917,480, filed Jun. 13, 2013, which is a continuation of U.S. patent application Ser. No. 12/802,534, filed Jun. 7, 2010, which is a continuation of U.S. patent application Ser. No. 12/139,072, filed Jun. 13, 2008 (now U.S. Pat. No. 7,732,593), which is a continuation of U.S. patent application Ser. No. 10/859,337, filed Jun. 2, 2004 (now U.S. Pat. No. 7,459,547), which claims the benefit of U.S. Provisional Patent Application Ser. No. 60/475,386, filed Jun. 2, 2003.

U.S. patent application Ser. No. 13/917,480 is also a continuation of U.S. patent application Ser. No. 12/802,536 filed Jun. 7, 2010, which is a divisional of Ser. No. 12/172,938, filed Jul. 14, 2008 (now U.S. Pat. No. 7,772,203), which is a divisional of U.S. patent application Ser. No. 10/859,337, filed Jun. 2, 2004 (now U.S. Pat. No. 7,459,547), which claims the benefit of U.S. Provisional Patent Application Ser. No. 60/475,386, filed Jun. 2, 2003.

The entire disclosures of each of these patents and patent applications are incorporated herein by reference in their entireties.

STATEMENT REGARDING FEDERALLY SPONSORED RESEARCH OR DEVELOPMENT

This invention was made with government support under Grant Nos. GM062862, GM065236, and GM05880 awarded by the National Institutes of Health. The government has certain rights in the invention.

BACKGROUND OF THE INVENTION

RNA interference (RNAi) in animals and basal eukaryotes, quelling in fungi, and posttranscriptional gene silencing (PTGS) in plants are examples of a broad family of phenomena collectively called RNA silencing (Kooter et al. 1999; Li and Ding 2001; Matzke et al. 2001; Vaucheret et al. 2001; Waterhouse et al. 2001; Hannon 2002; Plasterk 2002). The unifying features of RNA silencing phenomena are the production of small (21-26 nt) RNAs that act as specificity determinants for down-regulating gene expression (Hamilton and Baulcombe 1999; Hammond et al. 2000; Parrish et al. 2000; Zamore et al. 2000; Djikeng et al. 2001; Parrish and Fire 2001; Tijsterman et al. 2002) and the requirement for one or more members of the Argonaute family of proteins (or PPD proteins, named for their characteristic PAZ and Piwi domains) (Tabara et al. 1999; Fagard et al. 2000; Hammond et al. 2001; Hutvagner and Zamore 2002; Kennerdell et al. 2002; Martinez et al. 2002a; Pal-Bhadra et al. 2002; Williams and Rubin 2002).

Small RNAs are generated in animals by members of the Dicer family of double-stranded RNA (dsRNA)-specific endonucleases (Bernstein et al. 2001; Billy et al. 2001; Grishok et al. 2001; Ketting et al. 2001). Dicer family members are large, multidomain proteins that contain putative RNA helicase, PAZ, two tandem ribonuclease III (RNase III), and one or two dsRNA-binding domains. The tandem RNase III domains are believed to mediate endonucleolytic cleavage of dsRNA into small interfering RNAs (siRNAs), the mediators of RNAi. In *Drosophila* and mammals, siRNAs, together with one or more Argonaute proteins, form a protein-RNA complex, the RNA-induced silencing complex (RISC), which mediates the cleavage of target RNAs at sequences with extensive complementarity to the siRNA (Hammond et al. 2000, 2001; Zamore et al. 2000; Elbashir et al. 2001a,b,c; Nykänen et al. 2001; Hutvagner and Zamore 2002; Martinez et al. 2002a).

In addition to Dicer and Argonaute proteins, RNA-dependent RNA polymerase (RdRP) genes are required for RNA silencing in *Caenorhabditis elegans* (Smardon et al. 2000; Sijen et al. 2001), *Neurospora crassa* (Cogoni and Macino 1999), and Dictyostelium discoideum (Martens et al. 2002), but likely not for RNAi in *Drosophila* or mammals (Celotto and Graveley 2002; Chiu and Rana 2002; Holen et al. 2002; Martinez et al. 2002b; Schwarz et al. 2002; Roignant et al. 2003). In plants, PTGS initiated by transgenes that overexpress an endogenous mRNA also requires a putative RdRP, SGS2 (SDE1; Dalmay et al. 2000; Mourrain et al. 2000), although transgenes designed to generate dsRNA bypass this requirement (Beclin et al. 2002). Similarly, silencing induced by viruses replicating through a dsRNA intermediate (virus-induced gene silencing, VIGS) does not require SGS2 (Dalmay et al. 2000).

Dicer in animals and CARPEL FACTORY (CAF, a Dicer homolog) in plants also generate microRNAs (miRNAs), 20-24-nt, single-stranded noncoding RNAs thought to regulate endogenous mRNA expression (Lee et al. 1993; Reinhart et al. 2000, 2002; Grishok et al. 2001; Hutvagner et al. 2001; Ketting et al. 2001; Lagos-Quintana et al. 2001, 2002; Lau et al. 2001; Lee and Ambros 2001; Mourelatos et al. 2002; Park et al. 2002). miRNAs are produced by Dicer cleavage of stem-loop precursor RNA transcripts (pre-miRNAs); the miRNA can reside on either the 5' or 3' side of the double-stranded stem (Lee et al. 1993; Pasquinelli et al. 2000; Lagos-Quintana et al. 2001; Lau et al. 2001; Lee and Ambros 2001). In animals, pre-miRNAs are transcribed as longer primary transcripts (pri-miRNAs) that are processed in the nucleus into compact, folded structures (pre-miRNAs), then exported to the cytoplasm, where they are cleaved by Dicer to yield mature miRNAs (Lee et al. 2002). Animal miRNAs are only partially complementary to their target mRNAs; this partial complementarity has been proposed to cause miRNAs to repress translation of their targets, rather than direct target cleavage by the RNAi pathway (for review, see Ruvkun 2001; Hutvágner and Zamore 2002). Plant miRNAs have far greater complementarity to cellular mRNAs and have been proposed to mediate target RNA cleavage via an RNAi-like mechanism (Llave et al. 2002b; Rhoades et al. 2002).

SUMMARY OF THE INVENTION

The present invention is based, at least in part, on the finding that extracts of wheat germ recapitulate many of the key features of RNA silencing in plants. Using this in vitro system, it is shown that in plants, ATP-dependent, Dicer-like enzymes cleave dsRNA into small RNAs that have the structure of siRNAs. Unlike *Drosophila* embryos or mammalian cells, plants convert dsRNA into two distinct classes of siRNAs, long and short siRNAs. Inhibitor studies indicate that a different Dicer-like enzyme generates each siRNA class. Furthermore, a wheat RdRP activity can synthesize dsRNA using exogenous single-stranded RNA as a template without an exogenous primer, and that this dsRNA is preferentially converted into long siRNAs.

Wheat germ extracts also contain an endogenous RISC programmed with a miRNA which can direct efficient cleavage of the wild-type *Arabidopsis* PHAVOLUTA (PHV) mRNA sequence, but not that of a previously described dominant PHV mutant. Interestingly, exact complementarity between the miRNA and target mRNA is not necessary for the miRNA to direct efficient target cleavage. An siRNA containing three mismatches with its target mRNA, was found to be at least as potent as an siRNA with perfect complementarity to the same target sequence, demonstrating that mismatches per se do not block target cleavage. Rather, the specific position and sequence of siRNA:target RNA mismatches determine if they permit or disrupt RNAi. It is proposed that three or four mismatches between an miRNA (or the guide strand of an siRNA duplex) and its target RNA, properly placed so as to still permit mRNA cleavage, facilitates the release of cleaved target RNA from the RISC complex, thereby increasing the rate of enzyme turnover. In particular, the efficiency of cleavage is greater when a G:U base pair, referred to also as a G:U wobble, is present near the 5' or 3' end of the complex formed between the miRNA and the target. Understanding the natural mechanism by which miRNAs efficiency mediate RNAi in plants allows for the design of improved RNAi agents for use in mediating RNAi not only in plants, but in eukaryotes (in particular, in mammals).

Accordingly, the present invention features methods of enhancing the efficacy of an RNAi agent comprising substituting a at least one terminal nucleotide with a nucleotide that does not form a Watson-Crick base pair with the corresponding nucleotide in a target mRNA. The invention also provides compositions comprising RNAi agents, e.g., siRNAs, pre-miRNA, shRNAs, having nucleotide substitutions for enhanced efficacy of RNAi, as well as vectors, transgenes and cells comprising the RNAi agents. Further featured is a Dicer-like enzyme, an extract comprising the enzyme, and methods for their use. Kits for use in mediating RNAi comprising the compositions of the invention are provided. Therapeutic methods and pharmaceutical compositions are also provided.

Other features and advantages of the invention will be apparent from the following detailed description and claims.

BRIEF DESCRIPTION OF THE DRAWINGS

(FIG. 1A) Size distribution of small RNA clones. (FIG. 1B) Sequence composition of the 5' ends of cloned small RNA as a function of length.

FIGS. 2A-2G. dsRNA is cleaved into two discrete classes of bona fide siRNAs in plant extracts. (FIG. 2A) Upon incubation in wheat germ extract, 32P-dsRNA was cleaved into small RNAs in a highly processive reaction, as in fly embryo lysate. (FIG. 2B) 32P-dsRNA was cleaved in wheat germ extract into two sizes of small RNAs, ~21-nt and 24-25-nt long, relative to synthetic 5'-32P-radiolabeled RNA markers. (FIG. 2C) 32P-dsRNA was cleaved in cauliflower extract into two sizes of small RNAs. (FIG. 2D) Efficient production of small RNAs in wheat germ extract required ATP. ATP, creatine phosphate, and creatine kinase were included (+ATP) or omitted ([−] ATP) from the reaction. (FIG. 2E) Small RNAs produced in vitro in wheat germ extract are double-stranded. 32P-dsRNA was incubated in wheat germ extract or *Drosophila* embryo lysate, deproteinized at room temperature without organic extraction, then analyzed by gel filtration on a Superdex 200 HR column. The peak positions of double- and single-stranded synthetic siRNA standards are indicated. (FIG. 2F) Scheme for detecting 3' overhanging ends on small RNAs by nuclease protection. (FIG. 2G) Small RNAs produced by incubation of 32P-dsRNA in wheat germ extract have ~2-nt 3' overhanging ends and a central double-stranded body, characteristics of the products of Dicer cleavage. Brackets indicate the nuclease digestion products. The positions of 5'-32P-radiolabeled size markers are indicated at left. 3'-phosphorylated markers were generated by reacting synthetic RNAs one base longer than indicated with periodate, followed by [beta]-elimination, yielding an RNA one base shorter, but bearing a 3'-phosphate in place of a hydroxyl.

(FIG. 3A, FIG. 3B) 32P-dsRNA was incubated in either *Drosophila* embryo lysate or wheat germ extract for 3 hours in the presence of increasing concentrations of 21-nt or 25-nt siRNA duplexes, then analyzed by denaturing gel electrophoresis and quantified. The siRNA concentration is presented in micromoles nucleotide per liter to permit comparison of the different lengths of siRNA duplex used. The relative efficiency of the reactions was determined by fitting the data to a single exponential and comparing the rate constant. (FIG. 3A) 21-nt siRNA duplexes (filled circles) are more efficient inhibitors of *Drosophila* Dicer than 25-nt siRNA duplexes (open circles). (FIG. 3B) Production of 25-nt siRNAs in wheat germ extract (squares) was inhibited more efficiently by a 25-nt synthetic siRNA duplex (red symbols) than by a 21-nt siRNA duplex (black symbols), but production of the 21-nt siRNAs (circles) was not inhibited by either synthetic siRNA duplex. (FIG. 3C) dsRNA competitor inhibited the production of both 25-nt (black squares) and 21-nt (red circles) siRNAs in wheat germ extract. Production of siRNAs in *Drosophila* embryo lysate (blue circles) was also inhibited by dsRNA competitor, but to a lower extent, perhaps reflecting a higher concentration of Dicer in *Drosophila* embryo lysate than in wheat germ extract.

(FIG. 5A) Wheat germ extract, but not *Drosophila* embryo lysate, contains an RdRP activity that can extend a primer. The arrowhead indicates the primer extension product produced when an antisense 21-nt RNA primer, but not a sense primer, was incubated in the wheat germ extract with a 592-nt single-stranded RNA. The primers correspond to nucleotides 511-532 of the RNA template. (FIG. 5B) RdRP-dependent production of small RNAs in wheat germ extract. Increasing concentrations of a 2.7-kb *Photinus pyralis* (Pp) luciferase mRNA triggered production of 32P-radiolabeled small RNAs in wheat germ extract when ribonucleotide triphosphates (including α-32P-UTP), but not when 3'-deoxy GTP and 3'-deoxy CTP were included in the reaction. (FIG. 5C) Production of newly synthesized small RNAs was more efficiently inhibited by a 25-nt synthetic siRNA duplex (open circles) than by a 21-nt synthetic siRNA duplex (open squares).

(FIG. 6A) A wheat ortholog of miR165 or miR166 is present in wheat germ extract. Quantitative Northern hybridization analysis using synthetic miR165 RNA concentration standards, antisense miR165 RNA, and total RNA prepared from 30 μL of wheat germ extract or *Drosophila* embryo lysate. (FIG. 6B) Quantitation of the data in A. Closed circles, synthetic miR165 standards; open circle, RNA extracted from 30 μL of wheat germ extract. The line shows a linear fit of the four highest concentration standards. (FIG. 6C) Schematic of the RNA targets, indicating the sequences of the miR165/166-complementary regions of wild-type PHV and mutant phv mRNAs, miR165, miR166, and the siRNA antisense strands used in FIG. 7C.

(FIG. 7A) When incubated in wheat germ extract, 5'-radiolabeled target RNA containing wild-type PHV sequences was cleaved within the PHV sequences complementary to miR165 and miR166. In contrast, a dominant G→A mutant target RNA was cleaved inefficiently. (FIG. 7B) Quantification of the data in A. (Circles) Wild-type PHV sequences; (squares) mutant sequences; (filled symbols) full-length target RNA; (open symbols) 5' cleavage product. The difference in cleavage rates is ~14-fold. (FIG. 7C) Analysis of PHV cleavage in an in vitro RNAi reaction programmed with siRNA duplexes and *Drosophila* embryo lysate. The identity of the antisense strand of the siRNA duplex and the RNA target used is indicated above the gel and described in FIG. 6C.

DETAILED DESCRIPTION OF THE INVENTION

Figure 1A:
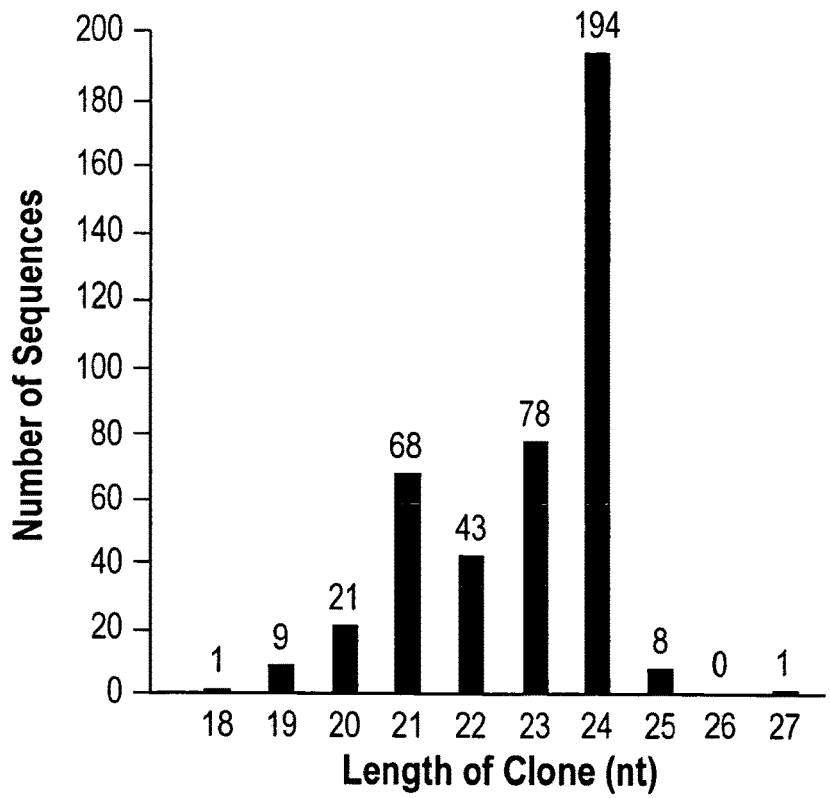
FIGS. 1A-1B. *Arabidopsis thaliana* small RNAs form two distinct size classes.

The present invention is based, at least in part, on the discovery that extracts of wheat germ, introduced for the study of translation and protein translocation in the 1970s (Roberts and Paterson 1973), recapitulate many of the key features of RNA silencing in plants. Using this in vitro system, the instant inventors have shown that in plants, ATP-dependent, Dicer-like enzymes cleave dsRNA into small RNAs that have the structure of siRNAs. Unlike *Drosophila* embryos or mammalian cells, plants convert dsRNA into two distinct classes of siRNAs, long (e.g., 21-22 nucleotides) and short (e.g., 24-25 nucleotides) siRNAs. Inhibitor studies indicate that a second Dicer-like enzyme functions in plants to generate each siRNA class. The instant inventors have also shown that a wheat RdRP activity can synthesize dsRNA using exogenous single-stranded RNA as a template without an exogenous primer, and that this dsRNA is preferentially converted into long siRNAs.

Finally, it is demonstrated that wheat germ extracts contain an endogenous RISC programmed with a miRNA. This endogenous miRNA complex has sufficient sequence information to direct efficient cleavage of the wild-type *Arabidopsis* PHA VOLUTA (PHV) mRNA sequence, but not that of a previously described dominant PHV mutant that perturbs leaf development. Based on an understanding of the mechanism by which miRNAs direct RNAi in plants, new siRNAs can be designed for regulating RNAi in plants. More importantly, siRNAs can be designed, for example, based on the sequence of various eukaryotic miRNAs, such siRNAs having utility in mediating RNAi in mammals, and particularly, in humans.

Accordingly, in one aspect, the instant invention provides a method of enhancing the efficacy of an RNAi agent, involving substituting at least one terminal nucleotide of the RNAi agent with a nucleotide which does not form a Watson-Crick base pair with the corresponding nucleotide in a target mRNA, such that efficacy is enhanced.

In one embodiment, the substituted nucleotide forms a G:U wobble base pair with the target mRNA. In one preferred embodiment, the substitution is an A→G substitution, the G forming a G:U wobble base pair with a U in the corresponding target mRNA. In another preferred embodiment, the substitution is a C→U substitution, the U forming a G:U wobble base pair with a G in the corresponding target mRNA.

In one embodiment, the terminal nucleotide is within 5 or fewer nucleotides from the 5' end of the RNAi agent. In a related embodiment, the terminal nucleotide is within 5 or fewer nucleotides from the 3' end of the RNAi agent.

In one embodiment, at least two terminal nucleotides are substituted. In preferred embodiments, the two nucleotides substituted are at the 5' end of the RNAi agent or at the 3' end of the RNAi agent. In another preferred embodiment, a first terminal nucleotide substituted is at the 5' end of the RNAi agent and a second terminal nucleotide substituted is at the 3' end of the RNAi agent.

In one embodiment, at least three, four or five terminal nucleotides are substituted.

In another aspect, the instant invention provides a RNAi agent having at least one terminal nucleotide of the RNAi agent substituted with a nucleotide which forms a G:U wobble base pair with the corresponding nucleotide in a target mRNA.

In one embodiment of this aspect of the invention, the substitution is an A→G substitution, the G forming a G:U wobble base pair with a U in the corresponding target mRNA. In another embodiment, the substitution is a C→U substitution, the U forming a G:U wobble base pair with a G in the corresponding target mRNA.

In other embodiments, the terminal nucleotide is within 5 or fewer nucleotides from the 5' end of the RNAi agent or from the 3' end of the RNAi agent.

In yet other embodiments, at least two terminal nucleotides are substituted. In preferred embodiments, the two terminal nucleotides substituted are at the 5' end of the RNAi agent or at the 3' end of the RNAi agent. In other preferred embodiments, a first terminal nucleotide substituted is at the 5' end of the RNAi agent and a second terminal nucleotide substituted is at the 3' end of the RNAi agent.

In other embodiments, at least three, four or five terminal nucleotides are substituted.

In various embodiments of this aspect of the invention, the RNAi agent is chemically synthesized, enzymatically synthesized, or derived from an engineered precursor.

In another aspect, the instant invention provides a method of enhancing silencing of a target mRNA, comprising contacting a cell having an RNAi pathway with the RNAi agent of any one of the preceding claims under conditions such that silencing is enhanced.

In yet another aspect, the instant invention provides a method of enhancing silencing of a target mRNA in a subject, comprising administering to the subject a pharmaceutical composition comprising the RNAi agent of any one of the preceding claims such that silencing is enhanced.

In certain embodiments of the invention, compositions are provided comprising the RNAi agents of the invention formulated to facilitate entry of the agent into a cell. Pharmaceutical compositions comprising the RNAi agents of the invention are also provided.

In other embodiments, the instant invention provides engineered pre-miRNA comprising the RNAi agent of any one of the preceding claims, and vectors encoding the pre-miRNA.

In related embodiments, the instant invention provides a pri-miRNA comprising the pre-miRNA of the invention, and a vector encoding the pri-miRNA.

In yet other embodiments, the invention provides a small hairpin RNA (shRNA) comprising nucleotide sequence identical to any of the RNAi agents of the instant invention, a vector encoding the shRNA, and a transgene encoding the shRNA.

The instant invention further provides a cell, e.g., a mammalian cell, preferably a human cell, comprising the vectors of the invention. 35.

In another aspect, the instant invention provides an isolated *Arabidopsis thaliana* Dicer-like enzyme capable of cleaving a long dsRNA substrate into short, 24-25 nucleotide dsRNA products, the activity of said enzyme being inhibited in the presence of said dsRNA products. In a related aspect, the instant invention provides a method of generating a RNAi agent 24-25 nucleotides in length, comprising incubating a dsRNA substrate with the enzyme of the invention, such that the agent is generated. Also provided is an *Arabidopsis thaliana* cell-free extract comprising the enzyme of the invention. In a related aspect, a method is provided of generating a RNAi agent 24-25 nucleotides in length, comprising incubating a dsRNA substrate with the extract of the invention, such that the agent is generated.

In a certain embodiment of the instant invention, a kit is provided for use in mediating RNAi, comprising the enzyme or the extract of the invention, and instructions for use.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, an siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising ~21 nucleotides (or nucleotide analogs), for example, 19, 20, 21 or 22 nucleotides. The term "long" siRNA refers to a siRNA comprising ~24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; 0- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2):117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phophoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

A RNAi agent having a strand which is "sequence sufficiently complementary to a target mRNA sequence to direct target-specific RNA interference (RNAi)" means that the strand has a sequence sufficient to trigger the destruction of the target mRNA by the RNAi machinery or process.

The term "phosphorylated" means that at least one phosphate group is attached to a chemical (e.g., organic) compound. Phosphate groups can be attached, for example, to proteins or to sugar moieties via the following reaction: free hydroxyl group+phosphate donor→phosphate ester linkage. The term "5' phosphorylated" is used to describe, for example, polynucleotides or oligonucleotides having a phosphate group attached via ester linkage to the C5 hydroxyl of the 5' sugar (e.g., the 5' ribose or deoxyribose, or an analog of same). Mono-, di-, and triphosphates are common. Also intended to be included within the scope of the instant invention are phosphate group analogs which function in the same or similar manner as the mono-, di-, or triphosphate groups found in nature (see e.g., exemplified analogs.)

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected micleic acid sequence, all operably linked to the selected sequence, and may include an enhancer sequence.

A gene "involved" in a disorder includes a gene, the normal or aberrant expression or function of which effects or causes a disease or disorder or at least one symptom of said disease or disorder The phrase "examining the function of a gene in a cell or organism" refers to examining or studying the expression, activity, function or phenotype arising therefrom.

Various methodologies of the instant invention include step that involves comparing a value, level, feature, characteristic, property, etc., to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc., determined prior to performing an RNAi methodology, as described herein. For example, a transcription rate, mRNA level, translation rate, protein level, biological activity, cellular characteristic or property, genotype, phenotype, etc., can be determined prior to introducing a RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. RNA Molecules

The present invention features "RNAi agents", methods of making said RNAi agents and methods (e.g., research and/or therapeutic methods) for using said RNAi agents. The RNAi agents can be siRNA molecules, precursor molecules (e.g., engineered precursor molecules) that are processed into siRNA molecules, or molecules (e.g., DNA molecules) that encode, for example, precursor molecules (e.g., engineered precursor molecules)

Exemplary siRNA molecules have a length from about 10-50 or more nucleotides. Preferably, siRNA molecule has a length from about 15-45 or 15-30 nucleotides. More preferably, the siRNA molecule has a length from about 16-25 or 18-23 nucleotides. The siRNA molecules of the invention further comprise at least one strand that has a sequence that is "sufficiently complementary" to a target mRNA sequence to direct target-specific RNA interference (RNAi), as defined herein, i.e., the strand has a sequence sufficient to trigger the destruction of the target mRNA by the RNAi machinery or process. Such a strand can be referred to as an antisense strand in the context of a ds-siRNA molecule. The siRNA molecule can be designed such that every residue is complementary to a residue in the target molecule. Preferably, however, the siRNA molecule is designed such that modified base pairing, in particular, G:U base pairing (i.e., G:U "wobble" base pairing) occurs between the strand of the siRNA molecule mediating RNAi and the target mRNA.

In further embodiments, substitutions can be made within the molecule to increase stability and/or enhance processing activity of said molecule. Substitutions can be made within the strand or can be made to residues a the ends of the strand. Preferably, however, substitutions are not made in the central portion of the strand as the sequence of this portion of the strand has been determined to be essential to effecting cleavage of the corresponding target mRNA. The 5'-terminus is, most preferably, phosphorylated (i.e., comprises a phosphate, diphosphate, or triphosphate group). The 3' end of an siRNA can be a hydroxyl group although there is no requirement for a 3' hydroxyl group when the active agent is a ss-siRNA molecule.

The target RNA cleavage reaction guided by siRNAs is highly sequence specific. In general, siRNA containing a nucleotide sequences identical to a portion of the target gene are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of a siRNA contribute equally to target recognition. Mismatches in the center of the siRNA are most critical and essentially abolish target RNA cleavage. In contrast, the 3' nucleotides of the siRNA do not contribute significantly to specificity of the target recognition. In particular, residues 3' of the siRNA sequence which is complementary to the target RNA (e.g., the guide sequence) are not critical for target RNA cleavage.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=#of identical positions/total #of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between a strand of the RNAi agent and the portion of the target gene is preferred. Alternatively, the RNAi agent may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(#of A+T bases)+4(#of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

In a preferred aspect, the RNA molecules of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the RNA agents in tissue culture medium.

In an especially preferred embodiment of the present invention the RNA molecule may contain at least one modified nucleotide analogue. The nucleotide analogues may be located at positions where the target-specific activity, e.g., the RNAi mediating activity, is not substantially effected, e.g., in a region at the 5'-end and/or the 3'-end of the RNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH- group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine are suitable. It should be noted that the above modifications may be combined.

RNA may be produced enzymatically or by partial/total organic synthesis, any modified nibonucleotide can be introduced by in vitro enzymatic or organic synthesis. In one embodiment, a RNAi agent is prepared chemically. Methods of synthesizing RNA molecules are known in the art, in particular, the chemical synthesis methods as de scribed in Verma and Eckstein (1998) *Annul Rev. Biochem.* 67:99-134. In another embodiment, a RNAi agent is prepared enzymatically. For example, a ds-siRNA can be prepared by enzymatic processing of a long ds RNA having sufficient complementarity to the desired target mRNA. Processing of long ds RNA can be accomplished in vitro, for example, using appropriate cellular lysates and ds-siRNAs can be subsequently purified by gel electrophoresis or gel filtration. ds-siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

In one embodiment, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In a preferred aspect of the invention, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e., a protein present in the genome of a cell or organism). In another embodiment, the target mRNA molecule of the invention specified the amino acid sequence of a heterologous protein expressed in a recombinant cell or a genetically altered organism. In another embodiment, the target mRNA molecule of the invention specified the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

In one embodiment, RNAi agents are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNAi agent. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses an RNAi agent from a recombinant construct may be produced by introducing the construct into a zygote, an embryonic stem cell, or another multipotent cell derived from the appropriate organism.

II. Short hairpin RNAs (shRNAs)

In certain featured embodiments, the instant invention features shRNAs which can be processed into siRNAs, for example, by a cell's endogenous RNAi machinery. In contrast to short siRNA duplexes, short hairpin RNAs (shRNAs) mimics the natural precursors of miRNAs and enters at the top of the RNAi pathway. For this reason, shRNAs are believed to mediate RNAi more efficiently by being fed through the entire natural RNAi pathway.

1. Engineered RNA Precursors that Generate siRNAs

Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired siRNAs.

In shRNAs, or engineered precursor RNAs, of the instant invention, one portion of the duplex stem is a nucleic acid sequence that is complementary (or anti-sense) to the target mRNA. Thus, engineered RNA precursors include a duplex stem with two portions and a loop connecting the two stem portions. The two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 micleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

shRNAs of the invention include the sequences of the desired siRNA duplex. The desired siRNA duplex, and thus both of the two stem portions in the engineered RNA precursor, are selected by methods known in the art. These include, but are not limited to, selecting an 18, 19, 20, 21 nucleotide, or longer, sequence from the target gene mRNA sequence from a region 100 to 200 or 300 nucleotides on the 3' side of the start of translation. In general, the sequence can be selected from any portion of the mRNA from the target gene, such as the 5' UTR (untranslated region), coding sequence, or 3' UTR. This sequence can optionally follow immediately after a region of the target gene containing two adjacent AA nucleotides. The last two nucleotides of the 21 or so nucleotide sequence can be selected to be UU (so that the anti-sense strand of the siRNA begins with UU). This 21 or so nucleotide sequence is used to create one portion of a duplex stem in the engineered RNA precursor. This sequence can replace a stem portion of a wild-type pre-stRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-stRNA.

Engineered RNA precursors include in the duplex stem the 21-22 or so nucleotide sequences of the siRNA desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor, and to maximize the efficacy of the resulting siRNA in targeting the corresponding mRNA for destruction by RNAi in vivo and in vitro.

Another defining feature of these engineered RNA precursors is that as a consequence of their length, sequence, and/or structure, they do not induce sequence non-specific responses, such as induction of the interferon response or apoptosis, or that they induce a lower level of such sequence non-specific responses than long, double-stranded RNA (>150 bp) that has been used to induce RNAi. For example, the interferon response is triggered by dsRNA longer than 30 base pairs.

2. Transgenes Encoding Engineered RNA Precursors

The new engineered RNA precursors can be synthesized by standard methods known in the art, e.g., by use of an automated DNA synthesizer (such as are commercially available from Biosearch, Applied Biosystems, etc.). These synthetic, engineered RNA precursors can be used directly as described below or cloned into expression vectors by methods known in the field. The engineered RNA precursors should be delivered to cells in vitro or in vivo in which it is desired to target a specific mRNA for destruction. A number of methods have been developed for delivering DNA or RNA to cells. For example, for in vivo delivery, molecules can be injected directly into a tissue site or administered systemically. In vitro delivery includes methods known in the art such as electroporation and lipofection.

To achieve intracellular concentrations of the nucleic acid molecule sufficient to suppress expression of endogenous mRNAs, one can use, for example, a recombinant DNA construct in which the oligonucleotide is placed under the control of a strong Pol III (e.g., U6 or Pol III H1-RNA promoter) or Pol II promoter. The use of such a construct to transfect target cells in vitro or in vivo will result in the transcription of sufficient amounts of the engineered RNA precursor to lead to the production of an siRNA that can target a corresponding mRNA sequence for cleavage by RNAi to decrease the expression of the gene encoding that mRNA. For example, a vector can be introduced in vivo such that it is taken up by a cell and directs the transcription of an engineered RNA precursor. Such a vector can remain episomal or become chromosomally integrated, as long as it can be transcribed to produce the desired stRNA precursor.

Such vectors can be constructed by recombinant DNA technology methods known in the art. Vectors can be plasmid, viral, or other vectors known in the art such as those described herein, used for replication and expression in mammalian cells or other targeted cell types. The nucleic acid sequences encoding the engineered RNA precursors can be prepared using known techniques. For example, two synthetic DNA oligonucleotides can be synthesized to create a novel gene encoding the entire engineered RNA precursor. The DNA oligonucleotides, which will pair, leaving appropriate 'sticky ends' for cloning, can be inserted into a restriction site in a plasmid that contains a promoter sequence (e.g., a Pol II or a Pol III promoter) and appropriate terminator sequences 3' to the engineered RNA precursor sequences (e.g., a cleavage and polyadenylation signal sequence from SV40 or a Pol III terminator sequence).

The invention also encompasses genetically engineered host cells that contain any of the foregoing expression vectors and thereby express the nucleic acid molecules of the invention in the host cell. The host cells can be cultured using known techniques and methods (see, e.g., Culture of Animal Cells (R. I. Freshney, Alan R. Liss, Inc. 1987); Molecular Cloning, Sambrook et al. (Cold Spring Harbor Laboratory Press, 1989)).

Successful introduction of the vectors of the invention into host cells can be monitored using various known methods. For example, transient transfection can be signaled with a reporter, such as a fluorescent marker, such as Green Fluorescent Protein (GFP). Stable transfection can be indicated using markers that provide the transfected cell with resistance to specific environmental factors (e.g., antibiotics and drugs), such as hygromycin B resistance, e.g., in insect cells and in mammalian cells.

3. Regulatory Sequences

The expression of the engineered RNA precursors is driven by regulatory sequences, and the vectors of the invention can include any regulatory sequences known in the art to act in mammalian cells, e.g., human or murine cells; in insect cells; in plant cells; or other cells. The term regulatory sequence includes promoters, enhancers, and other expression control elements. It will be appreciated that the appropriate regulatory sequence depends on such factors as the future use of the cell or transgenic animal into which a sequence encoding an engineered RNA precursor is being introduced, and the level of expression of the desired RNA precursor. A person skilled in the art would be able to choose the appropriate regulatory sequence. For example, the transgenic animals described herein can be used to determine the role of a test polypeptide or the engineered RNA precursors in a particular cell type, e.g., a hematopoietic cell. In this case, a regulatory sequence that drives expression of the transgene ubiquitously, or a hematopoietic-specific regulatory sequence that expresses the transgene only in hematopoietic cells, can be used. Expression of the engineered RNA precursors in a hematopoietic cell means that the cell is now susceptible to specific, targeted RNAi of a particular gene. Examples of various regulatory sequences are described below.

The regulatory sequences can be inducible or constitutive. Suitable constitutive regulatory sequences include the regulatory sequence of a housekeeping gene such as the α-actin regulatory sequence, or may be of viral origin such as regulatory sequences derived from mouse mammary tumor virus (MMTV) or cytomegalovirus (CMV).

Alternatively, the regulatory sequence can direct transgene expression in specific organs or cell types (see, e.g., Lasko et al., 1992, *Proc. Natl. Acad. Sci. USA* 89:6232). Several tissue-specific regulatory sequences are known in the art including the albumin regulatory sequence for liver (Pinkert et al., 1987, *Genes Dev.* 1:268276); the endothelin regulatory sequence for endothelial cells (Lee, 1990, *J. Biol. Chem.* 265:10446-50); the keratin regulatory sequence for epidermis; the myosin light chain-2 regulatory sequence for heart (Lee et al., 1992, *J. Biol. Chem.* 267:15875-85), and the insulin regulatory sequence for pancreas (Bucchini et al., 1986, *Proc. Natl. Acad. Sci. USA* 83:2511-2515), or the vav regulatory sequence for hematopoietic cells (Oligvy et al., 1999, *Proc. Natl. Acad. Sci. USA* 96:14943-14948). Another suitable regulatory sequence, which directs constitutive expression of transgenes in cells of hematopoietic origin, is the murine MHC class I regulatory sequence (Morello et al., 1986, *EMBO J.* 5:1877-1882). Since NMC expression is induced by cytokines, expression of a test gene operably linked to this regulatory sequence can be upregulated in the presence of cytokines.

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals such as mice, include regulation by ecdysone, by estrogen, progesterone, tetracycline, chemical inducers of dimerization, and isopropyl-beta-D1-thiogalactopyranoside (IPTG) (collectively referred to as "the regulatory molecule"). Each of these expression systems is well described in the literature and permits expression of the transgene throughout the animal in a manner controlled by the presence or absence of the regulatory molecule. For a review of inducible expression systems, see, e.g., Mills, 2001, *Genes Devel.* 15:1461-1467, and references cited therein.

The regulatory elements referred to above include, but are not limited to, the cytomegalovirus hCMV immediate early gene, the early or late promoters of SV40 adenovirus (Bernoist et al., *Nature,* 290:304, 1981), the tet system, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. Additional promoters include the promoter contained in the 3' long terminal repeat of Rous sarcoma virus (Yamamoto et al., *Cell* 22:787-797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

4. Assay for Testing Engineered RNA Precursors

*Drosophila* embryo lysates can be used to determine if an engineered RNA precursor was, in fact, the direct precursor of a mature stRNA or siRNA. This lysate assay is described in Tuschl et al., 1999, supra, Zamore et al., 2000, supra, and Hutvdgner et al. 2001, supra. These lysates recapitulate RNAi in vitro, thus permitting investigation into whether the proposed precursor RNA was cleaved into a mature stRNA or siRNA by an RNAi-like mechanism. Briefly, the precursor RNA is incubated with *Drosophila* embryo lysate for various times, and then assayed for the production of the mature siRNA or stRNA by primer extension or Northern hybridization. As in the in vivo setting, mature RNA accumulates in the cell-free reaction. Thus, an RNA corresponding to the proposed precursor can be shown to be converted into a mature stRNA or siRNA duplex in the *Drosophila* embryo lysate.

Furthermore, an engineered RNA precursor can be functionally tested in the *Drosophila* embryo lysates. In this case, the engineered RNA precursor is incubated in the lysate in the presence of a 5' radiolabeled target mRNA in a standard in vitro RNAi reaction for various lengths of time. The target mRNA can be 5' radiolabeled using guanylyl transferase (as described in Tuschl et al., 1999, supra and references therein) or other suitable methods. The products of the in vitro reaction are then isolated and analyzed on a denaturing acrylamide or agarose gel to determine if the target mRNA has been cleaved in response to the presence of the engineered RNA precursor in the reaction. The extent and position of such cleavage of the mRNA target will indicate if the engineering of the precursor created a pre-siRNA capable of mediating sequence-specific RNAi.

III. Methods of Introducing RNAs, Vectors, and Host Cells

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Plants include *arabidopsis*; field crops (e.g., alfalfa, barley, bean, corn, cotton, flax, pea, rape, nice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, black-berry, blueberry, cacao, cherry, coconut, cranberry, date, faJoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber). Examples of vertebrate animals include fish, mammal, cattle, goat, pig, sheep, rodent, hamster, mouse, rat, primate, and human; invertebrate animals include nematodes, other worms, drosophila, and other insects.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

IV. Methods of Treatment:

The present invention provides for both prophylactic and therapeutic methods of treating a subject at risk of (or susceptible to) a disorder or having a disorder associated with aberrant or unwanted target gene expression or activity. "Treatment", or "treating" as used herein, is defined as the application or administration of a therapeutic agent (e.g., a RNA agent or vector or transgene encoding same) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., an RNAi agent or vector or transgene encoding same). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., an RNAi agent or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

3. Pharmacogenomics

The therapeutic agents (e.g., an RNAi agent or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

V. Pharmaceutical Compositions

The invention pertains to uses of the above-described agents for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

VI. Transgenic Organisms

Engineered RNA precursors of the invention can be expressed in transgenic animals. These animals represent a model system for the study of disorders that are caused by, or exacerbated by, overexpression or underexpression (as compared to wildtype or normal) of nucleic acids (and their encoded polypeptides) targeted for destruction by the RNAi agents, e.g., siRNAs and shRNAs, and for the development of therapeutic agents that modulate the expression or activity of nucleic acids or polypeptides targeted for destruction.

Transgenic animals can be farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats). Invertebrates such as *Caenorhabditis elegans* or *Drosophila* can be used as well as non-mammalian vertebrates such as fish (e.g., zebrafish) or birds (e.g., chickens).

Engineered RNA precursors with stems of 18 to 30 nucleotides in length are preferred for use in mammals, such as mice. A transgenic founder animal can be identified based upon the presence of a transgene that encodes the new RNA precursors in its genome, and/or expression of the transgene in tissues or cells of the animals, for example, using PCR or Northern analysis. Expression is confirmed by a decrease in the expression (RNA or protein) of the target sequence.

A transgenic founder animal can be used to breed additional animals carrying the transgene. Moreover, transgenic animals carrying a transgene encoding the RNA precursors can further be bred to other transgenic animals carrying other transgenes. In addition, cells obtained from the transgenic founder animal or its offspring can be cultured to establish primary, secondary, or immortal cell lines containing the transgene.

1. Procedures for Making Transgenic, Non-Human Animals

A number of methods have been used to obtain transgenic, non-human animals, which are animals that have gained an additional gene by the introduction of a transgene into their cells (e.g., both the somatic and genn cells), or into an ancestor's genn line. In some cases, transgenic animals can be generated by commercial facilities (e.g., The Transgenic *Drosophila* Facility at Michigan State University, The Transgenic Zebrafish Core Facility at the Medical College of Georgia (Augusta, Ga.), and Xenogen Biosciences (St. Louis, Mo.). In general, the construct containing the transgene is supplied to the facility for generating a transgenic animal.

Methods for generating transgenic animals include introducing the transgene into the germ line of the animal. One method is by microinjection of a gene construct into the pronucleus of an early stage embryo (e.g., before the four-cell stage; Wagner et al., 1981, Proc. Natl. Acad. Sci. USA 78:5016; Brinster et al., 1985, Proc. Natl. Acad. Sci. USA 82:4438). Alternatively, the transgene can be introduced into the pronucleus by retroviral infection. A detailed procedure for producing such transgenic mice has been described (see e.g., Hogan et al., MP1 ulating the Mouse ErnbnLo. Cold Spring Harbour Laboratory, Cold Spring Harbour, N Y (1986); U.S. Pat. No. 5,175,383 (1992)). This procedure has also been adapted for other animal species (e.g., Hammer et al., 1985, Nature 315:680; Murray et al., 1989, Reprod. Fert. Devl. 1:147; Pursel et al., 1987, Vet. hnmunol. Histopath. 17:303; Rexroad et al., 1990, J. Reprod. Fert. 41 (suppl): 1 19; Rexroad et al., 1989, Molec. Reprod. Devl. 1:164; Simons et al., 1988, BioTechnology 6:179; Vize et al., 1988, J. Cell. Sci. 90:295; and Wagner, 1989, J. Cell. Biochem. 13B (suppl): 164).

In brief, the procedure involves introducing the transgene into an animal by microinjecting the construct into the pronuclei of the fertilized mammalian egg(s) to cause one or more copies of the transgene to be retained in the cells of the developing mammal(s). Following introduction of the transgene construct into the fertilized egg, the egg may be incubated in vitro for varying amounts of time, or reimplanted a in surrogate host, or both. One common method is to incubate the embryos in vitro for about 1-7 days, depending on the species, and then reimplant them into the surrogate host. The presence of the transgene in the progeny of the transgenically manipulated embryos can be tested by Southern blot analysis of a segment of tissue.

Another method for producing germ-line transgenic animals is through the use of embryonic stem (ES) cells. The gene construct can be introduced into embryonic stem cells by homologous recombination (Thomas et al., 1987, Cell 51:503; Capecchi, Science 1989, 244:1288; Joyner et al., 1989, Nature 338:153) in a transcriptionally active region of the genome. A suitable construct can also be introduced into embryonic stem cells by DNA-mediated transfection, such as by 17 electroporation (Ausubel et al., Current Protocols in Molecular Biology, John Wiley & Sons, 1987). Detailed procedures for culturing embryonic stem cells (e.g., ES-D3@ ATCC #CCL-1934, ES-El4TG2a, ATCC #CCL-1821, American Type Culture Collection, Rockville, AM) and methods of making transgenic animals from embryonic stem cells can be found in Teratocarcinomas and Embi3Lonic Stem Cells, A Practical Approach, ed. E. J. Robertson (IRL Press, 1987). In brief, the ES cells are obtained from pre-implantation embryos cultured in vitro (Evans et al., 1981, Nature 292:154-156). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal.

In the above methods, the transgene can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292). A plasmid is a DNA molecule that can replicate autonomously in a host.

The transgenic, non-human animals can also be obtained by infecting or transfecting cells either in vivo (e.g., direct injection), ex vivo (e.g., infecting the cells outside the host and later reimplanting), or in vitro (e.g., infecting the cells outside host), for example, with a recombinant viral vector carrying a gene encoding the engineered RNA precursors. Examples of suitable viral vectors include recombinant retroviral vectors (Valerio et al., 1989, Gene 84:419; Scharfinan et al., 1991, Proc. Natl. Acad. Sci. USA 88:462; Miller and Buttimore, 1986, Mol. Cell. Biol. 6:2895), recombinant adenoviral vectors (Freidman et al., 1986, Mol. Cell. Biol. 6:3791; Levrero et al., 1991, Gene 101: 195), and recombinant Herpes simplex viral vectors (Fink et al., 1992, Human Gene Therapy 3:11). Such methods are also useful for introducing constructs into cells for uses other than generation of transgenic animals.

Other approaches include insertion of transgenes encoding the new engineered RNA precursors into viral vectors including recombinant adenovirus, adenoassociated virus, and herpes simplex virus-1, or recombinant bacterial or eukaryotic plasmids. Viral vectors transfect cells directly. Other approaches include delivering the transgenes, in the form of plasmid DNA, with the help of, for example, cationic liposomes (lipofectin) or derivatized (e.g., antibody conjugated) polylysine conjugates, gramacidin S, artificial viral envelopes, or other such intracellular carriers, as well as direct injection of the transgene construct or $CaPO_4$ precipitation carried out in vivo. Such methods can also be used in vitro to introduce constructs into cells for uses other than generation of transgenic animals.

Retrovirus vectors and adeno-associated virus vectors can be used as a recombinant gone delivery system for the transfer of exogenous genes in vivo or in vitro. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, 1990, Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9 9.14 and other standard laboratory manuals.

Examples of suitable retroviruses include pLJ, pZIP, pWE and pEM which are known to those skilled in the art. Examples of suitable packaging virus lines for preparing both ecotropic and amphotropic retroviral systems include Psi-Crip, PsiCre, Psi-2 and Psi-Am. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

In another example, recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection. Another viral gene delivery system useful in the present invention also utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988, BioTechniques 6:616), Rosenfeld et al. (1991, Science 252: 431-434), and Rosenfeld et al. (1992, Cell 68:143-155). Suitable adenoviral vectors derived from the adenovirus strain Ad type 5 d1324 or other strains of adenovirus (e.g., Ad2, AO, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al., 1992, cited supra). Furthermore, the virus particle is relatively stable and amenable to purification and concentration, and as above, can be modified to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis hz situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, 1986, J. Virol. 57:267).

Yet another viral vector system useful for delivery of the subject transgenes is the adeno-associated virus (AAV). Adeno-associated virus is a naturally occurring defective virus that requires another virus, such as an adenovirus or a herpes virus, as a helper virus for efficient replication and a productive life cycle. For a review, see Muzyczka et al. (1992, Curr. Topics in Micro. and Immunol. 158:97-129). It is also one of the few viruses that may integrate its DNA into non-dividing cells, and exhibits a high frequency of stable integration (see for example Flotte et al. (1992, Am. J. Respir. Cell. Mol. Biol. 7:349-356; Samulski et al., 1989, J. Virol. 63:3822-3828; and McLaughlin et al. (1989, J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) MoL Cell. Biol. 5:3251-3260 can be used to introduce DNA into cells. A variety of nucleic acids have been introduced into different cell types using AAV vectors (see for example Hennonat et al. (1984) Proc. Nad. Acad. Sci. USA 8 1:64666470; Tratschin et al. (1985) Mol. Cell. BioL 4:2072-2081; Wondisford et al. (1988) MoL EndocrinoL 2:32-39; Tratschin et al. (1984) J ViroL 51:611-619; and Flotte et al. (1993) J BioL Chem. 268:3781-3790).

In addition to viral transfer methods, such as those illustrated above, non-viral methods can also be employed to cause expression of an shRNA or engineered RNA precursor of the invention in the tissue of an animal. Most non-viral methods of gene transfer rely on nominal mechanisms used by mammalian cells for the uptake and intracellular transport of macromolecules. In preferred embodiments, non-viral gene delivery systems of the present invention rely on endocytic pathways for the uptake of the subject gene of the invention by the targeted cell. Exemplary gene delivery systems of this type include liposomal derived systems, poly-lysine conjugates, and artificial viral envelopes. Other embodiments include plasmid injection systems such as are described in Meuli et al., (2001) J Invest. DerinatoL, 116 (1):131-135; Cohen et al., (2000) Gene Ther., 7(22):1896-905; and Tam et al., (2000) Gene Ther., 7(21):186774.

In a representative embodiment, a gene encoding an shRNA or engineered RNA precursor of the invention can be entrapped in liposomes bearing positive charges on their surface (e.g., lipofectins) and (optionally) which are tagged with antibodies against cell surface antigens of the target tissue (Mizuno et al., (1992) No Shinkei Geka, 20:547-55 1; PCT publication WO91/06309; Japanese patent application 10473 8 1; and European patent publication EP-A-43 075).

Animals harboring the transgene can be identified by detecting the presence of the transgene in genomic DNA (e.g., using Southern analysis). In addition, expression of the shRNA or engineered RNA precursor can be detected directly (e.g., by Northern analysis). Expression of the transgene can also be confirmed by detecting a decrease in the amount of protein corresponding to the targeted sequence. When the transgene is under the control of an inducible or developmentally regulated promoter, expression of the target protein is decreased when the transgene is induced or at the developmental stage when the transgene is expressed, respectively.

2. Clones of Transgenic Animals

Clones of the non-human transgenic animals described herein can be produced according to the methods described in Wilmut et al. ((1997) Nature, 385:810-813) and PCT publication Nos. WO 97/07668 and WO 97/07669. In brief, a cell, e.g., a somatic cell from the transgenic animal, can be isolated and induced to exit the growth cycle and enter the GO phase to become quiescent. The quiescent cell can then be fused, e.g., through the use of electrical pulses, to an enucleated oocyte from an animal of the same species from which the quiescent cell is isolated. The reconstructed oocyte is then cultured such that it develops into a morula or blastocyte and is then transferred to a pseudopregnant female foster animal. Offspring borne of this female foster animal will be clones of the animal from which the cell, e.g., the somatic cell, was isolated.

Once the transgenic animal is produced, cells of the transgenic animal and cells from a control animal are screened to determine the presence of an RNA precursor nucleic acid sequence, e.g., using polymerase chain reaction (PCR). Alternatively, the cells can be screened to determine if the RNA precursor is expressed (e.g., by standard procedures such as Northern blot analysis or reverse transcriptase-polymerase chain reaction (RT-PCR); Sambrook et al., Molecular Cloning—A Laboratory Manual, (Cold Spring Harbor Laboratory, 1989)).

The transgenic animals of the present invention can be homozygous or heterozygous, and one of the benefits of the invention is that the target mRNA is effectively degraded even in heterozygotes. The present invention provides for transgenic animals that carry a transgene of the invention in all their cells, as well as animals that carry a transgene in some, but not all of their cells. That is, the invention provides for mosaic animals. The transgene can be integrated as a single transgene or in concatatners, e.g., head-to-head tandems or head-to-tail tandems.

For a review of techniques that can be used to generate and assess transgenic animals, skilled artisans can consult Gordon (IwL Rev. CytoL 1 1 5:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., BiolTechnology 9:86, 1991; Palmiter et al., Cell 41:343, 1985; Kraemer et al., "Genetic Manipulation of the Early Mammalian Embryo," Cold Spring Harbor Press, Cold Spring Harbor, N.Y., 1985; Hammer et al., Nature 315:680, 1985; Purcel et al., Science, 244:1281, 1986; Wagner et al., U.S. Pat. No. 5,175,385; and Krimpenfort et al., U.S. Pat. No. 5,175,384.

3. Transgenic Plants

Among the eukaryotic organisms featured in the invention are plants containing an exogenous nucleic acid that encodes an engineered RNA precursor of the invention.

Accordingly, a method according to the invention comprises making a plant having a nucleic acid molecule or construct, e.g., a transgene, described herein. Techniques for introducing exogenous micleic acids into monocotyledonous and dicotyledonous plants are known in the art, and include, without limitation, *Agrobacterium*-mediated transformation, viral vector-mediated transformation, electroporation and particle gun transformation, see, e.g., U.S. Pat. Nos. 5,204,253 and 6,013,863. If a cell or tissue culture is used as the recipient tissue for transformation, plants can be regenerated from transformed cultures by techniques known to those skilled in the art. Transgenic plants can be entered into a breeding program, e.g., to introduce a nucleic acid encoding a polypeptide into other lines, to transfer the nucleic acid to other species or for further selection of other desirable traits. Alternatively, transgenic plants can be propagated vegetatively for those species amenable to such techniques. Progeny includes descendants of a particular plant or plant line. Progeny of a plant include seeds formed on F1, F2, F3, and subsequent generation plants, or seeds formed on BQ, BC2, BC3, and subsequent generation plants. Seeds produced by a transgenic plant can be grown and then selfed (or outcrossed and selfed) to obtain seeds homozygous for the nucleic acid encoding a novel polypeptide.

A suitable group of plants with which to practice the invention include dicots, such as safflower, alfalfa, soybean, rapeseed (high erucic acid and canola), or sunflower. Also suitable are monocots such as corn, wheat, rye, barley, oat, rice, millet, amaranth or sorghum. Also suitable are vegetable crops or root crops such as potato, broccoli, peas, sweet corn, popcorn, tomato, beans (including kidney beans, lima beans, dry beans, green beans) and the like. Also suitable are fruit crops such as peach, pear, apple, cherry, orange, lemon, grapefruit, plum, mango and palm. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyalnus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* and *Zea.*

The skilled artisan will appreciate that the enumerated organisms are also useful for practicing other aspects of the invention, e.g., as host cells, as described supra.

The nucleic acid molecules of the invention can be expressed in plants in a cell- or tissue-specific manner according to the regulatory elements chosen to include in a particular nucleic acid construct present in the plant. Suitable cells, tissues, and organs in which to express a chimeric polypeptide of the invention include, without limitation, egg cell, central cell, synergid cell, zygote, ovule primordia, nucellus, integuments, endothelium, female gametophyte cells, embryo, axis, cotyledons, suspensor, endosperm, seed coat, ground meristem, vascular bundle, cambium, phloem, cortex, shoot or root apical meristems, lateral shoot or root meristems, floral meristem, leaf primordia, leaf mesophyll cells, and leaf epidermal cells, e.g., epidermal cells involved in fortning the cuticular layer. Also suitable are cells and tissues grown in liquid media or on semi-solid media.

4. Transgenic Fungi

Other eukaryotic organisms featured in the invention are fungi containing an exogenous nucleic acid molecule that encodes an engineered RNA precursor of the invention. Accordingly, a method according to the invention comprises introducing a nucleic acid molecule or construct as described herein into a fungus. Techniques for introducing exogenous nucleic acids into many fungi are known in the art, see, e.g., U.S. Pat. Nos. 5,252,726 and 5,070,020. Transformed fungi can be cultured by techniques known to those skilled in the art. Such fungi can be used to introduce a nucleic acid encoding a polypeptide into other fungal strains, to transfer the nucleic acid to other species or for ftirther selection of other desirable traits.

A suitable group of fungi with which to practice the invention include fission yeast and budding yeast, such as *Saccharomyces cereviseae, S. pombe, S. carlsbergeris* and *Candida albicans*. Filamentous fungi such as *Aspergillus* spp. and *Penicillium* spp. are also useful.

VII. Knockout and/or Knockdown Cells or Organisms

A further preferred use for the RNAi agents of the present invention (or vectors or transgenes encoding same) is a functional analysis to be carried out in eukaryotic cells, or eukaryotic non-human organisms, preferably mammalian cells or organisms and most preferably human cells, e.g., cell lines such as HeLa or 293 or rodents, e.g., rats and mice. By administering a suitable RNAi agent which is sufficiently complementary to a target mRNA sequence to direct target-specific RNA interference, a specific knockout or knockdown phenotype can be obtained in a target cell, e.g., in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogeneous target gene wherein said cell or organism is transfected with at least one vector comprising DNA encoding a RNAi agent capable of inhibiting the expression of the target gene. It should be noted that the present invention allows a target-specific knockout or knockdown of several different endogeneous genes due to the specificity of the RNAi agent.

Gene-specific knockout or knockdown phenotypes of cells or non-human organisms, particularly of human cells or non-human mammals may be used in analytic to procedures, e.g., in the functional and/or phenotypical analysis of complex physiological processes such as analysis of gene expression profiles and/or proteomes. Preferably the analysis is carried out by high throughput methods using oligo-nucleotide based chips.

Using RNAi based knockout or knockdown technologies, the expression of an endogeneous target gene may be inhibited in a target cell or a target organism. The endogeneous gene may be complemented by an exogenous target nucleic acid coding for the target protein or a variant or mutated form of the target protein, e.g., a gene or a DNA, which may optionally be fused to a further nucleic acid sequence encoding a detectable peptide or polypeptide, e.g., an affinity tag, particularly a multiple affinity tag.

Variants or mutated forms of the target gene differ from the endogeneous target gene in that they encode a gene product which differs from the endogeneous gene product on the amino acid level by substitutions, insertions and/or deletions of single or multiple amino acids. The variants or mutated forms may have the same biological activity as the endogeneous target gene. On the other hand, the variant or mutated target gene may also have a biological activity, which differs from the biological activity of the endogeneous target gene, e.g., a partially deleted activity, a completely deleted activity, an enhanced activity etc. The complementation may be accomplished by compressing the polypeptide encoded by the endogeneous nucleic acid, e.g., a fusion protein comprising the target protein and the affinity tag and the double stranded RNA molecule for knocking out the endogeneous gene in the target cell. This compression may be accomplished by using a suitable expression vector expressing both the polypeptide encoded by the endogenous nucleic acid, e.g., the tag-modified target protein and the double stranded RNA molecule or alternatively by using a combination of expression vectors. Proteins and protein complexes which are synthesized de novo in the target cell will contain the exogenous gene product, e.g., the modified fusion protein. In order to avoid suppression of the exogenous gene product by the RNAi agent, the nucleotide sequence encoding the exogenous nucleic acid may be altered at the DNA level (with or without causing mutations on the amino acid level) in the part of the sequence which so is homologous to the RNAi agent. Alternatively, the endogeneous target gene may be complemented by corresponding nucleotide sequences from other species, e.g., from mouse.

VIII. Functional Genomics and/or Proteomics

Preferred applications for the cell or organism of the invention is the analysis of gene expression profiles and/or proteomes. In an especially preferred embodiment an analysis of a variant or mutant form of one or several target proteins is carried out, wherein said variant or mutant forms are reintroduced into the cell or organism by an exogenous target nucleic acid as described above. The combination of knockout of an endogeneous gene and rescue by using mutated, e.g., partially deleted exogenous target has advantages compared to the use of a knockout cell. Further, this method is particularly suitable for identifying functional domains of the targeted protein. In a further preferred embodiment a comparison, e.g., of gene expression profiles and/or proteomes and/or phenotypic characteristics of at least two cells or organisms is carried out. These organisms are selected from: (i) a control cell or control organism without target gene inhibition, (ii) a cell or organism with target gene inhibition and (iii) a cell or organism with target gene inhibition plus target gene complementation by an exogenous target nucleic acid.

Furthermore, the RNA knockout complementation method may be used for is preparative purposes, e.g., for the affinity purification of proteins or protein complexes from eukaryotic cells, particularly mammalian cells and more particularly human cells. In this embodiment of the invention, the exogenous target nucleic acid preferably codes for a target protein which is fused to art affinity tag. This method is suitable for functional proteome analysis in mammalian cells, particularly human cells.

Another utility of the present invention could be a method of identifying gene function in an organism comprising the use of an RNAi agent to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for the yeast, *D. melanogaster*, and *C. elegans* genomes, can be coupled with the invention to determine gene function in an organism (e.g., nematode). The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects. A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which RNA can be introduced into an intact cell/organism containing the target gene allows the present invention to be used in high throughput screening (HTS). Solutions containing RNAi agents that are capable of inhibiting the different expressed genes can be placed into individual wells positioned on a microtiter plate as an ordered array, and intact cells/organisms in each well can be assayed for any changes or modifications in behavior or development due to inhibition of target gene activity. The amplified RNA can be fed directly to, injected into, the cell/organism containing the target gene. Alternatively, the RNAi agent can be produced from a vector, as described herein. Vectors can be injected into, the cell/organism containing the target gene. The function of the target gene can be assayed from the effects it has on the cell/organism when gene activity is inhibited. This screening could be amenable to small subjects that can be processed in large number, for example: *arabidopsis*, bacteria, *drosophila*, fungi, nematodes, viruses, zebrafish, and tissue culture cells derived from mammals. A nematode or other organism that produces a colorimetric, fluorogenic, or luminescent signal in response to a regulated promoter (e.g., transfected with a reporter gene construct) can be assayed in an HTS format.

The present invention may be useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of RNAi agents at specific times of development and locations in the organism without introducing permanent mutations into the target genome.

IX. Screening Assays

The methods of the invention are also suitable for use in methods to identify and/or characterize potential pharmacological agents, e.g., identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein comprising: (a) a eukaryotic cell or a eukaryotic non-human organism capable of expressing at least one endogenous target gene coding for said so target protein, (b) at least one RNA agent capable of inhibiting the expression of said at least one endogenous target gene, and (c) a test substance or a collection of test substances wherein pharmacological properties of said test substance or said collection are to be identified and/or characterized. Further, the system as described above preferably comprises: (d) at least one exogenous target nucleic acid coding for the target protein or a variant or mutated form of the target protein wherein said exogenous target nucleic acid differs from the endogenous target gene on the nucleic acid level such that the expression of the exogenous target nucleic acid is substantially less inhibited by the RNA agent than the expression of the endogenous target gene.

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) Nature 364:555-556), bacteria (Ladner U.S. Pat. No. 5,223, 409), spores (Ladner USP 409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222: 301-310); (Ladner supra.)).

In a preferred embodiment, the library is a natural product library, e.g., a library produced by a bacterial, fungal, or yeast culture. In another preferred embodiment, the library is a synthetic compound library.

This invention is further illustrated by the following examples which should not be construed as limiting. The contents of all references, patents and published patent applications cited throughout this application are incorporated herein by reference.

EXAMPLES

Materials and Methods

Lysate Preparation

Fly Embryo Lysates were Prepared as Previously Described (Tuschl et al. 1999). Wheat germ extracts were prepared from frozen or vacuum-packed raw wheat germ (e.g., Fearn Nature Fresh Raw Wheat Germ, Bread and Circus) as described (Erickson and Blobel 1983). The extract was centrifuged at 14,500 g at 4° C. for 25 min; the supernatant was then frozen in aliquots in liquid nitrogen and stored at −80° C. For cauliflower extract, the outer layer of fresh cauliflower (Shaws Supermarket) was harvested with a razor blade and ground to a powder under liquid nitrogen in a mortar and pestle, then homogenized with 3 mL of 1×lysis buffer (100 mM potassium acetate, 30 mM HEPES-KOH at pH 7.4, 2 mM magnesium acetate) containing 5 mM dithiothreitol (DTT) and 1 mg/mL Pefabloc SC (Boehringer Mannheim) per gram of plant tissue. The extract was centrifuged, and the supernatant was stored as described for the *Drosophila* embryo lysate.

Analysis of dsRNA Processing

For analysis of dsRNA processing, 5 nM internally α-32P-UTP-labeled dsRNA was incubated in a 10-4 reaction containing 5 µL of *Drosophila* embryo lysate (Tuschl et al. 1999) or wheat germ extract, 100 µM GTP, 500 µM ATP, 10 mM creatine phosphate, 10 µg/mL creatine phosphokinase, 5 mM DTT, and 0.1 U/µL RNasin (Promega) at 25° C. for 3 h. Reactions were stopped by the addition of 2× proteinase K buffer [200 mM Tris-HCl at pH 7.5, 25 mM EDTA, 300 mM NaCl, 2% (w/v) sodium dodecyl sulfate] and deproteinized with mg/mL proteinase K at 65° C. for 15 min. Products were precipitated with 3 volumes cold ethanol and analyzed by electrophoresis in a 15% polyacrylamide sequencing gel.

Gel Filtration and RNAse Protection

Internally α-32P-UTP-labeled dsRNAs were incubated in wheat germ extract, then deproteinized at room temperature with proteinase K (1 h) and RNA-precipitated with 3 volumes of cold ethanol. The RNA was resuspended in 1× lysis buffer and analyzed by gel filtration as described (Nykanen et al. 2001). For RNase protection, the RNA products of a 10-μL wheat germ extract reaction were deproteinized at room temperature and analyzed by RNAse protection essentially as described (Sambrook et al. 1989). Briefly, the siRNA pellets were dissolved in 10 μL of RNAse digestion buffer (300 mM NaCl, 10 mM Tris-HCl at pH 7.4, and 5 mM EDTA at pH 7.5) containing 10 mM [beta]-glycerophosphate, 5 mM ATP, 0-6.6 U of RNAse A, and 0-1.1 U of RNAse T1. For control experiments, 5'-32P-radiolabeled synthetic, double-stranded siRNAs were mixed with the products of a wheat germ reaction performed with unlabeled dsRNA and coprecipitated with 3 volumes of cold ethanol. RNAse protection was at 25° C. for 1 h, stopped by adding 0.6 μL of 10% SDS and 0.3 μL of 20 mg/mL proteinase K, then incubated at 25° C. for 1 h. The reactions were then adjusted to 200 μL with 2×PK buffer containing 0.2 mg/mL Glycogen (Roche), extracted with an equal volume of phenol/chloroform/isoamylalcohol (25:24:1; v/v/v), precipitated with 3 volumes of cold ethanol, and analyzed in a 15% sequencing polyacrylamide gel.

Synthetic siRNAs Used as Inhibitors

The 21-nt siRNA inhibitor comprised CGUACGCGGAAUACUUCGANU (SEQ ID NO:23)(N=5-Iodo-U) annealed with UCGAAGUAUUCCGCGUACGUG (SEQ ID NO:6); the 25-mer comprised AUCACGUACGCGGAAUACUUCGANU (SEQ ID NO:24)(N=5-Iodo-U) annealed with UCGAAGUAUUCCGCGUACGUGAUUG (SEQ ID NO:8). The 5-Iodo-U nucleotides were included to facilitate studies not presented here, and we have no evidence they enhance the effectiveness of the siRNAs as inhibitors.

Analysis of RdRP Activity

Assays were performed in a final volume of 10 μL containing 5 μL of lysate, 100 μM GTP, 100 μM CTP, 500 μM ATP, 20 μM UTP, 5 μCi of α-32P-UTP (25 Ci/mmole), 10 mM creatine phosphate, 10 μg/mL creatine phosphokinase, 5 mM DTT, 0.2 U/4 Super-RNasin (Ambion), and 7-methyl-G- or A-capped RNAs. After incubation at 25° C. for 3 h, the reaction was deproteinized with proteinase K in 200 μL of 2× proteinase K buffer at 65° C. for 15 min. After phenol/chloroform/isoamylalcohol extraction, the aqueous phase was precipitated with 3 volumes of cold ethanol, resuspended in 10 μL of 2× formamide loading buffer as described (Sambrook et al. 1989), and resolved on 10% or 15% polyacrylamide sequencing gels. For primed assays, capped RNAs were preincubated with single-stranded 21-nt RNA primers or siRNA duplexes at room temperature for 10 min before the remaining reaction components were added.

Arabidopsis PHV, PHB, and Mutant PHV Target RNAs

Arabidopsis PHV and PHB cDNA sequences containing the miR165/166 complementary sequences were amplified from an Arabidopsis flower cDNA library (CD4-6) by polymerase chain reaction (PCR) using the following primer pairs: 5'-PHV primer, GCGTAATACGACTCACTATAGGCGCCGGAACAAGTTG AAG (SEQ ID NO:7), and 3'-PHV primer, GACAGTCACGGAACCAAGATG (SEQ ID NO:8); or 5'-PHB primer, GCGTAATACGACTCACTATAGGTGAGTCTGTGGTCGTGAGTG (SEQ ID NO:9), and 3'-PHB primer, GCTGCTGCTAAAGTCGTAGGA (SEQ ID NO:10). The Arabidopsis G [right-arrow]. A mutant phv template was initially amplified using the 5'-PHV primer and CCACTGCAGTTGCGTGAAACAGCTACGATACCAATAGAATCCGGATCAGGC TTCATCCC (SEQ ID NO:11). This PCR product was diluted 100-fold, then reamplified with the 5'-PHV primer and GACAGTCACGGAACCAAGATGGACGATCTTTGAGGATTTCAGCGACCTTCAT GGGTTCTAAACTCACGAGGCCACAGGCACGTGCTGCTATTCCACTGCAGTTG CGTGAAACAGC (SEQ ID NO:12). In vitro RNA transcription and cap labeling were as described (Tuschl et al. 1999; Zamore et al. 2000).

In Vitro RNAi in Fly Embryo Lysate and Wheat Germ Extract

For RNAi in Drosophila embryo lysate, four siRNA duplexes were chemically synthesized (Dharmacon), annealed, and incubated in a standard RNAi reaction (Zamore et al. 2000). The sequences of siRNAs (sense and antisense strands) corresponding to miR165, miR166, PHV, and mutant phv target positions were miR165, UCGGACCAGGCUUCAUCCCCC (SEQ ID NO:13) and GGGAUGAAGCCUGGUCCGAGG (SEQ ID NO:14); miR166, UCGGACCAGGCUUCAUUCCCC (SEQ ID NO:15) and GGAAUGAAGCCUGGUCCGAGA (SEQ ID NO:16); PHV, CCGGACCAGGCUUCAUCCCAA (SEQ ID NO:17) and GGGAUGAAGCCUGGUCCGGAU (SEQ ID NO:18); and mutant phv, CCGGAUCAGGCUUCAUCCCAA (SEQ ID NO:19) and GGGAUGAAGCCUGAUCCGGAU (SEQ ID NO:20). Wheat germ extract target cleavage reactions were as standard Drosophila in vitro RNAi reactions, except that no exogenous siRNAs were added.

Total RNA Isolation and Northern Analysis

Total RNA was isolated from lysates, and Northern analysis was performed as described (Hutvagner and Zamore 2002). 5'-32P-radiolabeled synthetic miR165 antisense siRNA (above) was used as probe.

Overview of Examples I-VI

The data presented in Examples I-VI demonstrate that extracts of wheat germ, introduced for the study of translation and protein translocation in the 1970s (Roberts and Paterson 1973), recapitulate many of the key features of RNA silencing in plants. Using this in vitro system, it is shown that in plants, ATP-dependent, Dicer-like enzymes cleave dsRNA into small RNAs that have the structure of siRNAs. Unlike Drosophila embryos or mammalian cells, plants convert dsRNA into two distinct classes of siRNAs, long and short siRNAs. Inhibitor studies indicate that a different Dicer-like enzyme generates each siRNA class.

The data further demonstrate that a wheat RdRP activity can synthesize dsRNA using exogenous single-stranded RNA as a template without an exogenous primer, and that this dsRNA is preferentially converted into long siRNAs.

Finally, it is demonstrated that wheat germ extracts contain an endogenous RISC programmed with a miRNA. This endogenous miRNA complex can direct efficient cleavage of the wild-type Arabidopsis PHAVOLUTA (PHV) mRNA sequence, but not that of a previously described dominant PHV mutant that perturbs leaf development. This finding supports the view that in plants miRNAs direct RNAi and explains the molecular basis for the dominant PHV mutation in Arabidopsis. Interestingly, exact complementarity between the miRNA and target mRNA is not necessary for the miRNA to direct efficient target cleavage. In fact, it is demonstrated that the efficiency of cleavage is greater when a G:U base pair, referred to also as a G:U wobble, is present near the 5' or 3' end of the complex formed between the miRNA and the target. Understanding the natural mechanism by which miRNAs efficiency mediate RNAi in plants allows for the design of improved RNAi agents for use in mediating RNAi not only in plants, but in eukaryotes (in particular, in mammals).

Figure 1B:
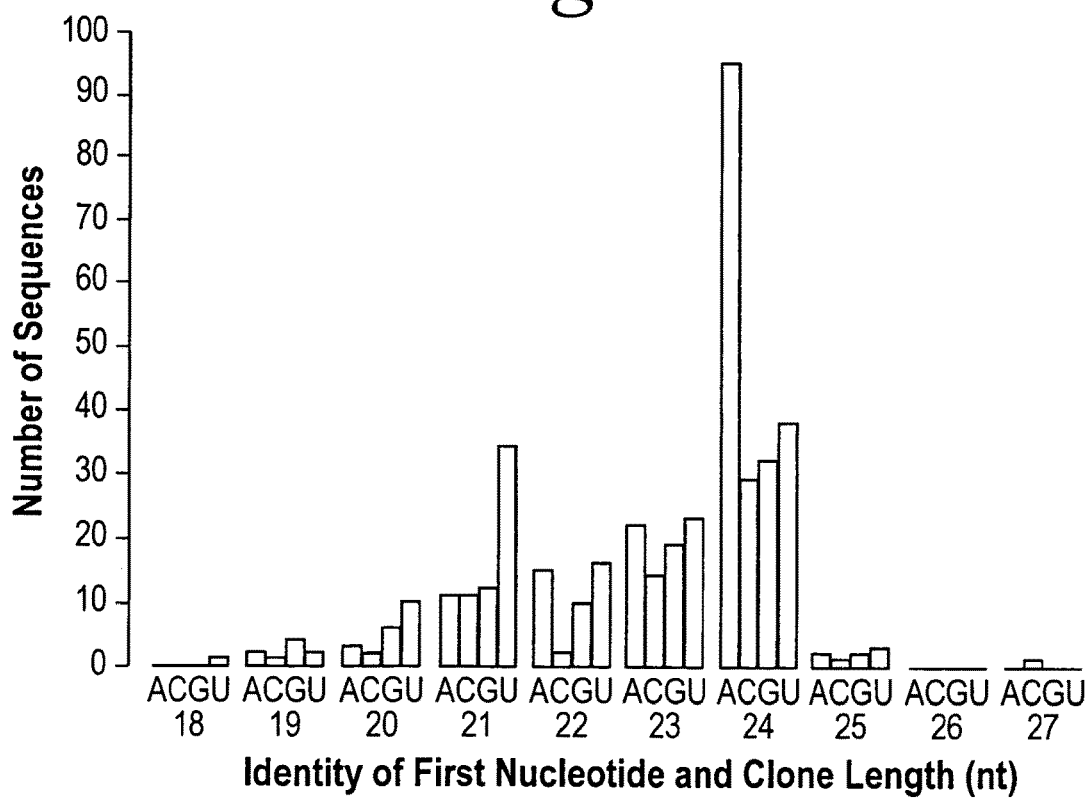

Example I: Two Distinct Classes of Small RNAs Derived from dsRNA in Plant Extracts Two distinct classes of small RNAs are produced in transgenic plants bearing silenced transgenes (Hamilton et al. 2002; Mallory et al. 2002). To test if the production of these two classes of small RNAs was a normal feature of plant biology or a specialized response to foreign DNA, the length distribution of a nonredundant set of 423 endogenous small RNAs cloned from *Arabidopsis thaliana* was examined. (For the sequences of 143 of the small RNAs see Llave et al. 2002a; Reinhart et al. 2002). Excluded from this analysis are cloned fragments of tRNA and rRNA. Included in the set are known and predicted miRNAs, as well as small RNAs of unknown function corresponding to intragenic regions or to mRNA sequences in either the sense or antisense orientation. The distribution of lengths within this set was bimodal, with peaks at 21 and 24 nt (FIG. 1A). In contrast, the length distribution of cloned small RNAs from *C. elegans* forms a single broad peak (Lau et al. 2001). The two classes of green fluorescent protein (GFP)-derived small RNAs were proposed to be siRNAs with distinct RNA silencing functions: the ~21-mers to direct posttranscriptional silencing via mRNA degradation and the ~24-mers to trigger systemic silencing and the methylation of homologous DNA (Hamilton et al. 2002). Analysis of the two classes of endogenous small RNAs indicates that each class has a distinct sequence bias, with a 5'-uridine predominating in the shorter class and a 5'-adenosine in the longer class (FIG. 1B). The 5' sequence bias of the short class is produced by the inclusion in the data set of miRNAs, which in plants and animals typically begin with uridine (Lagos-Quintana et al. 2001, 2002; Lau et al. 2001; Lee and Ambros 2001; Reinhart et al. 2002). Thus, the non-miRNA small RNAs in the shorter class display no 5' sequence bias, whereas a 5'-adenosine is overrepresented in the longer class. The two classes are either generated by different enzymes, function in separate effector complexes, or both.

Example II: Plant Small RNAs are Bona Fide siRNAs

Figure 2A:
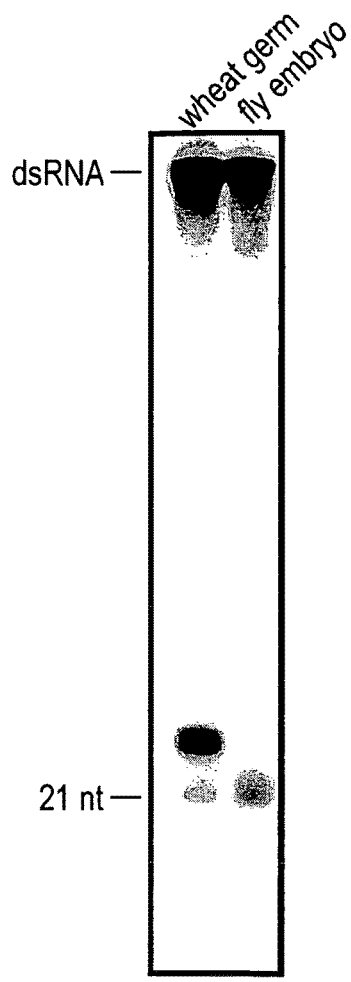
Figure 2B:
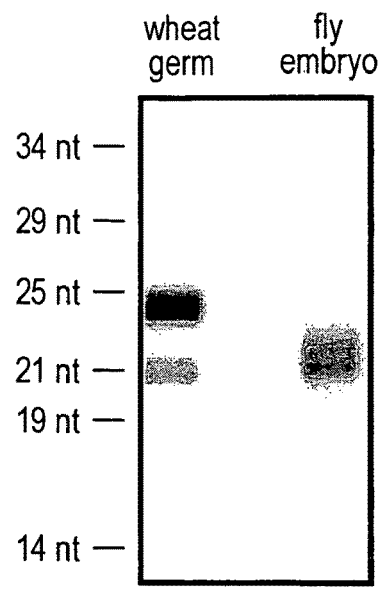
Figure 2C:
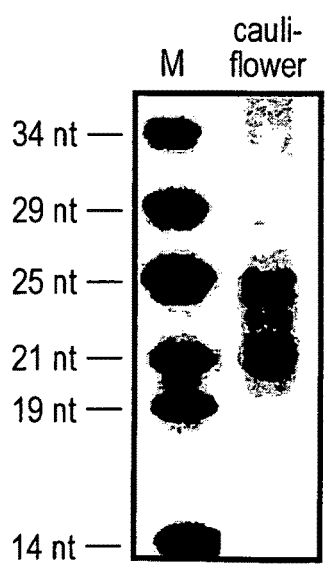
Figure 2D:
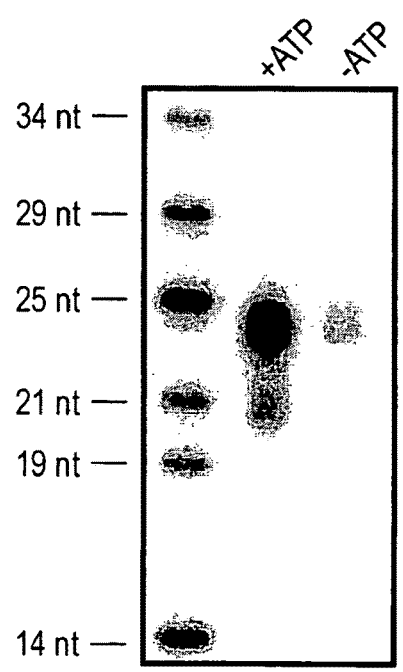

Although the small RNAs that correlate with the posttranscriptional silencing of homologous target mRNAs were first discovered in plants (Hamilton and Baulcombe 1999), they have not yet been shown to be the direct products of endonucleolytic cleavage of long dsRNA. To begin to test if small RNAs are, in fact, siRNAs, we prepared plant extracts and monitored them for Dicer-like activity. When uniformly 32P-radiolabeled dsRNA was incubated in wheat germ extract, it was efficiently cleaved into small RNAs (FIG. 2A). As reported previously for extracts of *Drosophila* (Zamore et al. 2000) and for purified *Drosophila* (Bernstein et al. 2001) and human Dicer (Billy et al. 2001), no intermediate products were detected in the conversion of dsRNA into small RNAs. Unlike the fly and human Dicer reactions, two discrete size classes, one ~21-nt and the other 24-25-nt long, were produced from the dsRNA upon incubation in wheat germ extract (FIG. 2B). The ratio of wheat 24-25-mers to ~21-mers in 14 separate reactions was 4±1.7, similar to the roughly 2.5-fold excess of longer small RNA sequences cloned from *Arabidopsis*. (The 2.5-fold excess of long to short, cloned endogenous small RNAs underestimates the ratio, because it includes miRNAs, which are predominantly short.). Silencing-related small RNAs have thus far only been demonstrated in vivo for dicots, and wheat is a monocot. Extracts of the dicot cauliflower, a member of the mustard family like *Arabidopsis*, also converted dsRNA into two discrete sizes of small RNAs, ~21 and ~24 nt (FIG. 2C). In both *Drosophila* and *C. elegans*, Dicer requires ATP for efficient production of both siRNAs (Zamore et al. 2000; Bernstein et al. 2001; Nykanen et al. 2001) and miRNAs (Hutvagner et al. 2001; Ketting et al. 2001). Consistent with the idea that both classes of small RNAs are produced by plant orthologs of Dicer, efficient production of both the ~21-nt and the ~24-nt small RNAs in wheat germ extract required ATP (FIG. 2D).

Although small, silencing-associated RNAs in plants are commonly called siRNAs, and synthetic siRNA duplexes initiate plant RNA silencing (Klahre et al. 2002), plant small RNAs have not been demonstrated to be double-stranded RNAs with 2-nt, 3' overhanging ends and 3'-hydroxyl termini. Such attributes reflect the unique production of siRNAs by members of the Dicer family of ribonuclease III enzymes. To determine if the small RNAs generated from dsRNA in wheat germ extracts were bona fide siRNAs, we analyzed their structure. Uniformly 32P-radiolabeled dsRNA was incubated in wheat germ extract, deproteinized, and fractionated by gel filtration to resolve single-stranded from double-stranded siRNA (Nykanen et al. 2001). Both classes of small RNA products of the in vitro wheat germ reaction comigrated with a synthetic siRNA duplex and with *Drosophila* siRNA duplexes generated by processing dsRNA in *Drosophila* embryo lysate (FIG. 2E). Therefore, the small RNAs generated by incubating dsRNA in wheat germ extract are double-stranded.

Next, we examined the end structure of the small RNAs. Treatment of 5'-32P-radiolabeled, synthetic siRNA duplexes with the single-stranded RNA-specific nucleases T1 and RNase A removes the 2-nt, 3' overhanging ends typical of siRNAs, generating 1-nt and 2-nt shorter RNAs. In a denaturing polyacrylamide gel, such nuclease products of siRNAs migrate faster, because they contain 3'-phosphates (diagramed in FIG. 2F). When synthetic 25-nt duplexes with 2-nt, 3' overhangs were digested with T1 and RNase A, the expected 24-nt and 23-nt, 3' phosphorylated products were generated (FIG. 2G). The small RNAs produced by incubation of dsRNA in the wheat germ extract are a mixture of ~21-nt and 24-25-nt species. Digestion of this mixture with single-stranded nucleases produced a faster-migrating population of RNA species whose length distribution is consistent with the original mixture having the single-stranded overhangs and double-stranded body characteristic of siRNAs (FIG. 2G). Both size classes of small RNAs produced upon incubation of dsRNA in wheat germ extract have 2',3'-hydroxyl and 5' monophosphate termini (data not shown). In sum, the small RNAs have all the hallmarks of the products of Dicer-mediated cleavage of dsRNA. It is concluded that they are bona fide siRNAs.

Example III: Different Dicer-Like Enzymes Produce Each Class of siRNA

There are at least two mechanisms by which long dsRNA could be converted in plants into distinct size classes of small RNAs. Local dsRNA sequence might determine siRNA length, irrespective of which Dicer ortholog cleaves the dsRNA. In this case, we anticipate that the two classes of small RNAs would have distinct sequence compositions. Instead, only the 5' ends of the two classes show sequence bias (FIG. 1B). An alternative explanation is that different Dicer orthologs produce each class. Both the *Arabidopsis* and rice genomes encode at least four different Dicer-like proteins, including the *Arabidopsis* protein CARPEL FAC- TORY/SHORT INTEGUMENTS-1 (CAF). The number of wheat Dicer orthologs is presently unknown, because the hexaploid wheat genome remains to be sequenced.

Figure 3C:
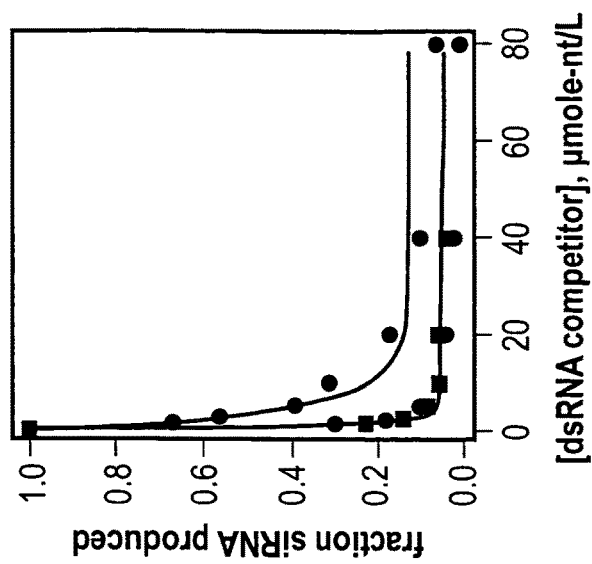
FIGS. 3A-3C. The two classes of plant siRNAs are produced by different enzymes.
Figure 3B:
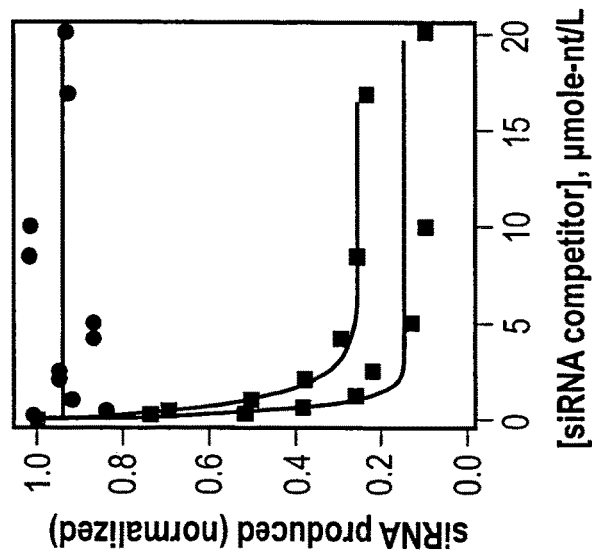
Figure 3A:
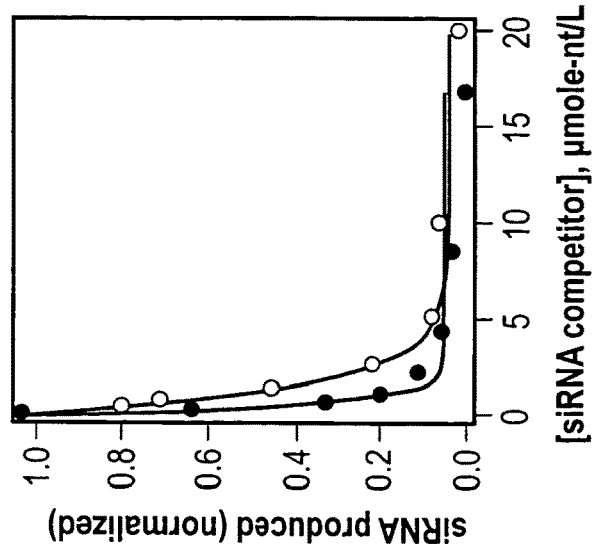

*Drosophila* Dicer binds tightly to siRNAs (P. D. Zamore and B. Haley, unpubl.). Therefore, we reasoned that different Dicer orthologs might be differentially inhibited by their products, siRNAs. We tested the ability of 21-nt and 25-nt synthetic siRNA duplexes to inhibit the production of siRNAs in *Drosophila* embryo lysates and the production of the two distinct classes of siRNA in wheat germ extract. *Drosophila* Dicer produces siRNAs 21-22 nt long. *Drosophila* Dicer was inhibited more strongly by a 21-nt siRNA duplex than by a 25-mer (FIG. 3A). Conversely, production of 24-25-nt siRNAs by wheat germ extract was inhibited more strongly by an ~25-nt synthetic siRNA duplex competitor than a 21-mer (FIG. 3B). These results are consistent with the idea that the authentic siRNA product of Dicer should bind more strongly to its active site than an siRNA of an inauthentic length. Surprisingly, production of the ~21-nt siRNAs was completely refractory to inhibition by either 21-nt or 25-nt synthetic siRNA duplexes, at siRNA concentrations as high as 800 nM (FIG. 3B). The simplest explanation for these data is that a different Dicer-like enzyme generates each class of siRNA and that the enzyme responsible for producing the 24-25-nt siRNAs is strongly inhibited by its siRNA product, whereas the enzyme that produces the ~21-nt siRNAs is not inhibited by siRNA product at the concentrations tested. An alternative explanation is that the concentration of the enzyme that produces the ~21-mers is higher than the highest concentration of inhibitor we tested, 800 nM. For this to be true, the enzyme would need to be present at micromolar concentration in the extract, which seems unlikely, as it would then correspond to ~1% of total protein. The finding that production of both classes of siRNAs were equally and strongly inhibited by long dsRNA competitor (FIG. 3C) also supports an argument against this view. If the enzyme that generates the 21-mers were present in the extract at very high concentration, its activity should not have been competed by the same concentrations of long dsRNA competitor that saturate the enzyme that produces the 24-25-nt products. It is concluded that each class of siRNA is produced by the ATP-dependent, endonucleolytic cleavage of dsRNA by a different Dicer ortholog.

Example IV: An RNA-Dependent RNA Polymerase Activity in Wheat Germ Extracts

Genetic evidence implicates an RNA-dependent RNA polymerase (RdRP) in PTGS triggered by transgenes expressing sense mRNA (S-PTGS; Dalmay et al. 2000; Mourrain et al. 2000). Plant RdRPs have been proposed to generate dsRNA from aberrantly expressed single-stranded RNA, thereby leading to the production of siRNAs that silence that RNA (Vaucheret et al. 2001). No direct biochemical evidence has yet been presented demonstrating that such a pathway is plausible.

Figure 4:
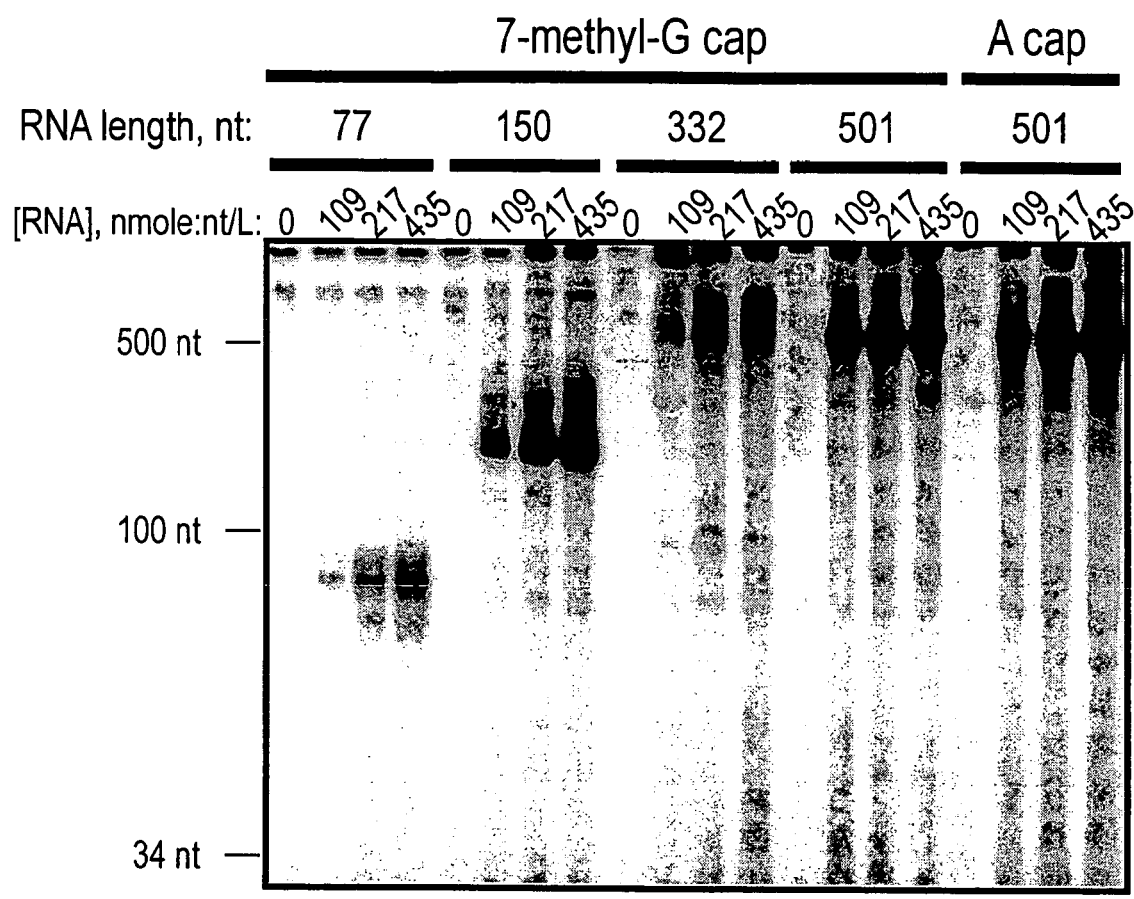
FIG. 4. Wheat germ extract contains an RdRP activity. Single-stranded RNA of the indicated size and cap structure was incubated in wheat germ extract for 3 hours in the presence of ATP, CTP, GTP, and α-32P-UTP. The products of the reaction were analyzed by denaturing polyacrylamide gel electrophoresis.
Figure 5A:
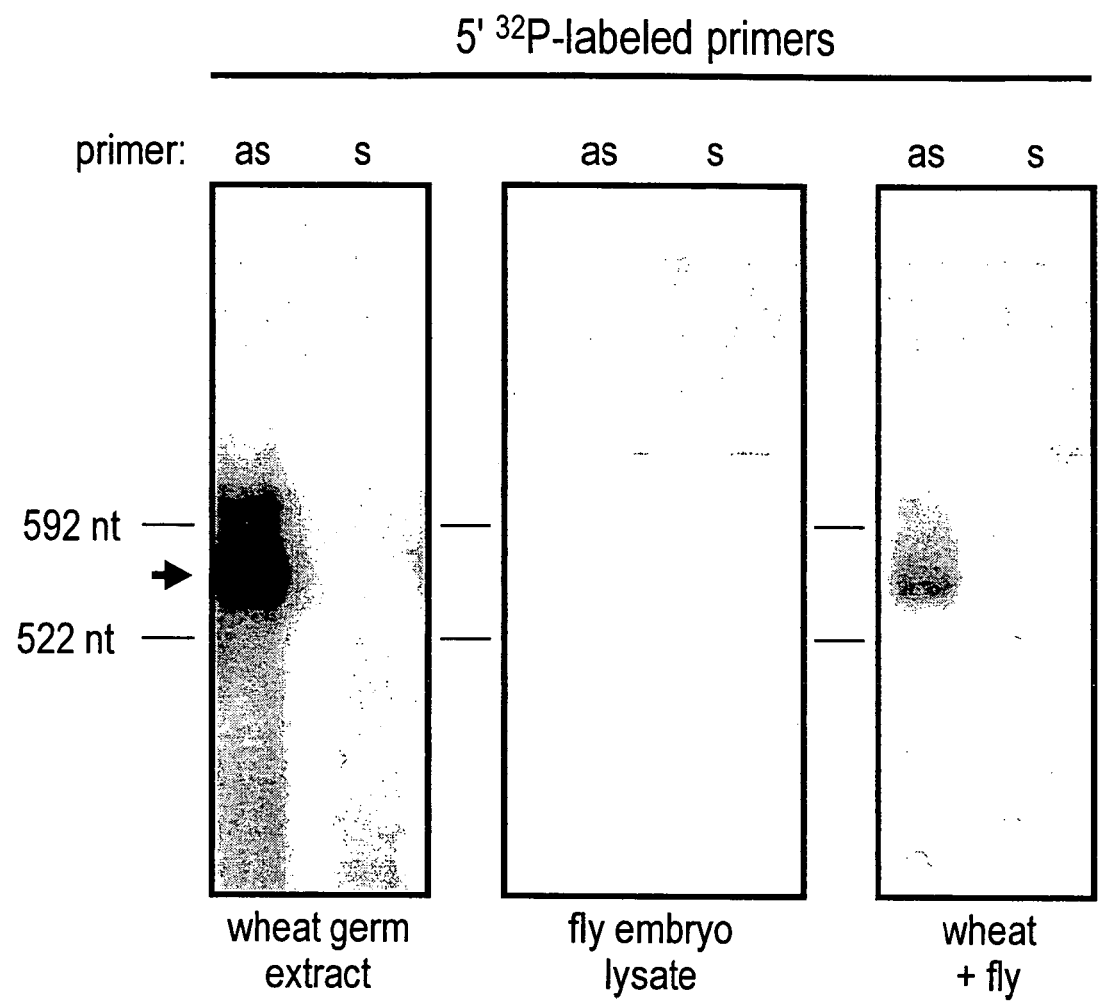
FIGS. 5A-5C. Characterization of the wheat RdRP activity.

Wheat germ extracts contain an RdRP activity (FIG. 4). Increasing concentrations of single-stranded RNA were incubated with the extract and ribonucleotide triphosphates, including [alpha]-32P-UTP. Single-stranded RNA ranging from 77 to 501 nt, either bearing a 7-methyl-G(5')ppp(5')G or an A(5')ppp(5') cap structure, all led to the incorporation of 32P into RNA with approximately the same length as the exogenous, nonradioactive single-stranded RNA (FIG. 4). These radioactive RNAs correspond to bona fide complementary RNA (cRNA) generated by an RdRP that copied the single-stranded RNA by initiating RNA synthesis at the extreme 3' end of the exogenous template RNA (data not shown). In theory, these newly radioactive RNAs could have arisen by transfer of radiolabel to the input RNA itself. This type of label transfer had previously been observed when similar experiments were performed using *Drosophila* embryo lysates, but not with wheat germ extract. Instead, the 32P-RNA represents newly synthesized cRNA produced by a wheat enzyme using exogenous single-stranded RNA as a template in the absence of an exogenous nucleic acid primer In addition to copying single-stranded RNA into approximately full-length cRNA, RdRPs have also been reported to extend primers, using single-stranded RNA as a template (e.g., Schiebel et al. 1998). The RdRP activity or activities in wheat germ extract could similarly extend a 32P-radiolabeled primer (FIG. 5A), but only when the RNA primer was complementary (antisense) to the template RNA. Under identical conditions, no such primer-extension activity was detected in lysates of syncitial blastoderm *Drosophila* embryos, despite earlier reports to the contrary (Lipardi et al. 2001). RNA-dependent, RNA-primer-extension activity was detected, however, when wheat and fly extracts are mixed (FIG. 5A). In neither *Drosophila* embryo lysate nor wheat germ extract can we detect primer extension of a single-stranded RNA template using a 21-nt siRNA duplex rather than a 21-nt antisense primer.

Figure 5B:
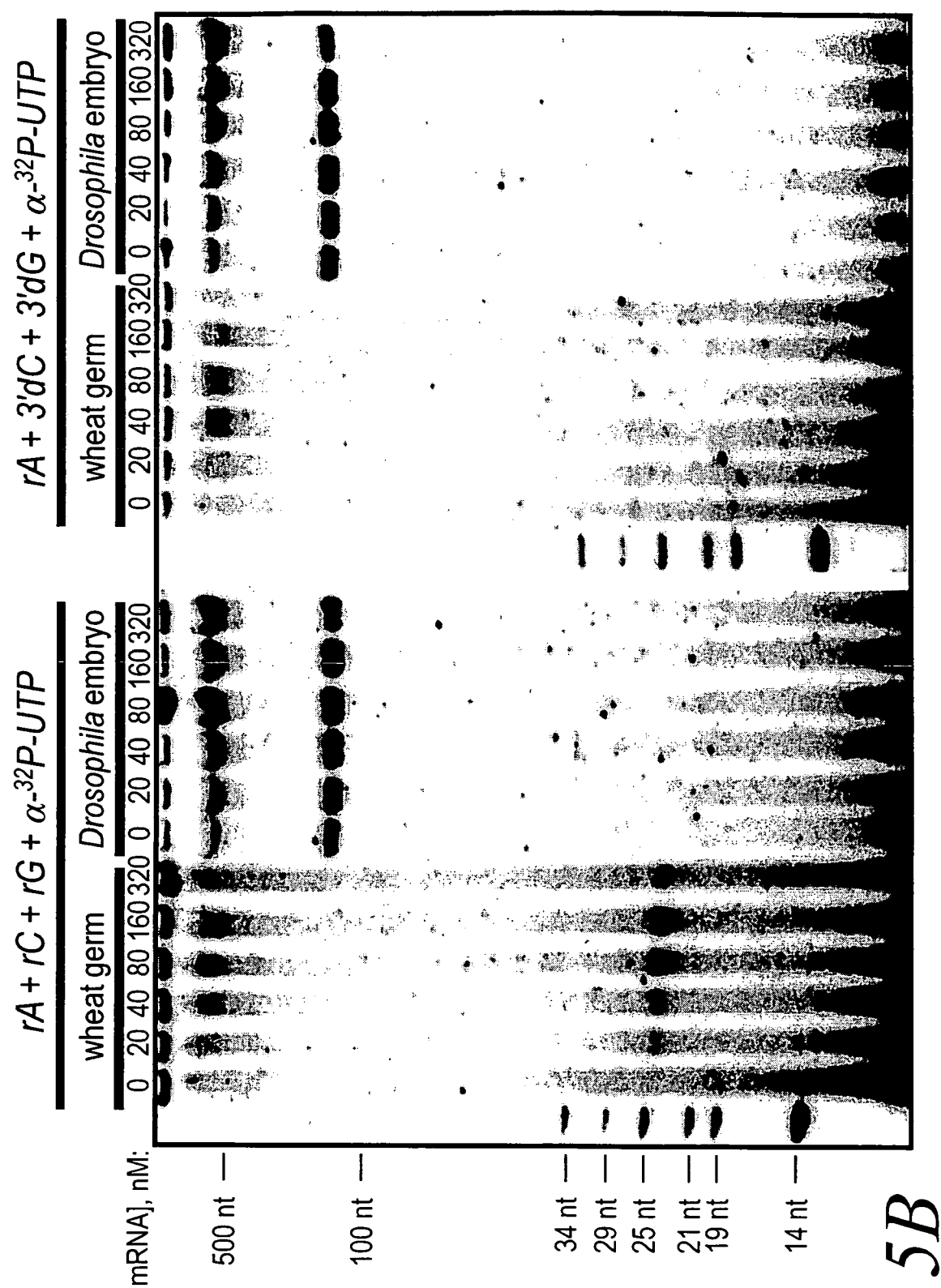

It is proposed that aberrant single-stranded RNA triggers silencing in plants when it serves as a template for the production of cRNA, generating dsRNA, which can then be cleaved by Dicer into siRNA duplexes. These data suggest that such copying does not require primers, but is triggered merely by an exceptionally high concentration of single-stranded RNA. To test if high concentrations of single-stranded mRNA could lead to the production of siRNAs, the RdRP reactions were repeated using a 2.7-kb single-stranded firefly luciferase mRNA. Increasing concentrations of the mRNA were incubated in either wheat germ extract or *Drosophila* embryo lysate in the presence of ATP, CTP, GTP, and [alpha]-32P-UTP, and examined for the production of 21-25-nt radioactive RNAs. FIG. 5B (left) shows that when the incubations were performed in wheat germ lysates, a single class of small RNA, ~24 nt long, was produced with increasing concentrations of the exogenous, single-stranded template RNA. No such radioactive product was observed in *Drosophila* embryo lysates, but it is noted that these lysates contain endogenous UTP, which may preclude detection of 32P small RNAs. To test if the radiolabeled ~24-nt products were generated by the de novo synthesis of RNA, the experiment was repeated, replacing CTP and GTP with 3'-deoxy CTP and 3'-deoxy GTP, inhibitors of RNA synthesis. In the presence of these inhibitors, no radioactive small RNAs were observed in the wheat reaction (FIG. 5B, right). Thus, single-stranded RNA can trigger in wheat germ extract the de novo synthesis of ~24-nt small RNAs.

Notably, the production of 21-nt RNAs was not detected in this assay. The assay should have detected such 21-nt small RNAs if they were present at $\frac{1}{10}$ the concentration of the ~24-mers, but we would be unlikely to detect them far below this threshold. Experiments with double-stranded RNA suggest that the 21-mers are produced in wheat at about ¼ the rate of the 24-25-nt small RNAs (FIG. 2). Thus, the production of dsRNA by the RdRP activity may be coupled to the production of the longer class of small RNAs. It is noted that such coupling does not imply that production of ~24-nt siRNAs from exogenous dsRNA requires the participation of an RdRP. It is proposed that dsRNA generated by RdRP copying of single-stranded RNA is preferentially processed by a wheat Dicer ortholog that produces long siRNAs, perhaps because the two proteins are physically linked.

Figure 5C:
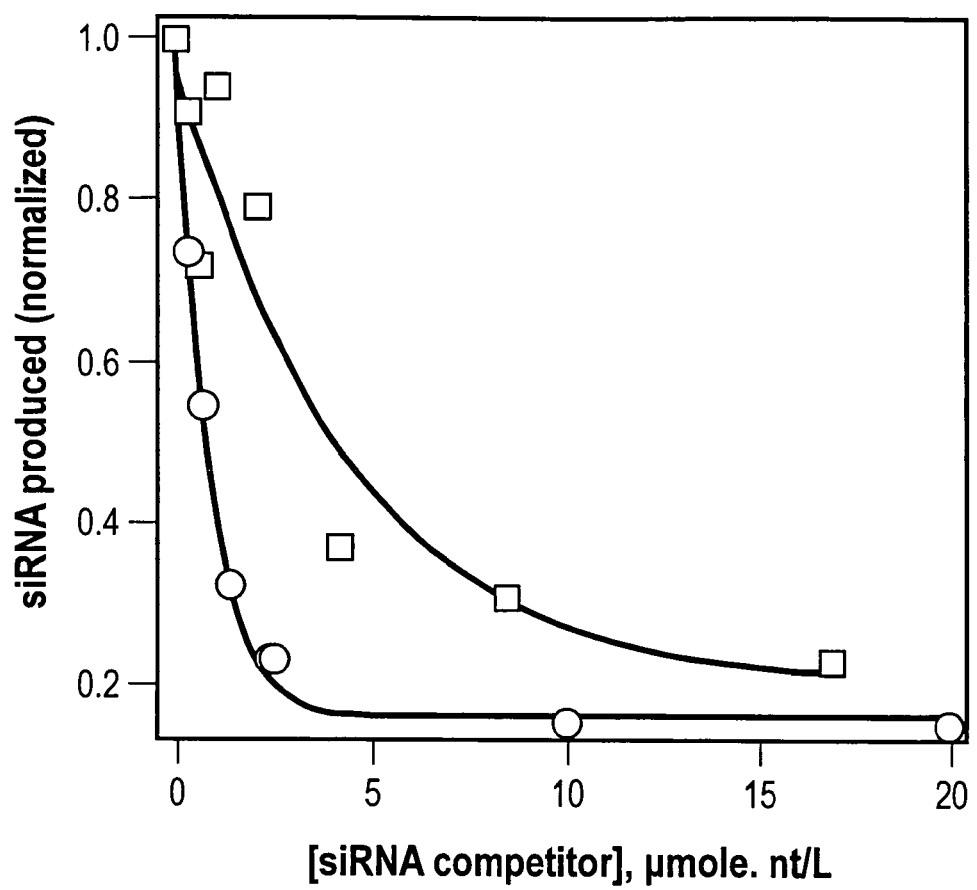

The question of whether the ~24-nt RNAs synthesized in the RdRP reactions are actual products of Dicer cleavage of dsRNA was next addressed. Production of wheat 24-25-nt siRNAs from 32P-radiolabeled dsRNA is efficiently inhibited by synthetic siRNA duplexes; 25-nt synthetic siRNA duplexes are more potent inhibitors than 21-nt duplexes (FIG. 3B). Therefore, an experiment was conducted to determine if production of the ~24-nt small RNAs in the RdRP reactions was similarly inhibited by synthetic siRNA duplexes. FIG. 5C shows that the production of ~24-nt small RNAs in the RdRP reactions programmed with a 2.7-kb single-stranded RNA template was inhibited by synthetic siRNA duplexes. Like the production of 24-25-nt siRNAs from exogenous dsRNA, production of the de novo synthesized ~24-mers was inhibited to a greater extent by 25-nt synthetic siRNA duplexes than by 21-nt duplexes (FIG. 5C). Half-maximal inhibition of small RNA production in the RdRP-dependent reactions occurred at roughly the same concentration of synthetic siRNA duplex as inhibition of the processing of 32P dsRNA (cf. FIGS. 5C and 3B). It is concluded that in wheat germ extract, exogenous single-stranded RNA provides the template for the synthesis of cRNA by an RdRP and that the resulting template-RNA:cRNA hybrid is then preferentially cleaved into ~24-nt siRNAs by a Dicer-like enzyme.

Example V: miRNAs Act as siRNAs in Plants

In addition to siRNAs, another class of small RNAs, microRNAs (miRNAs), has been detected in plants (Llave et al. 2002a; Park et al. 2002; Reinhart et al. 2002). Like their animal counterparts, plant miRNAs are generated by a Dicer family member, CAF. miRNAs are encoded in stem-loop precursor RNAs that are cleaved by CAF into 21-24-nt single-stranded small RNAs (Park et al. 2002; Reinhart et al. 2002). Exogenous miRNA precursors were not faithfully processed into mature miRNAs in wheat germ extract (data not shown). Instead, in vitro transcribed pre-miRNAs were cleaved into small RNAs too long to correspond to authentic, mature miRNAs. Perhaps the Dicer ortholog responsible for miRNA maturation in wheat—presumably wheat CAF—is absent from wheat germ extracts. In *Arabidopsis*, CAF transcripts that encode a protein with a nuclear localization signal have been reported, suggesting that CAF protein may be nuclear (Jacobsen et al. 1999). Because wheat germ extracts are essentially cytoplasm, nuclear CAF might not be present in the extract.

Plant miRNAs differ from animal miRNAs in that there are corresponding mRNA sequences in the *Arabidopsis* and rice genomes with significant complementarity to miRNA sequences (Llave et al. 2002a,b; Reinhart et al. 2002; Rhoades et al. 2002). The high degree of complementarity between 14 recently analyzed plant miRNAs and specific families of developmentally important plant mRNAs led to the proposal that plant miRNAs direct developmentally controlled mRNA destruction (Rhoades et al. 2002). That is, after the plant miRNAs are generated by the cleavage of pre-miRNAs by CAF, they enter the RNAi pathway and function as siRNAs. In contrast, animal miRNAs are thought to act as translational repressors (for review, see Ruvkun 2001). An untested feature of this proposal is that an RNAi-like pathway in plants tolerates the three to four mismatches sometimes observed between an miRNA and its predicted mRNA target.

Figure 6A:
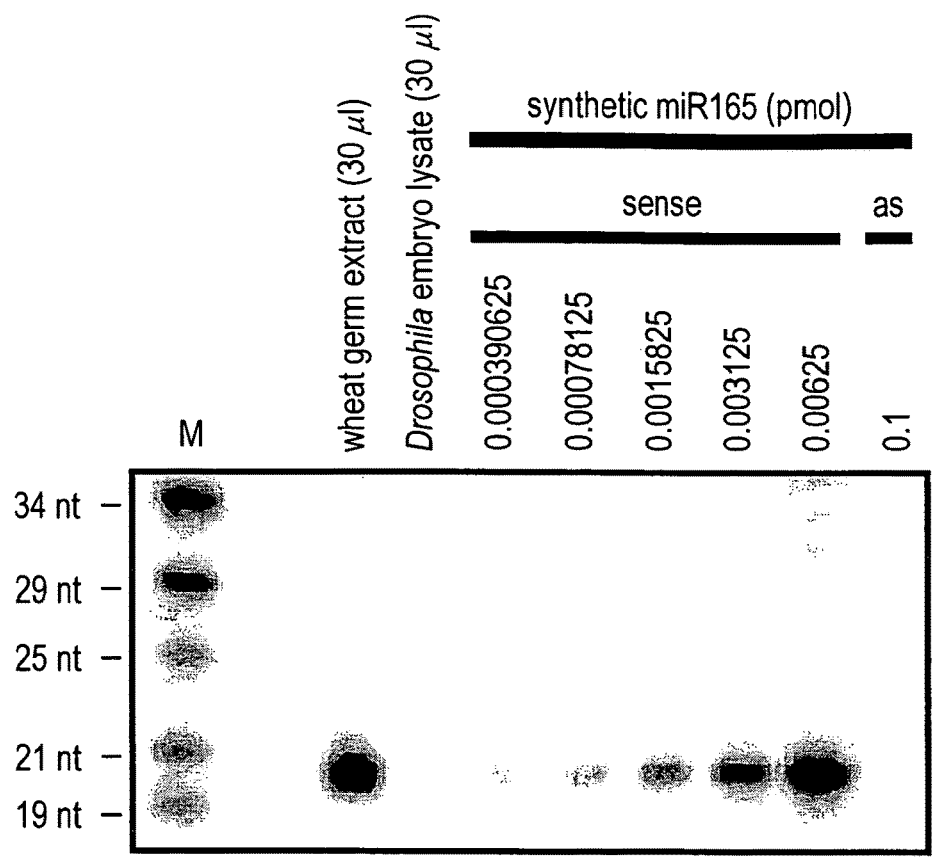
FIGS. 6A-6C. miR165/166 in wheat germ extract.

If plant miRNAs are endogenous mediators of RNAi, then wheat germ extracts should contain miRNA-programmed complexes that specify endonucleolytic cleavage of corresponding target RNAs. In particular, miR165 has been proposed to down-regulate PHV and PHABULOSA (PHB) mRNA expression in *Arabidopsis* by an RNAi-like mechanism (Rhoades et al. 2002). PHV and PHB encode homeodomain-leucine zipper transcription factors implicated in the perception of radial position in the shoot tissues that give rise to leaves (McConnell and Barton 1998; McConnell et al. 2001). Dominant phv and phb mutations alter a single amino acid (glycine→glutamic acid) in the sterol/lipid-binding domain of the proteins, suggesting that the mutant phenotype results from a change in the function of PHV and PHB (McConnell and Barton 1998; McConnell et al. 2001). However, the discovery of plant miRNAs complementary to this site in PHV led to the suggestion that the molecular basis of the dominance is the persistence of PHV and PHB expression at developmental stages when these mRNAs are normally destroyed (Rhoades et al. 2002). This hypothesis is consistent with both the increased overall levels of PHB mRNA in the dominant mutant and the increased activity of a dominant mutant phb mRNA on the abaxial, rather than the adaxial, domain of the leaf primordium (McConnell and Barton 1998; McConnell et al. 2001).

miR165 or miR166 is present in wheat germ extracts (FIG. 6A). miR165 and miR166 differ by a single C-to-U transition that decreases the complementarity of miR166 to PHV and PHB by changing a G:C base pair to a G:U wobble. Rice (*Oryza*) is the sequenced genome most closely related to wheat. Although the rice genome encodes no miR165 homolog, it encodes six copies of miR166 (Reinhart et al. 2002). Because the Northern hybridization conditions used herein cannot distinguish between miR165 and miR166, the endogenous wheat miRNA is referred to as miR165/166.

Figure 6B:
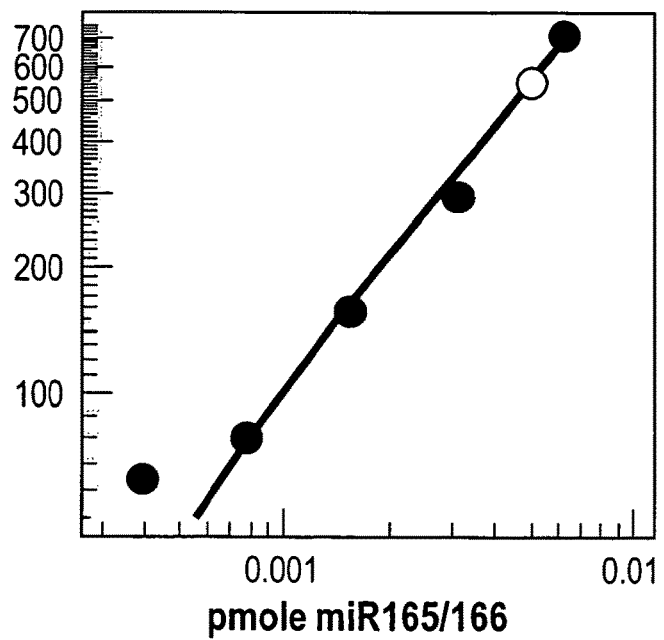
Figure 6C:
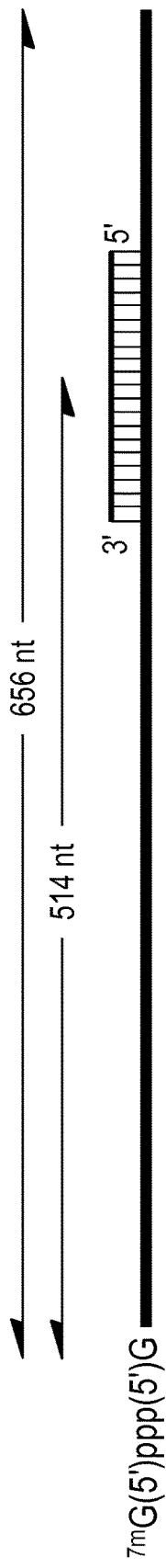
Figure 7A:
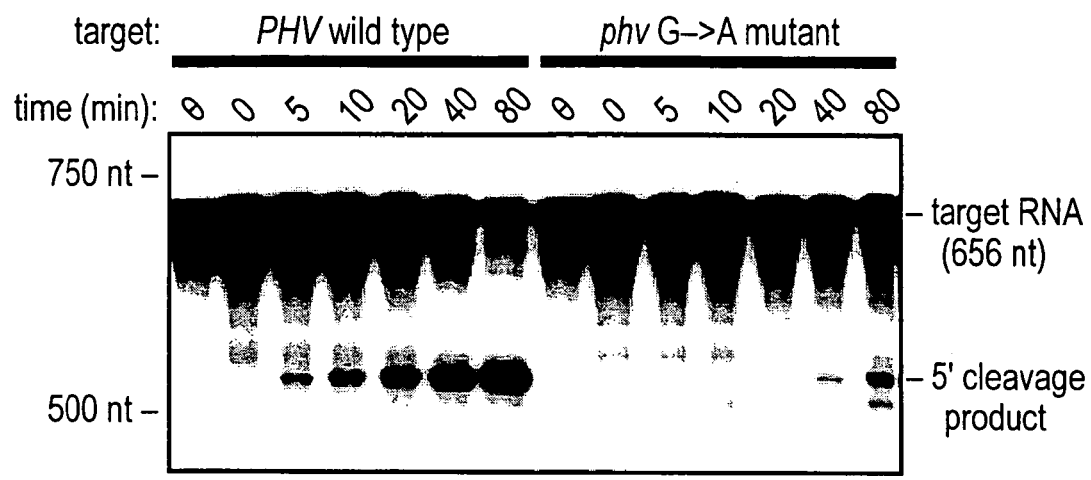
FIGS. 7A-7C. An endogenous wheat nuclease efficiently cleaves wild-type but not mutant PHV target RNAs.
Figure 7B:
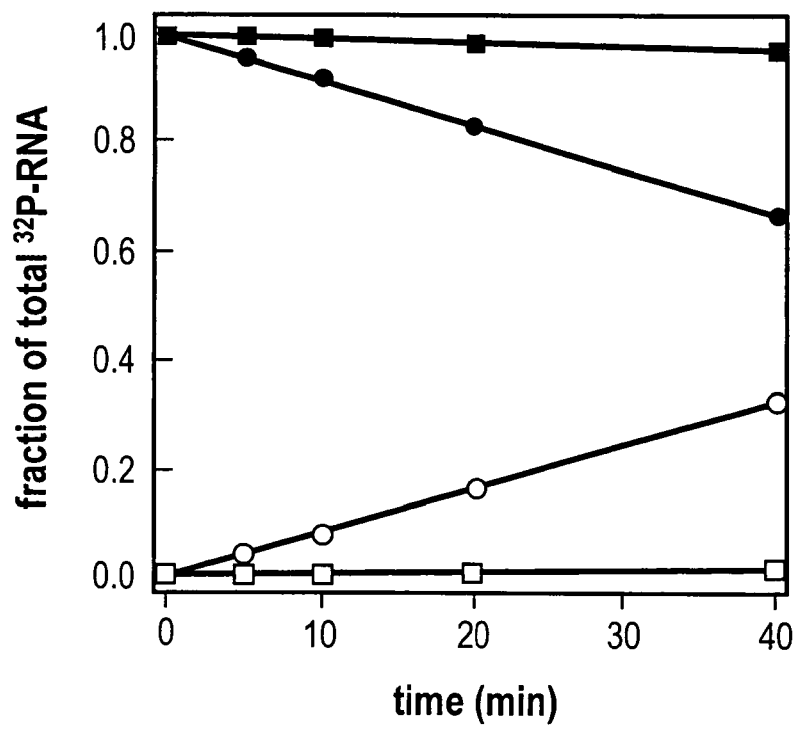

To begin to test the hypothesis that plant miRNAs function to regulate target gene expression by an RNAi-like mechanism, target RNAs were prepared encoding a portion of the wild-type sequence of *Arabidopsis* PHV or the dominant G→A point mutation, which falls within the PHV sequences proposed to pair with miR165/166. The target RNAs and relevant miRNAs are shown in FIG. 6C. 5'-radiolabeled target RNAs were incubated with wheat germ extract, then analyzed on a denaturing sequencing gel. In the absence of any other exogenous RNA, the wild-type PHV target RNA, but not the dominant G→A mutant, was efficiently cleaved within the region complementary to miR165/166 (FIG. 7A,B). This 21-nt region is identical in PHV and PHB, and a target RNA that contained sequence from the *Arabidopsis* PHB mRNA was also cleaved within the sequences complementary to miR165/166 upon incubation in the wheat germ extract (data not shown). In the RNAi pathway, a key feature of small RNA-directed target destruction is that pretreatment with the single-stranded nucleic acid-specific enzyme, micrococcal nuclease, abolishes RISC activity (Hammond et al. 2000). Cleavage of the PHV target RNA was likewise abolished by pretreatment of the extract with micrococcal nuclease (data not shown), consistent with the view that miR165/166 acts as a guide to direct target cleavage. The difference in cleavage rate between wild-type and mutant target RNAs, which differ only at a single nucleotide, was >14-fold (FIG. 7B). Thus, the resistance of the mutant phv RNA to cleavage by an endogenous RNAi-like nuclease can explain why the mutation is dominant.

Figure 7C:
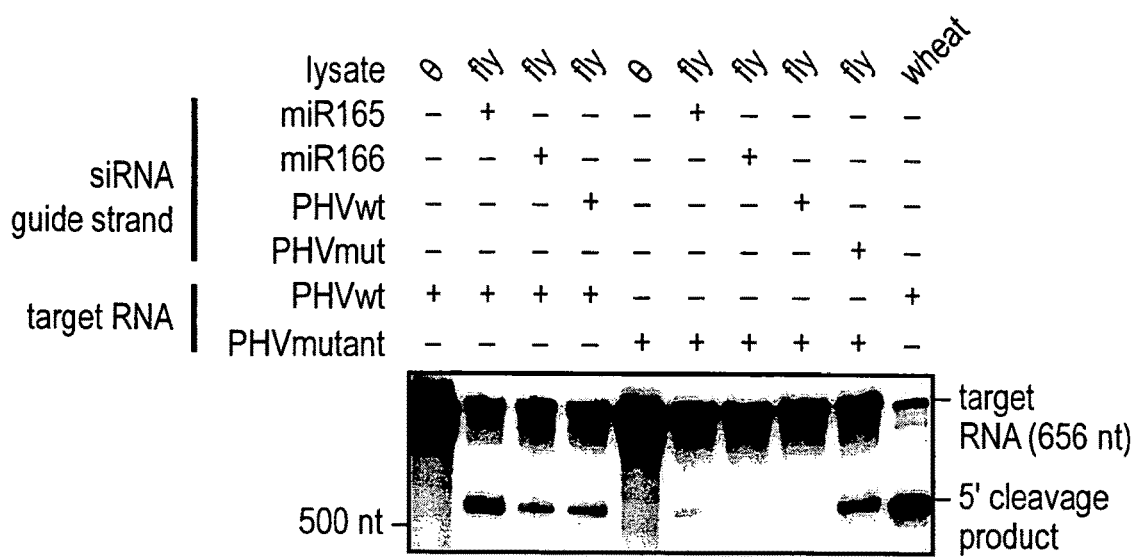
Figure 8:
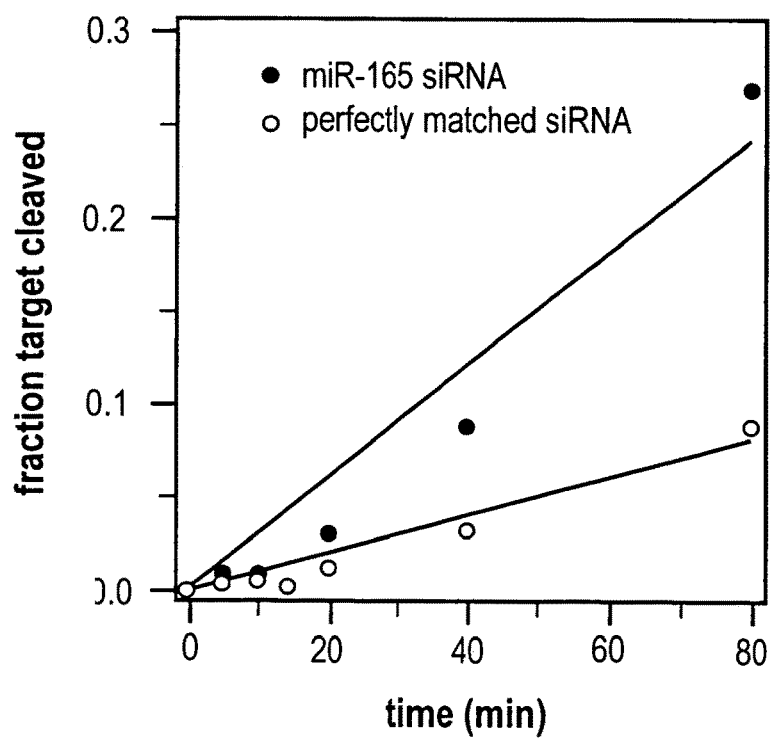
FIG. 8. Quantification of the fraction of target mRNA cleaved by siRNA having perfect complementarity to target versus siRNA having two mismatched with target (miR 165 siRNA).

Next, cleavage of the PHV target RNA by various siRNAs was analuzed in *Drosophila* embryo lysate (FIG. 6C). An siRNA with perfect complementarity to the site predicted to pair with miR165/166 and an siRNA duplex in which one strand had the sequence of miR165 or miR166 directed cleavage of the PHV target RNA, yielding the predicted 514-nt 5' cleavage product (FIG. 7C). None of these three siRNAs efficiently cleaved the PHV mutant target (FIG. 7C). Quantification of the cleavage mediated by the siRNA with perfect complementarity as compared to that mediated by miR165 demonstrates that miR165 more efficiently mediates target cleavage. This is presumed to be due to the fact that miR 165 forms two G:U wobble base pairs with the target mRNA, one at position 1 and one at position 17 (with respect to the 5' end of the antisense siRNA strand) (FIG. 8).

The failure of the miR165-siRNA duplex to cleave mutant PHV was a direct consequence of its reduced complementarity to the target RNA at position 6 (with respect to the 5' end of the antisense siRNA strand), because an siRNA with perfect complementarity to the mutant sequence (FIG. 6B) efficiently cleaved the mutant RNA (FIG. 7C). The 5' cleavage product produced in the siRNA-programmed RNAi reactions comigrated with that produced when the PHV target RNA was incubated in wheat germ extract without exogenous siRNA (FIG. 7C).

The simplest explanation for the sequence-specificity of the nuclease is that it is guided by miR165/166: cleavage requires a nucleic acid component, occurs at the same site on the PHV target RNA as directed by an siRNA duplex with the sequence of miR165 or miR166 in *Drosophila* embryo lysate, and, like the siRNA, is inefficient with the G→A mutant phv RNA. In the RNAi pathway, an siRNA-programmed endonuclease complex is called an RISC (Hammond et al. 2000). These data suggest that wheat miR165/166 is in an RISC, supporting the proposal that plant miRNAs regulate expression of their mRNA targets by endogenous RNAi.

Example VI: miR165/166 Directs Multiple Rounds of Target Cleavage

The next question addressed was whether the miR165/166-programmed RISC acts as an enzyme. Quantitative Northern hybridization demonstrates that the wheat germ extract reactions contained 0.083 nM miR165/166 (FIG. 6B). The target RNA concentration in these reactions was 5 nM, and more than half the target RNA was destroyed in 80 min (FIG. 7A). Thus, each miR165/166 RNA directed cleavage of ~30 target RNA molecules. Therefore, the miR165/166-programmed RISC is a multiple-turnover enzyme.

Discussion

The above data show that wheat germ extracts recapitulate in vitro many aspects of RNA silencing in plants. Wheat germ extracts convert exogenous dsRNA into two distinct classes of small RNAs. Detailed analysis of these small RNAs indicates that they are bona fide siRNAs. Thus, plant siRNAs are derived directly from longer dsRNA, just as in animals. The data indicate that distinct Dicer-like enzymes generate the two functionally distinct classes of siRNAs. Cloned endogenous small RNAs from *Arabidopsis* likewise form two distinct length classes, whose 5' ends indicate that they are made by distinct enzymes. An alternative view, that one or more Dicer-like enzymes may generate both classes of small RNAs, with the different lengths a byproduct of local sequence context, is not consistent with the above observation that production of 24-25-nt RNAs in wheat germ extract was inhibited by synthetic siRNA duplexes, whereas ~21-nt siRNA production was not. If the production of siRNAs is tightly coupled to the assembly of downstream effector complexes, then their production by different Dicer orthologs may ensure that the two classes of siRNAs function in different cellular pathways (see also Hamilton et al. 2002).

A hallmark of PTGS in plants and RNAi in nematodes is the spreading of silencing signals along the length of the mRNA target. In plants, spreading occurs in both the 5' and 3' directions and requires the putative RdRP gene, SGS2. Spreading is observed even when silencing is initiated by a single siRNA sequence (Klahre et al. 2002). One hypothesis is that 5' spreading is initiated by the antisense siRNA strand priming copying of the target mRNA by an RdRP, thereby producing dsRNA. 3' spreading cannot be explained by such a mechanism. Both 5' and 3' spreading might instead be catalyzed by the conversion of mRNA fragments into dsRNA by an RdRP that initiates synthesis at the 3' end of the two fragments generated when an RISC cleaves the target RNA. This dsRNA would then be cleaved by a Dicer-like enzyme to produce secondary siRNAs (Lipardi et al. 2001; Sijen et al. 2001). Such RNA synthesis would occur without the involvement of a primer. The above data demonstrate that exogenous single-stranded RNA is copied into cRNA in the extract by a wheat RdRP that acts without the aid of an exogenous primer. The resulting dsRNA is cleaved preferentially into the longer class of siRNAs, suggesting the RdRP is physically linked to a specific Dicer ortholog. The specific biochemical function of the 24-25-nt siRNAs generated in this reaction remains to be determined.

miRNAs Function as siRNAs in Plants

The above data further show that miRNAs in plants function in much the same way that siRNA duplexes function in *Drosophila* and humans: as guides for an endonuclease complex. Each endonuclease complex can catalyze multiple rounds of target cleavage, indicating that the miRNA is not consumed in the reaction. Entry of a miRNA into a multiple-turnover RNAi enzyme complex is not unprecedented; in human cells, the miRNA let-7 is a component of an RISC, although the human genome does not appear to contain any mRNA sequences with sufficient complementarity to be cleaved by this RISC (Hutvágner and Zamore 2002). Like the plant miR165/166-programmed RISC, the human let-7-programmed RISC can catalyze multiple rounds of target cleavage.

Additional support for the idea that plant miRNAs direct cleavage of complementary mRNA targets comes from the work of Carrington and colleagues, who recently showed that a family of *Arabidopsis* mRNAs encoding SCARE-CROW-LIKE (SCL) transcription factors is cleaved by an RNAi-like process directed by miR171, an miRNA that is fully complementary to its mRNA targets, unlike miR165/166 (Llave et al. 2002b). Like wheat miR165/166, *Arabidopsis* miR171 appears to direct the endonucleolytic cleavage of its target mRNAs. In this respect, miR171 functions as if it were a single-stranded siRNA. Single-stranded siRNAs can trigger RNAi in both *Drosophila* and mammalian cell extracts and in vivo in HeLa cells (Martinez et al. 2002a; Schwarz et al. 2002), although much higher concentrations of single-stranded siRNA is required than for duplex (Schwarz et al. 2002). Furthermore, an individual human RISC contains only one strand of the exogenous siRNA duplex used to trigger RNAi (Martinez et al. 2002a).

The observation that, in *Drosophila* embryo lysate, an siRNA with the sequence of miR165, which contains three mismatches with its target mRNA, is at least as potent as an siRNA with perfect complementarity to the same target sequence, demonstrates that mismatches per se do not block target cleavage. Rather, the specific position and sequence of siRNA:target RNA mismatches determine if they permit or disrupt RNAi. The data also suggest that miRNAs in plants evolved to optimize cleavage efficiency rather than maximize complementarity to their targets. It is predicted that three or four mismatches between an miRNA (or the guide strand of an siRNA duplex) and its target RNA, properly placed so as to still permit mRNA cleavage, will facilitate the release of cleaved target RNA from the RISC complex, thereby increasing the rate of enzyme turnover.

miRNA Function and the Spread of Silencing Signals Along a Silenced Sequence

Spreading of silencing signals along the length of a silenced mRNA sequence is a common feature of plant RNA silencing. Because miRNAs act as siRNAs, one might anticipate that they would also elicit spreading. However, miRNA-induced spreading is not consistent with the genetics of the PHV and PHB mutants; the very existence of a dominant PHV mutant excludes both 5' and 3' spreading. Spreading of the silencing signal—that is, the generation of new siRNAs 5' or 3' to the site of initial target cleavage—would produce siRNAs containing sequences common to both the wild-type and mutant PHV mRNAs. If such siRNAs were generated, they would direct destruction of the mutant PHV mRNA. In such a case, the PHV mutant could only have been recovered as a recessive, not a dominant allele. Genetic studies (McConnell et al. 2001) show that endonucleolytic cleavage of target RNAs by miRNA-directed RISC complexes does not trigger spreading in plants. This remains true even when the miRNA is the perfect complement of its mRNA target (Llave et al. 2002b).

How, then, can the well-documented spreading phenomenon observed for S-PTGS be reconciled with the absence of spreading in miRNA-directed target cleavage? It is proposed that plants contain two separate mechanisms for target mRNA destruction—endogenous mRNAs are regulated by endonucleolytic cleavage directed by miRNA-programmed RISC complexes, whereas exogenous silencing triggers, such as transgenes or viruses, might initiate successive cycles of siRNA-primed, RdRP-catalyzed dsRNA synthesis, followed by cleavage of the dsRNA into siRNAs by Dicer-like enzymes, a mechanism termed random degradative PCR (Lipardi et al. 2001). RISC complexes would play no role in the execution of target RNAs in this cycle. The observation that a single siRNA sequence can trigger 3' spreading (Klahre et al. 2002) is difficult to reconcile with a priming mechanism. Intriguingly, VIGS-mediated RNA silencing of endogenous genes is not associated with spreading of silencing into regions of the target sequence 5' or 3' to the initial silencing trigger (Vaistij et al. 2002), although such silencing clearly must involve siRNAs derived from viral dsRNA, not endogenous miRNAs.

An alternative hypothesis is that the absolute concentration of an RNA target might determine if the 5' and 3' cleavage fragments generated by target cleavage are converted into dsRNA by an RdRP. Only when the products of RISC-mediated target cleavage accumulate to a sufficiently high concentration would they serve as substrates for the RdRP and consequently trigger spreading. Experiments with polygalacturonase-silenced tomatoes support this view (Han and Grierson 2002). In these plants, siRNAs were produced from the silencing-inducing transgene but not the corresponding silenced endogene. The siRNAs were preferentially produced from the 3' end of the transgene, consistent with the idea that plant RdRPs act without aid of a primer. Furthermore, these authors detected mRNA degradation products consistent with endonucleolytic cleavage of the targeted polygalacturonase endogene. Thus, RISC-mediated cleavage per se does not appear to trigger spreading along the target RNA sequence. More likely, the endonucleolytic cleavage of transgenic mRNA produces a sufficiently high concentration of mRNA fragments to recruit an RdRP, resulting in the production of siRNAs from the 3' cleavage product. miRNA-directed cleavage of natural plant regulatory targets would not lead to spreading, because endogenous mRNA targets are not present at sufficiently high concentrations to recruit the RdRP. This model predicts that the putative RdRP SGS2 (SDE1) required for PTGS, will not be required for miRNA-directed destruction of endogenous mRNA targets. In fact, no developmental abnormalities have been reported for SGS2 mutants (Mourrain et al. 2000), including mutations likely to be strongly hypomorphic or functionally null (Dalmay et al. 2000), suggesting that plants lacking SGS2 protein have normal miRNA biogenesis and function.

REFERENCES

Beclin, C., Boutet, S., Waterhouse, P., and Vaucheret, H. 2002. A branched pathway for transgene-induced RNA silencing in plants. Curr. Biol. 12: 684-688.

Bernstein, E., Caudy, A. A., Hammond, S. M., and Hannon, G. J. 2001. Role for a bidentate ribonuclease in the initiation step of RNA interference. Nature 409: 363-366.

Billy, E., Brondani, V., Zhang, H., Muller, U., and Filipowicz, W. 2001. Specific interference with gene expression induced by long, double-stranded RNA in mouse embryonal teratocarcinoma cell lines. Proc. Natl. Acad. Sci. 98: 14428-14433.

Celotto, A. M. and Graveley, B. R. 2002. Exon-specific RNAi: A tool for dissecting the functional relevance of alternative splicing. RNA 8: 8-24.

Chiu, Y.-L. and Rana, T. M. 2002. RNAi in human cells: Basic structural and functional features of small interfering RNA. Mol. Cell 10: 549-561.

Cogoni, C. and Macino, G. 1999. Gene silencing in *Neurospora crassa* requires a protein homologous to RNA-dependent RNA polymerase. Nature 399: 166-169.

Dalmay, T., Hamilton, A., Rudd, S., Angell, S., and Baulcombe, D. C. 2000. An RNA-dependent RNA polymerase gene in *Arabidopsis* is required for posttranscriptional gene silencing mediated by a transgene but not by a virus. Cell 101: 543-553.

Djikeng, A., Shi, H., Tschudi, C., and Ullu, E. 2001. RNA interference in *Trypanosoma brucei*: Cloning of small interfering RNAs provides evidence for retroposon-derived 24-26-nucleotide RNAs. RNA 7: 1522-1530.

Elbashir, S. M., Harborth, J., Lendeckel, W., Yalcin, A., Weber, K., and Tuschl, T. 2001a. Duplexes of 21-nucleotide RNAs mediate RNA interference in mammalian cell culture. Nature 411: 494-498.

Elbashir, S. M., Lendeckel, W., and Tuschl, T. 2001b. RNA interference is mediated by 21- and 22-nucleotide RNAs. Genes & Dev. 15: 188-200.

Elbashir, S. M., Martinez, J., Patkaniowska, A., Lendeckel, W., and Tuschl, T. 2001c. Functional anatomy of siRNAs for mediating efficient RNAi in *Drosophila melanogaster* embryo lysate. EMBO J. 20: 6877-6888.

Erickson, A. H. and Blobel, G. 1983. Cell-free translation of messenger RNA in a wheat germ system. Methods Enzymol. 96: 38-50.

Fagard, M., Boutet, S., Morel, J.-B., Bellini, C., and Vaucheret, H. 2000. AGO1, QDE-2, and RDE-1 are related proteins required for post-transcriptional gene silencing in plants, quelling in fungi, and RNA interference in animals. Proc. Natl. Acad. Sci. 97: 11650-11654.

Grishok, A., Pasquinelli, A. E., Conte, D., Li, N., Parrish, S., Ha, I., Baillie, D. L., Fire, A., Ruvkun, G., and Mello, C. C. 2001. Genes and mechanisms related to RNA interference regulate expression of the small temporal RNAs that control *C. elegans* developmental timing. Cell 106: 23-34.

Hamilton, A. J. and Baulcombe, D. C. 1999. A species of small antisense RNA in posttranscriptional gene silencing in plants. Science 286: 950-952.

Hamilton, A., Voinnet, O., Chappell, L., and Baulcombe, D. 2002. Two classes of short interfering RNA in RNA silencing. EMBO J. 21: 4671-4679.

Hammond, S. M., Bernstein, E., Beach, D., and Hannon, G. J. 2000. An RNA-directed nuclease mediates post-transcriptional gene silencing in *Drosophila* cells. Nature 404: 293-296.

Hammond, S. M., Boettcher, S., Caudy, A. A., Kobayashi, R., and Hannon, G. J. 2001. Argonaute2, a link between genetic and biochemical analyses of RNAi. Science 293: 1146-1150.

Han, Y. and Grierson, D. 2002. Relationship between small antisense RNAs and aberrant RNAs associated with sense transgene mediated gene silencing in tomato. Plant J. 29: 509-519.

Hannon, G. J. 2002. RNA interference. Nature 418: 244-251.

Holen, T., Amarzguioui, M., Wiiger, M. T., Babaie, E., and Prydz, H. 2002. Positional effects of short interfering RNAs targeting the human coagulation trigger Tissue Factor. Nucleic Acids Res. 30: 1757-1766.

Hutvágner, G. and Zamore, P. D. 2002. A microRNA in a multiple-turnover RNAi enzyme complex. Science 297: 2056-2060.

Hutvagner, G., McLachlan, J., Pasquinelli, A. E., Balint, É., Tuschl, T., and Zamore, P. D. 2001. A cellular function for the RNA-interference enzyme Dicer in the maturation of the let-7 small temporal RNA. Science 293: 834-838.

Jacobsen, S. E., Running, M. P., and Meyerowitz, E. M. 1999. Disruption of an RNA helicase/RNase III gene in *Arabidopsis* causes unregulated cell division in floral meristems. Development 126: 5231-5243.

Kennerdell, J. R., Yamaguchi, S., and Carthew, R. W. 2002. RNAi is activated during *Drosophila* oocyte maturation in a manner dependent on aubergine and spindle-E. Genes & Dev. 16: 1884-1889.

Ketting, R. F., Fischer, S. E., Bernstein, E., Sijen, T., Hannon, G. J., and Plasterk, R. H. 2001. Dicer functions in RNA interference and in synthesis of small RNA involved in developmental timing in *C. elegans*. Genes & Dev. 15: 2654-2659.

Klahre, U., Crete, P., Leuenberger, S. A., Iglesias, V. A., and Meins, F., Jr. 2002. High molecular weight RNAs and small interfering RNAs induce systemic posttranscriptional gene silencing in plants. Proc. Natl. Acad. Sci. 99: 11981-11986.

Kooter, J. M., Matzke, M. A., and Meyer, P. 1999. Listening to the silent genes: Transgene silencing, gene regulation and pathogen control. Trends Plant Sci. 4: 340-347.

Lagos-Quintana, M., Rauhut, R., Lendeckel, W., and Tuschl, T. 2001. Identification of novel genes coding for small expressed RNAs. Science 294: 853-858.

Lagos-Quintana, M., Rauhut, R., Yalcin, A., Meyer, J., Lendeckel, W., and Tuschl, T. 2002. Identification of tissue-specific microRNAs from mouse. Curr. Biol. 12: 735-739.

Lau, N.C., Lim, L. P., Weinstein, E. G., and Bartel, D. P. 2001. An abundant class of tiny RNAs with probable regulatory roles in *Caenorhabditis elegans*. Science 294: 858-862.

Lee, R. C. and Ambros, V. 2001. An extensive class of small RNAs in *Caenorhabditis elegans*. Science 294: 862-864.

Lee, R. C., Feinbaum, R. C., and Ambros, V. 1993. The *C. elegans* heterochronic gene lin-4 encodes small RNAs with antisense complementarity to lin-14. Cell 75: 843-854.

Lee, Y., Jeon, K., Lee, J. T., Kim, S., and Kim, V. N. 2002. MicroRNA maturation: Stepwise processing and subcellular localization. EMBO J. 21: 4663-4670.

Li, W. X. and Ding, S. W. 2001. Viral suppressors of RNA silencing. Curr. Opin. Biotechnol. 12: 150-154.

Lipardi, C., Wei, Q., and Paterson, B. M. 2001. RNAi as random degradative PCR. siRNA primers convert mRNA into dsRNAs that are degraded to generate new siRNAs. Cell 107: 297-307.

Llave, C., Kasschau, K. D., Rector, M. A., and Carrington, J. C. 2002a. Endogenous and silencing-associated small RNAs in plants. Plant Cell 14: 1605-1619.

Llave, C., Xie, Z., Kasschau, K. D., and Carrington, J. C. 2002b. Cleavage of Scarecrow-Like mRNA targets directed by a class of *Arabidopsis* miRNA. Science 297: 2053-2056.

Mallory, A. C., Reinhart, B. J., Bartel, D., Vance, V. B., and Bowman, L. H. 2002. A viral suppressor of RNA silencing differentially regulates the accumulation of short interfering RNAs and micro-RNAs in tobacco. Proc. Natl. Acad. Sci. 99: 15228-15233.

Martens, H., Novotny, J., Oberstrass, J., Steck, T. L., Postlethwait, P., and Nellen, W. 2002. RNAi in Dictyostelium: The role of RNA-directed RNA polymerases and double-stranded RNase. Mol. Biol. Cell 13: 445-453.

Martinez, J., Patkaniowska, A., Urlaub, H., Lührmann, R., and Tuschl, T. 2002a. Single-stranded antisense siRNAs guide target RNA cleavage in RNAi. Cell 110: 563.

Martinez, L. A., Naguibneva, I., Lehrmann, H., Vervisch, A., Tchénio, T., Lozano, G., and Harel-Bellan, A. 2002b. Synthetic small inhibiting RNAs: Efficient tools to inactivate oncogenic mutations and restore p53 pathways. Proc. Natl. Acad. Sci. 99: 14849-14854.

Matzke, M. A., Matzke, A. J., Pruss, G. J., and Vance, V. B. 2001. RNA-based silencing strategies in plants. Curr. Opin. Genet. Dev. 11: 221-227.

McConnell, J. R. and Barton, M. K. 1998. Leaf polarity and meristem formation in *Arabidopsis*. Development 125: 2935-2942.

McConnell, J. R., Emery, J., Eshed, Y., Bao, N., Bowman, J., and Barton, M. K. 2001. Role of PHABULOSA and PHAVOLUTA in determining radial patterning in shoots. Nature 411: 709-713.

Mourelatos, Z., Dostie, J., Paushkin, S., Sharma, A. K., Charroux, B., Abel, L., Rappsilber, J., Mann, M., and Dreyfuss, G. 2002. miRNPs: A novel class of ribonucleoproteins containing numerous microRNAs. Genes & Dev. 16: 720-728.

Mourrain, P., Beclin, C., Elmayan, T., Feuerbach, F., Godon, C., Morel, J. B., Jouette, D., Lacombe, A. M., Nikic, S., Picault, N. et al. 2000. *Arabidopsis* SGS2 and SGS3 genes are required for posttranscriptional gene silencing and natural virus resistance. Cell 101: 533-542.

Nykänen, A., Haley, B., and Zamore, P. D. 2001. ATP requirements and small interfering RNA structure in the RNA interference pathway. Cell 107: 309-321.

Pal-Bhadra, M., Bhadra, U., and Birchler, J. A. 2002. RNAi related mechanisms affect both transcriptional and post-transcriptional transgene silencing in *Drosophila*. Mol. Cell 9: 315-327.

Park, W., Li, J., Song, R., Messing, J., and Chen, X. 2002. CARPEL FACTORY, a Dicer homolog, and HEN1, a novel protein, act in microRNA metabolism in *Arabidopsis thaliana*. Curr. Biol. 12: 1484-1495.

Parrish, S. and Fire, A. 2001. Distinct roles for RDE-1 and RDE-4 during RNA interference in *Caenorhabditis elegans*. RNA 7: 1397-1402.

Parrish, S., Fleenor, J., Xu, S., Mello, C., and Fire, A. 2000. Functional anatomy of a dsRNA trigger. Differential requirement for the two trigger strands in RNA interference. Mol. Cell 6: 1077-1087.

Pasquinelli, A. E., Reinhart, B. J., Slack, F., Martindale, M. Q., Kuroda, M. I., Maller, B., Hayward, D. C., Ball, E. E., Degnan, B., Muller, P. et al. 2000. Conservation of the sequence and temporal expression of let-7 heterochronic regulatory RNA. Nature 408: 86-89.

Plasterk, R. H. 2002. RNA silencing: The genome's immune system. Science 296: 1263-1265.

Reinhart, B. J., Slack, F. J., Basson, M., Pasquinelli, A. E., Bettinger, J. C., Rougvie, A. E., Horvitz, H. R., and Ruvkun, G. 2000. The 21-nucleotide let-7 RNA regulates developmental timing in *Caenorhabditis elegans*. Nature 403: 901-906.

Reinhart, B. J., Weinstein, E. G., Rhoades, M. W., Bartel, B., and Bartel, D. P. 2002. MicroRNAs in plants. Genes & Dev. 16: 1616-1626.

Rhoades, M. W., Reinhart, B. J., Lim, L. P., Burge, C. B., Bartel, B., and Bartel, D. P. 2002. Prediction of plant microRNA targets. Cell 110: 513-520.

Roberts, B. E. and Paterson, B. M. 1973. Efficient translation of tobacco mosaic virus RNA and rabbit globin 9S RNA in a cell-free system from commercial wheat germ. Proc. Natl. Acad. Sci. 70: 2330-2334.

Roignant, J.-Y., Carré, C., Mugat, B., Szymczak, D., Lepesant, J.-A., and Antoniewski, C. 2003. Absence of transitive and systemic pathways allows cell-specific and isoform-specific RNAi in *Drosophila*. RNA (In press).

Ruvkun, G. 2001. Molecular biology. Glimpses of a tiny RNA world. Science 294: 797-799.

Sambrook, J., Fritsch, E., and Maniatis, T. 1989. Molecular cloning: A laboratory manual, 2nd ed. Cold Spring Harbor Laboratory Press, Cold Spring Harbor, N.Y.

Schiebel, W., Pelissier, T., Riedel, L., Thalmeir, S., Schiebel, R., Kempe, D., Lottspeich, F., Sanger, H. L., and Wassenegger, M. 1998. Isolation of an RNA-directed RNA polymerase-specific cDNA clone from tomato. Plant Cell 10: 2087-2101.

Schwarz, D. S., Hutvágner, G., Haley, B., and Zamore, P. D. 2002. Evidence that siRNAs function as guides, not primers, in the *Drosophila* and human RNAi pathways. Mol. Cell 10: 537-548.

Sijen, T., Fleenor, J., Simmer, F., Thijssen, K. L., Parrish, S., Timmons, L., Plasterk, R. H., and Fire, A. 2001. On the role of RNA amplification in dsRNA-triggered gene silencing. Cell 107: 465-476.

Smardon, A., Spoerke, J., Stacey, S., Klein, M., Mackin, N., and Maine, E. 2000. EGO-1 is related to RNA-directed RNA polymerase and functions in germ-line development and RNA interference in *C. elegans*. Curr. Biol. 10: 169-178.

Tabara, H., Sarkissian, M., Kelly, W. G., Fleenor, J., Grishok, A., Timmons, L., Fire, A., and Mello, C. C. 1999. The rde-1 gene, RNA interference, and transposon silencing in *C. elegans*. Cell 99: 123-132.

Tijsterman, M., Ketting, R. F., Okihara, K. L., Sijen, T., and Plasterk, R. H. 2002. RNA helicase MUT-14-dependent gene silencing triggered in *C. elegans* by short antisense RNAs. Science 295: 694-697.

Tuschl, T., Zamore, P. D., Lehmann, R., Bartel, D. P., and Sharp, P. A. 1999. Targeted mRNA degradation by double-stranded RNA in vitro. Genes & Dev. 13: 3191-3197.

Vaistij, F. E., Jones, L., and Baulcombe, D. C. 2002. Spreading of RNA targeting and DNA methylation in RNA silencing requires transcription of the target gene and a putative RNA-dependent RNA polymerase. Plant Cell 14: 857-867.

Vaucheret, H., Beclin, C., and Fagard, M. 2001. Post-transcriptional gene silencing in plants. J. Cell Sci. 114: 3083-3091.

Waterhouse, P. M., Wang, M. B., and Lough, T. 2001. Gene silencing as an adaptive defence against viruses. Nature 411: 834-842.

Williams, R. W. and Rubin, G. M. 2002. ARGONAUTE1 is required for efficient RNA interference in *Drosophila* embryos. Proc. Natl. Acad. Sci. 99: 6889-6894.

Zamore, P. D., Tuschl, T., Sharp, P. A., and Bartel, D. P. 2000. RNAi: Double-stranded RNA directs the ATP-dependent cleavage of mRNA at 21 to 23 nucleotide intervals. Cell 101: 25-33.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A vector encoding an engineered pre-miRNA comprising an RNAi agent, which comprises a sense strand and an antisense strand; wherein one or more 5'-terminal nucleotides that are within 5 or fewer nucleotides from the 5' end of the antisense strand are substituted with a nucleotide, which does not form a Watson-Crick base pair when the antisense strand is base paired with a target sequence in a human mRNA; wherein the last two nucleotides at the 3' end of the antisense strand are UU; and wherein all nucleotides in the antisense strand are perfectly complementary to the target sequence other than the UU nucleotides at the 3' end of the antisense strand and the one or more terminal nucleotides, which are substituted to not form a Watson-Crick base pair.

2. The vector of claim 1, wherein the vector is an adeno-associated virus (AAV) vector.

3. The vector of claim 2, wherein the antisense strand is 19-22 nucleotides in length.

4. The vector of claim 3, wherein only 1-3 of the one or more terminal nucleotides are substituted with nucleotides which do not form Watson-Crick base pairs.

5. The vector of claim 3, wherein only 1-2 of the one or more 5'-terminal nucleotides are substituted with nucleotides which do not form Watson-Crick base pairs.

6. The vector of claim 3, wherein only 1-2 terminal nucleotides that are within 3 or fewer nucleotides from the 5' end of the antisense strand are substituted with nucleotides which do not form Watson-Crick base pairs.

7. The vector of claim 3, wherein only one of the one or more 5'-terminal nucleotides is substituted with a nucleotide which does not form Watson-Crick base pairs.

8. The vector of claim 3, wherein only one terminal nucleotide that is within 3 or fewer nucleotides from the 5' end of the antisense strand is substituted with a nucleotide which does not form Watson-Crick base pairs.

9. The vector of claim 3, wherein the first terminal nucleotide at the 5' end of the antisense strand is substituted with a nucleotide which does not form Watson-Crick base pairs.

10. The vector of claim 9, wherein the substitution is a C→U substitution, with the U forming a G:U wobble base pair with a corresponding G in the target sequence in the wild-type human mRNA.

11. A pharmaceutical composition comprising the vector of claim 6.

12. The vector of claim 6, wherein the vector encodes a pri-miRNA which comprises the pre-miRNA.

13. A vector encoding an engineered pre-miRNA, said pre-miRNA comprising a single strand that forms a hairpin which comprises a duplex stem and loop; said duplex stem comprising an RNAi agent formed by a sense strand on a first portion of the stem and an antisense strand on a second portion of the stem; wherein each of the first and second stem portions are 18-25 nucleotides in length and the loop is 2-9 nucleotides in length; wherein one or more 5'-terminal nucleotides that are within 5 or fewer nucleotides from the 5' end of the antisense strand are substituted with a nucleotide that does not form a Watson-Crick base pair when the antisense strand is base paired with a target sequence in a human mRNA; wherein the last two nucleotides at the 3' end of the antisense strand are UU; and wherein all nucleotides in the antisense strand are perfectly complementary to the target sequence other than the UU nucleotides at the 3' end of the antisense strand and the one or more terminal nucleotides that are substituted to not form a Watson-Crick base pair.

14. The vector of claim 13, wherein the vector is an adeno-associated virus (AAV) vector.

15. The vector of claim 14, wherein the antisense strand is 19-22 nucleotides in length.

16. The vector of claim 15, wherein only 1-3 of the one or more 5'-terminal nucleotides are substituted with nucleotides which do not form Watson-Crick base pairs.

17. The vector of claim 15, wherein only 1-2 of the one or more 5'-terminal nucleotides are substituted with nucleotides which do not form Watson-Crick base pairs.

18. The vector of claim 15, wherein only 1-2 terminal nucleotides that are within 3 or fewer nucleotides from the 5' end of the antisense strand are substituted with nucleotides which do not form Watson-Crick base pairs.

19. The vector of claim 15, wherein only one of the one or more 5'-terminal nucleotides is substituted with a nucleotide which does not form Watson-Crick base pairs.

20. The vector of claim 15, wherein only one terminal nucleotide that is within 3 or fewer nucleotides from the 5' end of the antisense strand is substituted with a nucleotide which does not form Watson-Crick base pairs.

21. The vector of claim 15, wherein the first terminal nucleotide at the 5' end of the antisense strand is substituted with a nucleotide which does not form Watson-Crick base pairs.

22. The vector of claim 21, wherein the substitution is a C U substitution, with the U forming a G:U wobble base pair with a corresponding G in the target mRNA sequence.

23. A pharmaceutical composition comprising the vector of claim 18.

24. The vector of claim 18, wherein the vector encodes a pri-miRNA which comprises the pre-miRNA.

* * * * *

UNITED STATES PATENT AND TRADEMARK OFFICE
CERTIFICATE OF CORRECTION

PATENT NO. : 11,459,562 B2
APPLICATION NO. : 16/440722
DATED : October 4, 2022
INVENTOR(S) : Zamore et al.

Page 1 of 1

It is certified that error appears in the above-identified patent and that said Letters Patent is hereby corrected as shown below:

In the Specification

At Column 1, Lines 37-43:
Delete:
"STATEMENT REGARDING FEDERALLY SPONSORED RESEARCH OR DEVELOPMENT
This invention was made with government support under Grant Nos. GM062862, GM065236, and GM05880 awarded by the National Institutes of Health. The government has certain rights in the invention."

And insert:
--STATEMENT REGARDING FEDERALLY SPONSORED RESEARCH OR DEVELOPMENT
This invention was made with government support under Grant No. GM062862 awarded by the National Institutes of Health. The government has certain rights in the invention.--

Signed and Sealed this
Fifteenth Day of April, 2025

Coke Morgan Stewart
*Acting Director of the United States Patent and Trademark Office*